US012345717B2

(12) United States Patent
Ward et al.

(10) Patent No.: US 12,345,717 B2
(45) Date of Patent: Jul. 1, 2025

(54) BIOMARKERS AND METHODS RELATING TO ALZHEIMER'S DISEASE

(71) Applicants: ELECTROPHORETICS LIMITED, Surrey (GB); KING'S COLLEGE LONDON, London (GB)

(72) Inventors: Malcolm Andrew Ward, Surrey (GB); Abdul Hye, London (GB); Simon Harold Lovestone, London (GB); Richard James Butler Dobson, London (GB)

(73) Assignees: ELECTROPHORETICS LIMITED, Surrey (GB); KING'S COLLEGE LONDON, London (GB)

( * ) Notice: Subject to any disclaimer, the term of this patent is extended or adjusted under 35 U.S.C. 154(b) by 0 days.

(21) Appl. No.: 15/104,149

(22) PCT Filed: Dec. 12, 2014

(86) PCT No.: PCT/GB2014/053692
§ 371 (c)(1),
(2) Date: Jun. 13, 2016

(87) PCT Pub. No.: WO2015/087087
PCT Pub. Date: Jun. 18, 2015

(65) Prior Publication Data
US 2017/0219611 A1    Aug. 3, 2017

(30) Foreign Application Priority Data

Dec. 13, 2013 (GB) .................................. 1322094

(51) Int. Cl.
*G01N 33/68*    (2006.01)

(52) U.S. Cl.
CPC . *G01N 33/6896* (2013.01); *G01N 2800/2814* (2013.01); *G01N 2800/2821* (2013.01); *G01N 2800/52* (2013.01)

(58) Field of Classification Search
CPC ....... G01N 33/6896; G01N 2800/2814; G01N 2800/2821; G01N 2800/52
See application file for complete search history.

(56) References Cited

U.S. PATENT DOCUMENTS

| 4,376,110 A | 3/1983 | David et al. |
| 4,946,778 A | 8/1990 | Ladner et al. |
| 5,093,246 A | 3/1992 | Cech et al. |

FOREIGN PATENT DOCUMENTS

| JP | 2005510722 A | 4/2005 |
| JP | 2005536729 A | 12/2005 |
| JP | 2007513337 A | 5/2007 |
| JP | 2011209291 A | 10/2011 |
| WO | 2006/035237 A2 | 4/2006 |
| WO | PCT/AU2012/000475 | * 5/2012 ..... G01N 2333/4709 |

OTHER PUBLICATIONS

Erlandsen et al, Scand J Clin Lab Invest, 1999; 59:1-8.*
Lofberg et al, Scand J Clin Lab Invest, 1979; 39:619-26.*
RayBiotech Catalog, 2015, Human Cystatin C ELISA kit: 1-12.*
Hanley JA, McNeil BJ. The meaning and use of the area under a receiver operating characteristic (ROC) curve. Radiology. 1982; 143:29-36 (Year: 1982).*
Davidsson et al., Neural, Trans. 104: 711-720, 1997 (Year: 1997).*
Ray et al., Nature Medicine vol. 13, No. 11, published Nov. 2007 (Year: 2007).*
Zhang et al., Proteomics, 4:244-256, 2004 (Year: 2004).*
Koehler, G. et al., "Continuous cultures of fused cells secreting antibody of predefined specificity", Nature, vol. 256, Aug. 7, 1975, pp. 495-497.
Kozbor, D. et al., "The production of monoclonal antibodies from human lymphocytes", Immunology Today, vol. 4, No. 3, 1983, pp. 72-79.
Cote, R.J. et al., "Generation of human monoclonal antibodies reactive with cellular antigens", Proceedings of the National Academy of Sciences of the USA, vol. 80, Apr. 1983, pp. 2026-2030.
Cole, S.P.C. et al., "The EBV-Hybridoma Technique and Its Application to Human Lunch Cancer", Monoclonal Antibodies and Cancer Therapy, 1985, Alan R. Liss, Inc., pp. 77-96.
Morrison, S.L., et al., "Chimeric human antibody molecules: Mouse antigen-binding domains with human constant region domains", Proceedings of the National Academy of Sciences of the USA, vol. 81, Nov. 1984, pp. 6851-6855.

(Continued)

*Primary Examiner* — Kimberly Ballard
*Assistant Examiner* — Stacey N MacFarlane
(74) *Attorney, Agent, or Firm* — ArentFox Schiff LLP

(57) ABSTRACT

Alzheimer's disease, the most common cause of dementia in older individuals, is a debilitating neurodegenerative disease for which there is currently no cure. In the past, AD could only be definitively diagnosed by brain biopsy or upon autopsy after a patient died. These methods, which demonstrate the presence of the characteristic plaque and tangle lesions in the brain, are still considered the gold standard for the pathological diagnoses of AD. However, in the clinical setting brain biopsy is rarely performed and diagnosis depends on a battery of neurological, psychometric and biochemical tests, including the measurement of biochemical markers such as the ApoE and tau proteins or the beta-amyloid peptide in cerebrospinal fluid and blood. The present invention discloses and describes panels of makers that are differentially expressed in the disease state relative to their expression in the normal state and, in particular, identifies and describes panels of makers associated with neurocognitive disorders. Such biomarker panel might have considerable value in triaging patients with early memory disorders to yet more specific but more invasive and costly approaches such as molecular markers in CSF and on PET imaging in clinical trials and possibly in clinical practice.

16 Claims, No Drawings
Specification includes a Sequence Listing.

(56) References Cited

OTHER PUBLICATIONS

Neuberger, M.S. et al., "Recombinant antibodies possessing novel effector functions", Nature, vol. 312, Dec. 13, 1984, pp. 604-608.
Takeda, S. et al., "Construction of chimaeric processed immunoglobulin genes containing mouse variable and human constant region sequences", Nature, vol. 314, Apr. 4, 1985, pp. 452-454.
Bird, R.E. et al., "Single-Chain Antigen-Binding Proteins", Science, vol. 242, Oct. 21, 1988, pp. 423-426.
Huston, J.S et al., "Protein engineering of antibody binding sites: Recovery of specific activity in an anti-digoxin single-chain Fv analogue produced in *Escherichia coli*", Proceedings of the National Academy of Sciences of the USA, vol. 85, Aug. 1998, pp. 5879-5883.
Ward, E.S. et al., "Binding activities of a repertoire of single immunoglobulin variable domains secreted from *Escherichia coli*", Nature, vol. 341, Oct. 12, 1989, pp. 544-546.
Huse, W.D. et al., "Generation of a Large Combinatorial Library of Immunoglobulin Repertoire in Phage Lambda", Science, vol. 246, Dec. 8, 1989, pp. 1275-1281.
Rossier, J.S. et al., "Microchannel networks for electrophoretic separations", Electrophoresis, vol. 20, 1999, pp. 727-731.
Lucas, J.J. et al., "Decreased nuclear β-catenin, tau, hyperphosphorylation and neurodegeneration in GSK-3B conditional transgenic mice", The EMBO Journal, vol. 20, No. 1 & 2, 2001, pp. 27-39.
Creighton, T.E., "Proteins Structures And Molecular Principles", W.H. Freeman and Co., N.Y., 1983, pp. 50-60.
Marasco, W.A. et al., "Design, intracellular expression, and activity of a human anti-human immunodeficiency virus type 1 gp120 single-chain antibody", Proceedings of the National Academy of Sciences of the USA, vol. 90, Aug. 1993, pp. 7889-7893.
Rossi, J.J., "Making ribozymes work in cells", Current Biology, vol. 4, No. 5, 1994, pp. 469-471.
Hye, A. et al., "Proteome-based plasma biomarkers for Alzheimer's disease", Brain, vol. 129, 2006, pp. 3042-3050.
Cutler, P. et al., "Proteomic identification and early validation of complement 1 inhibitor and pigment epithelium-derived factor: Two novel biomarkers of Alzheimer's disease in human plasma", Proteomics Clinical Applications, vol. 2, 2008, pp. 467-477.
Akuffo, E.L. et al., "The discovery and early validation of novel plasma biomarkers in mild-to-moderate Alzheimer's disease patients responding to treatment with rosiglitazone", Biomarkers of Alzheimer's Disease, vol. 13, No. 6, 2008, pp. 618-636.
Kimura, M. et al., "Assessment of cerebrospinal fluid levels of serum amyloid p. component in patients with Alzheimer's disease", Neuroscience Letters, vol. 273, 1999, pp. 137-139.
Kessler, H. et al., "Cerebrospinal fluid diagnostic markers correlate with lower plasma copper and ceruloplasmin in patients with Alzheimer's disease", Journal of Neural Transmission, vol. 113, 2006, pp. 1763-1769.
Mulder, S.D. et al., "Evaluation of Intrathecal Serum Amyloid P (SAP) and C-Reactive Protein (CRP) Synthesis in Alzheimer's Disease with the Use of Index Values", Journal of Alzheimer's Disease, vol. 22, 2010, pp. 1073-1079.
Thambisetty, M. et al., "Association of plasma clusterin concentration with severity, pathology, and progression in Alzheimer disease", Archives of General Psychiatry, vol. 67, No. 7, Jul. 2010, pp. 739-748.
Velayudhan, L. et al., "Plasma Transthyretin as a Candidate Marker for Alzheimer's disease", Journal of Alzheimer's Disease, vol. 28, 2012, pp. 369-375.
Thambisetty, M. et al., "Proteome-Based Plasma Markers of Brain Amyloid Beta Deposition in Non-Demented Older Individuals", Journal of Alzheimer's Disease, vol. 22, No. 4, 2010, pp. 1099-1109.
Lovestone, S. et al., "AddNeuroMed—The European Collaboration for the Discovery of Novel Biomarkers for Alzheimer's Disease", Biomarkers in Brain Disease, Annals of the New York Academy of Sciences, vol. 1180, 2009, pp. 36-46.
Petersen, R.C. et al., "Mild Cognitive Impairment: Clinical Characterization and Outcome", Archives of Neurology, vol. 56, Mar. 1999, pp. 303-308. Correction—Jun. 1999 p. 760.
Wenham, P.R. et al., "Apolipoprotein E genotyping by one-stage PCR", The Lancet, vol. 337, May 11, 1991, pp. 1158-1159.
Simmons, A. et al., "MRI Measures of Alzheimer's Disease and the AddNeuroMed Study", Biomarkers in Brain Disease, Annals of the New York Academy of Sciences, vol. 1180, 2009, pp. 47-55.
Jack, C.R. Jr. et al., "The Alzheimer's Disease Neuroimaging Initiative (ADNI): MRI Methods", Journal of Magnetic Resonance Imaging, vol. 27, No. 4, Apr. 2008, pp. 685-691.
Simmons, A. et al., "The AddNeuroMed framework for multi-centre MRI assessment of Alzheimer's disease: experience from the first 24 months", International Journal of Geriatric Psychiatry, vol. 26, 2011, pp. 75-82.
Westman, E. et al., "AddNeuroMed and ADNI: Similar patterns of Alzheimer's atrophy and automated MRI classification accuracy in Europe and North America", NeuroImage, vol. 58, 2011, pp. 818-828.
Westman, E. et al., "Multivariate analysis of MRI data for Alzheimer's disease, mild cognitive impairment and healthy controls", NeuroImage, vol. 54, 2011, pp. 1178-1187.
Thambisetty, M. et al., "Plasma Biomarkers of Brain Atrophy in Alzheimer's Disease", PLOS One, vol. 6, Issue 12, Dec. 2011, e28527.
Westman, E. et al., "Regional Magnetic Resonance Imaging Measures for Multivariate Analysis in Alzheimer's Disease and Mild Cognitive Impairment", Brain Topography, vol. 26, 2013, pp. 9-23.
Guentert, A. et al., "Plasma Gelsolin is Decreased and Correlates with Rate of Decline in Alzheimer's Disease", Journal of Alzheimer's Disease, vol. 21, 2010, pp. 585-596.
Hu, W.T. et al., "Plasma multianalyte profiling in mild cognitive impairment and Alzheimer disease", Neurology, vol. 79, Aug. 28, 2012, pp. 897-905.
O'Bryant, S.E. et al., "A Blood-Based Screening Tool for Alzheimer's Disease That Spans Serum and Plasma: Findings from TARC and ADNI", PLOS One, vol. 6, Issue 12, Dec. 2011, e28092.
Ray, S. et al., "Classification and prediction of clinical Alzheimer's diagnosis based on plasma signaling proteins", Nature Medicine, vol. 13, No. 11, Nov. 2007, pp. 1359-1362.
Gangemi, S. et al., "Effect of levodopa on interleukin-15 and RANTES circulating levels in patients affected by Parkinson's disease", Mediators of Inflammation, vol. 12, Aug. 2003, pp. 251-253.
Grzybicki, D. et al., "Expression of monocyte chemoattractant protein (MCP-1) and nitric oxide synthase-2 following cerebral trauma", Acta Neuropathologica, vol. 95, 1998, pp. 98-103.
Tripathy, D. et al., "RANTES upregulation in the Alzheimer's disease brain: a possible neuroprotective role", Neurobiology of Aging, vol. 31, Jan. 2010, pp. 8-16.
Perrin, R.J. et al., "Identification and Validation of Novel Cerebrospinal Fluid Biomarkers for Staging Early Alzheimer's Disease", PLOS One, vol. 6, Issue 1, Jan. 2011, e16032.
Degiorgio, C.M. et al., "Neuron-Specific Enolase, a Marker of Acute Neuronal Injury, is Increased in Complex Partial Status Epilepticus", Epilepsia, vol. 37, No. 7, 1996, pp. 606-609.
Hatfield, R.H. et al., "CSF neuron-specific enolase as a quantitative marker of neuronal damage in a rat stroke model", Brain Research, vol. 577, 1992, pp. 249-252.
Chaves, M.L. et al., "Serum levels of S100B and NSE proteins in Alzheimer's disease patients", Journal of Neuroinflammation, vol. 7, 2010, 7 pages.
Blennow, K. et al., "Neuron specific enolase in cerebrospinal fluid: a biochemical marker for neuronal degeneration in dementia disorders?", Journal of Neural Transmission, [P-D Sect], vol. 8, 1994, pp. 183-191.
Lewis, T.L. et al., "Overexpression of Human Apolipoprotein A-I Preserves Cognitive Function and Attenuates Neuroinflammation and Cerebral Amyloid Angiopathy in a Mouse Model of Alzheimer Disease", The Journal of Biological Chemistry, vol. 285, Nov. 19, 2010, pp. 36958-36968.

(56) References Cited

OTHER PUBLICATIONS

Takechi, R. et al., "Differential effects of dietary fatty acids on the cerebral distribution of plasma-derived apo B lipoproteins with amyloid-β", British Journal of Nutrition, vol. 103, 2010, pp. 652-662.
Eichner, J.E. et al., "Apolipoprotein E Polymorphism and Cardiovascular Disease: A Huge Review", American Journal of Epidemiology, vol. 155, No. 6, Mar. 15, 2002, pp. 487-495.
Gupta, V.B., et al., "Plasma apolipoprotein E and Alzheimer disease risk: The AIBL study of aging", Neurology, vol. 76, Mar. 22, 2011, pp. 1091-1098.
Siest, G., et al. "Apolipoprotein E Polymorphism and Serum Concentration in Alzheimer's Disease in Nine European Centres: the ApoEurope Study", Clinical Chemistry and Laboratory Medicine, vol. 38, 2000, pp. 721-730.
Darreh-Shori, T. et al., "Differential levels of apolipoprotein E and butyrylcholinesterase show strong association with pathological signs of Alzheimer's disease in the brain in vivo", Neurobiology of Aging, vol. 32, Issue 12, 2011, pp. 2320.e15-2320.e32.
Darreh-Shori, T. et al., "The apolipoprotein E ε4 allele plays pathological roles in AD through high protein expression and interaction with butyrylcholinesterase", Neurobiology of Aging, 2009, 13 pages.
Kiddle, S.J., et al., "Plasma Based Markers of [11C] PiB-PET Brain Amyloid Burden", PLOS One, vol. 7, Issue 9, Sep. 24, 2012, e44260.
Furney, S.J., et al., "Combinatorial Markers of Mild Cognitive Impairment Conversion to Alzheimer's Disease—Cytokines and MRI Measures Together Predict Disease Progression", Journal of Alzheimer's Disease, vol. 26, 2011, pp. 395-405.
Brys, M., et al., "Magnetic Resonance Imaging Improves Cerebrospinal Fluid Biomarkers in the Early Detection of Alzheimer's Disease", Journal of Alzheimer's Disease, vol. 16, No. 2, Sep. 30, 2009, pp. 351-362.
Fleitmann, J., International Search Report, PCT/GB2014/053692, Apr. 1, 2015, 5 pages.
Velayudhan, L. et al., "Plasma transthyretin as a candidate marker of cognitive decline and severity in Alzheimer's disease", Alzheimer's & Dementia: The Journal of the Alzheimer's Association, P3-243, vol. 6, No. 4, Jul. 1, 2010, pp. S522-S523.
Lunnon, K. et al., "A Blood Gene Expression Marker of Early Alzheimer's Disease", Journal of Alzheimer's Disease, vol. 33, 2013, pp. 737-753.
Hye, A. et al., "Plasma proteins predict conversion to dementia from prodromal disease", Alzheimer's & Dementia: The Journal of the Alzheimer's Association, vol. 10, 2014, pp. 799-807.
Japanese Notification of Reasons for Refusal dated Sep. 27, 2018 and issued for Japanese Application No. 2016-538603.
Office Action issued in European Patent Application No. 14830849.7 dated Apr. 25, 2019, pp. 1-4.
Office Action issued in Canadian Office for Canadian Application No. 2,933,398, dated Oct. 26, 2021 (5 pages).
Sun-Ho et al.; "Human Serum Transthyretin Levels Correlate Inversely with Alzheimer's Disease"; Journal of Alzheimer's Disease, 25:1, pp. 77-84, 2014.
Office Action issued in Canadian Patent Office for Canadian Application No. 2,933,398, dated Mar. 29, 2021 (5 pages).
Wu, Charlie W., et al., "Identification and localization of major soluble vitreous proteins in human ocular tissue", American Journal Of Ophthalmology, vol. 137, No. 4 (2004), pp. 655-661.
Kim, Jeong Hun, et al., "The role of clusterin in retinal development and free radical damage", British Journal Of Ophthalmology, vol. 91, (2007), pp. 1541-1546.
Nishio, Chika, et al., "Involvement of cystatin C in oxidative stress-induced apoptosis of cultured rat CNS neurons", Brain Research vol. 873, (2000), pp. 252-262.
Bruijn, et al., "Immunoglobulins and a1-Acid Glycoprotein Do Not Contribute to the Cholesterol Crystallization-Promoting Effect of Concanavalin A-Binding Biliary Protein", Hepatology, vol. 20, No. 3, (1994), pp. 626-632.
Danila, Delia, et al., "Antibody-Labeled Liposomes for CT Imaging of Atherosclerotic Plaques: In Vitro Investigation of an Anti-ICAM Antibody-Labeled Liposome Containing Iohexol for Molecular Imaging of Atherosclerotic Plaques via Computed Tomography", Texas Heart Institute Journal, vol. 36, No. 5, (2009), pp. 393-403.
Mionnet, Cyrille, et al., "Identification of a New Stromal Cell Type Involved in the Regulation of Inflamed B Cell Follicles", PLoS Biology, vol. 11, Issue 10, (2013), e1001672, pp. 1-13.
Abe, Riichiro, et al., "Topical application of anti-angiogenic peptides based on pigment epithelium-derived factor can improve psoriasis", Journal of Dermatological Science, vol. 57, (2010), pp. 183-191.
Khazanov, Elena, et al., "Specific Detection of Gastric a-Antitrypsin by Immobilized Trypsin on PolyHEMA Films", Molecular Pharmaceutics, vol. 7, No. 4, (2010), pp. 944-952.
Kim, Youngkyun, et al., "Human Cytomegalovirus Clinical Strain-Specific microRNA miR-UL148D Targets the Human Chemokine RANTES during Infection", PLoS Pathogens, vol. 8, Issue 3 (2012), e1002577, pp. 1-12.
Cho, Kyung-Hyun, et al., "The function, composition, and particle size of high-density lipoprotein were severely impaired in an oliguric phase of hemorrhagic fever with renal syndrome patients", Clinical Biochemistry, vol. 41, (2008), pp. 56-64.
"AAT Antibodies", santa cruz biotechnology, inc., Available on internet at: https://web.archive.org/web/20120302134000/http:/www.scbt.com/table-aat.html, Mar. 2, 2012, 1 page.
"AGP Antibodies", santa cruz biotechnology, inc., Available on internet at: https://web.archive.org/web/20120302023157/http:/www.scbt.com/table-agp.html, Mar. 2, 2012, 1 page.
"Apolipoprotein Antibodies", santa cruz biotechnology, inc., Available on internet at:https://web.archive.org/web/20120303014317/http:/www.scbt.com/table-apolipoprotein.html, Mar. 3, 2012, 4 pages.
"C4 Antibodies", santa cruz biotechnology, inc., Available on internet at:https://web.archive.org/web/20120302083601/http:/www.scbt.com/table-c4.html, Mar. 2, 2012, 1 page.
"Clusterin Antibodies", santa cruz biotechnology, inc., Available on internet at:https://web.archive.org/web/20120617060616/http:/www.scbt.com/table-clusterin.html, Jun. 17, 2012, 1 Page.
"Cystatin Antibodies", santa cruz biotechnology, inc., Available on internet at:https://web.archive.org/web/20120302071955/http:/www.scbt.com/table-cystatin.html, Mar. 2, 2012, 2 pages.
"ICAM Antibodies", santa cruz biotechnology, inc., Available on internet at:https://web.archive.org/web/20120302082819/http:/www.scbt.com/table-icam.html, Mar. 2, 2012, 2 pages.
"RANTES Antibodies", santa cruz biotechnology, inc., Available on internet at:https://web.archive.org/web/20120302205709/http:/www.scbt.com/table-rantes.html, Mar. 2, 2012, 1 page.
"PEDF Antibodies", santa cruz biotechnology, inc., Available on internet at:https://web.archive.org/web/20120302074907/http:/www.scbt.com/table-pedf.html, Mar. 2, 2012, 1 page.
"Prealbumin Antibodies", santa cruz biotechnology, inc., Available on internet at:https://web.archive.org/web/20120303005730/http:/www.scbt.com/table-prealbumin.html, Mar. 3, 2012, 1 Page.
"Primary Antibodies", santa cruz biotechnology, inc., Available on internet at:https://web.archive.org/web/20120209145938/http:/www.scbt.com/primary_antibodies.html, Feb. 9, 2012, 1 page.

* cited by examiner

SEQUENCE LISTING

```
<160> NUMBER OF SEQ ID NOS: 27

<210> SEQ ID NO 1
<211> LENGTH: 147
<212> TYPE: PRT
<213> ORGANISM: Homo sapiens

<400> SEQUENCE: 1

Met Ala Ser His Arg Leu Leu Leu Cys Leu Ala Gly Leu Val Phe
1               5                   10                  15

Val Ser Glu Ala Gly Pro Thr Gly Thr Gly Glu Ser Lys Cys Pro Leu
            20                  25                  30

Met Val Lys Val Leu Asp Ala Val Arg Gly Ser Pro Ala Ile Asn Val
        35                  40                  45

Ala Val His Val Phe Arg Lys Ala Ala Asp Asp Thr Trp Glu Pro Phe
    50                  55                  60

Ala Ser Gly Lys Thr Ser Glu Ser Gly Glu Leu His Gly Leu Thr Thr
65                  70                  75                  80

Glu Glu Glu Phe Val Glu Gly Ile Tyr Lys Val Glu Ile Asp Thr Lys
                85                  90                  95

Ser Tyr Trp Lys Ala Leu Gly Ile Ser Pro Phe His Glu His Ala Glu
            100                 105                 110

Val Val Phe Thr Ala Asn Asp Ser Gly Pro Arg Arg Tyr Thr Ile Ala
        115                 120                 125

Ala Leu Leu Ser Pro Tyr Ser Tyr Ser Thr Thr Ala Val Val Thr Asn
    130                 135                 140

Pro Lys Asp
145

<210> SEQ ID NO 2
<211> LENGTH: 449
<212> TYPE: PRT
<213> ORGANISM: Homo sapiens

<400> SEQUENCE: 2
```

```
Met Met Lys Thr Leu Leu Phe Val Gly Leu Leu Leu Thr Trp Glu
1               5                   10                  15

Ser Gly Gln Val Leu Gly Asp Gln Thr Val Ser Asp Asn Glu Leu Gln
                20                  25                  30

Glu Met Ser Asn Gln Gly Ser Lys Tyr Val Asn Lys Glu Ile Gln Asn
            35                  40                  45

Ala Val Asn Gly Val Lys Gln Ile Lys Thr Leu Ile Glu Lys Thr Asn
    50                  55                  60

Glu Glu Arg Lys Thr Leu Leu Ser Asn Leu Glu Glu Ala Lys Lys Lys
65              70                  75                  80

Lys Glu Asp Ala Leu Asn Glu Thr Arg Glu Ser Glu Thr Lys Leu Lys
                85                  90                  95

Glu Leu Pro Gly Val Cys Asn Glu Thr Met Met Ala Leu Trp Glu Glu
            100                 105                 110

Cys Lys Pro Cys Leu Lys Gln Thr Cys Met Lys Phe Tyr Ala Arg Val
        115                 120                 125

Cys Arg Ser Gly Ser Gly Leu Val Gly Arg Gln Leu Glu Glu Phe Leu
    130                 135                 140

Asn Gln Ser Ser Pro Phe Tyr Phe Trp Met Asn Gly Asp Arg Ile Asp
145                 150                 155                 160

Ser Leu Leu Glu Asn Asp Arg Gln Gln Thr His Met Leu Asp Val Met
                165                 170                 175

Gln Asp His Phe Ser Arg Ala Ser Ser Ile Ile Asp Glu Leu Phe Gln
            180                 185                 190

Asp Arg Phe Phe Thr Arg Glu Pro Gln Asp Thr Tyr His Tyr Leu Pro
        195                 200                 205

Phe Ser Leu Pro His Arg Pro His Phe Phe Phe Pro Lys Ser Arg
    210                 215                 220

Ile Val Arg Ser Leu Met Pro Phe Ser Pro Tyr Glu Pro Leu Asn Phe
225                 230                 235                 240

His Ala Met Phe Gln Pro Phe Leu Glu Met Ile His Glu Ala Gln Gln
                245                 250                 255

Ala Met Asp Ile His Phe His Ser Pro Ala Phe Gln His Pro Pro Thr
            260                 265                 270

Glu Phe Ile Arg Glu Gly Asp Asp Arg Thr Val Cys Arg Glu Ile
        275                 280                 285

Arg His Asn Ser Thr Gly Cys Leu Arg Met Lys Asp Gln Cys Asp Lys
    290                 295                 300

Cys Arg Glu Ile Leu Ser Val Asp Cys Ser Thr Asn Asn Pro Ser Gln
305                 310                 315                 320

Ala Lys Leu Arg Arg Glu Leu Asp Glu Ser Leu Gln Val Ala Glu Arg
                325                 330                 335

Leu Thr Arg Lys Tyr Asn Glu Leu Leu Lys Ser Tyr Gln Trp Lys Met
            340                 345                 350

Leu Asn Thr Ser Ser Leu Leu Glu Gln Leu Asn Glu Gln Phe Asn Trp
        355                 360                 365

Val Ser Arg Leu Ala Asn Leu Thr Gln Gly Glu Asp Gln Tyr Tyr Leu
    370                 375                 380

Arg Val Thr Thr Val Ala Ser His Thr Ser Asp Ser Asp Val Pro Ser
385                 390                 395                 400

Gly Val Thr Glu Val Val Lys Leu Phe Asp Ser Asp Pro Ile Thr
                405                 410                 415
```

```
Val Thr Val Pro Val Glu Val Ser Arg Lys Asn Pro Lys Phe Met Glu
            420                 425                 430

Thr Val Ala Glu Lys Ala Leu Gln Glu Tyr Arg Lys Lys His Arg Glu
            435                 440                 445

Glu

<210> SEQ ID NO 3
<211> LENGTH: 146
<212> TYPE: PRT
<213> ORGANISM: Homo sapiens

<400> SEQUENCE: 3

Met Ala Gly Pro Leu Arg Ala Pro Leu Leu Leu Leu Ala Ile Leu Ala
1               5                   10                  15

Val Ala Leu Ala Val Ser Pro Ala Ala Gly Ser Ser Pro Gly Lys Pro
            20                  25                  30

Pro Arg Leu Val Gly Gly Pro Met Asp Ala Ser Val Glu Glu Glu Gly
            35                  40                  45

Val Arg Arg Ala Leu Asp Phe Ala Val Gly Glu Tyr Asn Lys Ala Ser
        50                  55                  60

Asn Asp Met Tyr His Ser Arg Ala Leu Gln Val Val Arg Ala Arg Lys
65                  70                  75                  80

Gln Ile Val Ala Gly Val Asn Tyr Phe Leu Asp Val Glu Leu Gly Arg
                85                  90                  95

Thr Thr Cys Thr Lys Thr Gln Pro Asn Leu Asp Asn Cys Pro Phe His
            100                 105                 110

Asp Gln Pro His Leu Lys Arg Lys Ala Phe Cys Ser Phe Gln Ile Tyr
            115                 120                 125

Ala Val Pro Trp Gln Gly Thr Met Thr Leu Ser Lys Ser Thr Cys Gln
        130                 135                 140

Asp Ala
145

<210> SEQ ID NO 4
<211> LENGTH: 201
<212> TYPE: PRT
<213> ORGANISM: Homo sapiens

<400> SEQUENCE: 4

Met Ala Leu Ser Trp Val Leu Thr Val Leu Ser Leu Leu Pro Leu Leu
1               5                   10                  15

Glu Ala Gln Ile Pro Leu Cys Ala Asn Leu Val Pro Val Pro Ile Thr
            20                  25                  30

Asn Ala Thr Leu Asp Arg Ile Thr Gly Lys Trp Phe Tyr Ile Ala Ser
            35                  40                  45

Ala Phe Arg Asn Glu Glu Tyr Asn Lys Ser Val Gln Glu Ile Gln Ala
        50                  55                  60

Thr Phe Phe Tyr Phe Thr Pro Asn Lys Thr Glu Asp Thr Ile Phe Leu
65                  70                  75                  80

Arg Glu Tyr Gln Thr Arg Gln Asp Gln Cys Ile Tyr Asn Thr Thr Tyr
                85                  90                  95

Leu Asn Val Gln Arg Glu Asn Gly Thr Ile Ser Arg Tyr Val Gly Gly
            100                 105                 110

Gln Glu His Phe Ala His Leu Leu Ile Leu Arg Asp Thr Lys Thr Tyr
            115                 120                 125

Met Leu Ala Phe Asp Val Asn Asp Glu Lys Asn Trp Gly Leu Ser Val
```

Tyr Ala Asp Lys Pro Glu Thr Thr Lys Glu Gln Leu Gly Glu Phe Tyr
145                 150                 155                 160

Glu Ala Leu Asp Cys Leu Arg Ile Pro Lys Ser Asp Val Val Tyr Thr
                165                 170                 175

Asp Trp Lys Lys Asp Lys Cys Glu Pro Leu Glu Lys Gln His Glu Lys
            180                 185                 190

Glu Arg Lys Gln Glu Glu Gly Glu Ser
        195                 200

<210> SEQ ID NO 5
<211> LENGTH: 532
<212> TYPE: PRT
<213> ORGANISM: Homo sapiens

<400> SEQUENCE: 5

Met Ala Pro Ser Ser Pro Arg Pro Ala Leu Pro Ala Leu Leu Val Leu
1               5                   10                  15

Leu Gly Ala Leu Phe Pro Gly Pro Gly Asn Ala Gln Thr Ser Val Ser
            20                  25                  30

Pro Ser Lys Val Ile Leu Pro Arg Gly Gly Ser Val Leu Val Thr Cys
        35                  40                  45

Ser Thr Ser Cys Asp Gln Pro Lys Leu Leu Gly Ile Glu Thr Pro Leu
    50                  55                  60

Pro Lys Lys Glu Leu Leu Leu Pro Gly Asn Asn Arg Lys Val Tyr Glu
65                  70                  75                  80

Leu Ser Asn Val Gln Glu Asp Ser Gln Pro Met Cys Tyr Ser Asn Cys
                85                  90                  95

Pro Asp Gly Gln Ser Thr Ala Lys Thr Phe Leu Thr Val Tyr Trp Thr
            100                 105                 110

Pro Glu Arg Val Glu Leu Ala Pro Leu Pro Ser Trp Gln Pro Val Gly
        115                 120                 125

Lys Asn Leu Thr Leu Arg Cys Gln Val Glu Gly Gly Ala Pro Arg Ala
130                 135                 140

Asn Leu Thr Val Val Leu Leu Arg Gly Glu Lys Glu Leu Lys Arg Glu
145                 150                 155                 160

Pro Ala Val Gly Glu Pro Ala Glu Val Thr Thr Thr Val Leu Val Arg
                165                 170                 175

Arg Asp His His Gly Ala Asn Phe Ser Cys Arg Thr Glu Leu Asp Leu
            180                 185                 190

Arg Pro Gln Gly Leu Glu Leu Phe Glu Asn Thr Ser Ala Pro Tyr Gln
        195                 200                 205

Leu Gln Thr Phe Val Leu Pro Ala Thr Pro Pro Gln Leu Val Ser Pro
    210                 215                 220

Arg Val Leu Glu Val Asp Thr Gln Gly Thr Val Val Cys Ser Leu Asp
225                 230                 235                 240

Gly Leu Phe Pro Val Ser Glu Ala Gln Val His Leu Ala Leu Gly Asp
                245                 250                 255

Gln Arg Leu Asn Pro Thr Val Thr Tyr Gly Asn Asp Ser Phe Ser Ala
            260                 265                 270

Lys Ala Ser Val Ser Val Thr Ala Glu Asp Glu Gly Thr Gln Arg Leu
        275                 280                 285

Thr Cys Ala Val Ile Leu Gly Asn Gln Ser Gln Glu Thr Leu Gln Thr
    290                 295                 300

```
Val Thr Ile Tyr Ser Phe Pro Ala Pro Asn Val Ile Leu Thr Lys Pro
305                 310                 315                 320

Glu Val Ser Glu Gly Thr Glu Val Thr Val Lys Cys Glu Ala His Pro
                325                 330                 335

Arg Ala Lys Val Thr Leu Asn Gly Val Pro Ala Gln Pro Leu Gly Pro
            340                 345                 350

Arg Ala Gln Leu Leu Leu Lys Ala Thr Pro Glu Asp Asn Gly Arg Ser
        355                 360                 365

Phe Ser Cys Ser Ala Thr Leu Glu Val Ala Gly Gln Leu Ile His Lys
    370                 375                 380

Asn Gln Thr Arg Glu Leu Arg Val Leu Tyr Gly Pro Arg Leu Asp Glu
385                 390                 395                 400

Arg Asp Cys Pro Gly Asn Trp Thr Trp Pro Glu Asn Ser Gln Gln Thr
                405                 410                 415

Pro Met Cys Gln Ala Trp Gly Asn Pro Leu Pro Glu Leu Lys Cys Leu
            420                 425                 430

Lys Asp Gly Thr Phe Pro Leu Pro Ile Gly Glu Ser Val Thr Val Thr
        435                 440                 445

Arg Asp Leu Glu Gly Thr Tyr Leu Cys Arg Ala Arg Ser Thr Gln Gly
450                 455                 460

Glu Val Thr Arg Lys Val Thr Val Asn Val Leu Ser Pro Arg Tyr Glu
465                 470                 475                 480

Ile Val Ile Ile Thr Val Val Ala Ala Val Ile Met Gly Thr Ala
                485                 490                 495

Gly Leu Ser Thr Tyr Leu Tyr Asn Arg Gln Arg Lys Ile Lys Lys Tyr
            500                 505                 510

Arg Leu Gln Gln Ala Gln Lys Gly Thr Pro Met Lys Pro Asn Thr Gln
        515                 520                 525

Ala Thr Pro Pro
        530

<210> SEQ ID NO 6
<211> LENGTH: 1698
<212> TYPE: PRT
<213> ORGANISM: Homo sapiens

<400> SEQUENCE: 6

Met Arg Leu Leu Trp Gly Leu Ile Trp Ala Ser Ser Phe Phe Thr Leu
1               5                   10                  15

Ser Leu Gln Lys Pro Arg Leu Leu Leu Phe Ser Pro Ser Val Val His
            20                  25                  30

Leu Gly Val Pro Leu Ser Val Gly Val Gln Leu Gln Asp Val Pro Arg
        35                  40                  45

Gly Gln Val Val Lys Gly Ser Val Phe Leu Arg Asn Pro Ser Arg Asn
    50                  55                  60

Asn Val Pro Cys Ser Pro Lys Val Asp Phe Thr Leu Ser Ser Glu Arg
65                  70                  75                  80

Asp Phe Ala Leu Leu Ser Leu Gln Val Pro Leu Lys Asp Ala Lys Ser
                85                  90                  95

Cys Gly Leu His Gln Leu Leu Arg Gly Pro Glu Val Gln Leu Val Ala
            100                 105                 110

His Ser Pro Trp Leu Lys Asp Ser Leu Ser Arg Thr Thr Asn Ile Gln
        115                 120                 125

Gly Ile Asn Leu Leu Phe Ser Ser Arg Arg Gly His Leu Phe Leu Gln
    130                 135                 140
```

```
Thr Asp Gln Pro Ile Tyr Asn Pro Gly Gln Arg Val Arg Tyr Arg Val
145                 150                 155                 160

Phe Ala Leu Asp Gln Lys Met Arg Pro Ser Thr Asp Thr Ile Thr Val
            165                 170                 175

Met Val Glu Asn Ser His Gly Leu Arg Val Arg Lys Lys Glu Val Tyr
        180                 185                 190

Met Pro Ser Ser Ile Phe Gln Asp Asp Phe Val Ile Pro Asp Ile Ser
    195                 200                 205

Glu Pro Gly Thr Trp Lys Ile Ser Ala Arg Phe Ser Asp Gly Leu Glu
210                 215                 220

Ser Asn Ser Ser Thr Gln Phe Glu Val Lys Lys Tyr Val Leu Pro Asn
225                 230                 235                 240

Phe Glu Val Lys Ile Thr Pro Gly Lys Pro Tyr Ile Leu Thr Val Pro
                245                 250                 255

Gly His Leu Asp Glu Met Gln Leu Asp Ile Gln Ala Arg Tyr Ile Tyr
            260                 265                 270

Gly Lys Pro Val Gln Gly Val Ala Tyr Val Arg Phe Gly Leu Leu Asp
        275                 280                 285

Glu Asp Gly Lys Lys Thr Phe Phe Arg Gly Leu Glu Ser Gln Thr Lys
    290                 295                 300

Leu Val Asn Gly Gln Ser His Ile Ser Leu Ser Lys Ala Glu Phe Gln
305                 310                 315                 320

Asp Ala Leu Glu Lys Leu Asn Met Gly Ile Thr Asp Leu Gln Gly Leu
                325                 330                 335

Arg Leu Tyr Val Ala Ala Ala Ile Ile Glu Ser Pro Gly Gly Glu Met
            340                 345                 350

Glu Glu Ala Glu Leu Thr Ser Trp Tyr Phe Val Ser Ser Pro Phe Ser
        355                 360                 365

Leu Asp Leu Ser Lys Thr Lys Arg His Leu Val Pro Gly Ala Pro Phe
    370                 375                 380

Leu Leu Gln Ala Leu Val Arg Glu Met Ser Gly Ser Pro Ala Ser Gly
385                 390                 395                 400

Ile Pro Val Lys Val Ser Ala Thr Val Ser Ser Pro Gly Ser Val Pro
                405                 410                 415

Glu Val Gln Asp Ile Gln Gln Asn Thr Asp Gly Ser Gly Gln Val Ser
            420                 425                 430

Ile Pro Ile Ile Ile Pro Gln Thr Ile Ser Glu Leu Gln Leu Ser Val
        435                 440                 445

Ser Ala Gly Ser Pro His Pro Ala Ile Ala Arg Leu Thr Val Ala Ala
    450                 455                 460

Pro Pro Ser Gly Gly Pro Gly Phe Leu Ser Ile Glu Arg Pro Asp Ser
465                 470                 475                 480

Arg Pro Pro Arg Val Gly Asp Thr Leu Asn Leu Asn Leu Arg Ala Val
                485                 490                 495

Gly Ser Gly Ala Thr Phe Ser His Tyr Tyr Tyr Met Ile Leu Ser Arg
            500                 505                 510

Gly Gln Ile Val Phe Met Asn Arg Glu Pro Lys Arg Thr Leu Thr Ser
        515                 520                 525

Val Ser Val Phe Val Asp His His Leu Ala Pro Ser Phe Tyr Phe Val
    530                 535                 540

Ala Phe Tyr Tyr His Gly Asp His Pro Val Ala Asn Ser Leu Arg Val
545                 550                 555                 560
```

-continued

```
Asp Val Gln Ala Gly Ala Cys Glu Gly Lys Leu Glu Leu Ser Val Asp
                565                 570                 575
Gly Ala Lys Gln Tyr Arg Asn Gly Glu Ser Val Lys Leu His Leu Glu
            580                 585                 590
Thr Asp Ser Leu Ala Leu Val Ala Leu Gly Ala Leu Asp Thr Ala Leu
        595                 600                 605
Tyr Ala Ala Gly Ser Lys Ser His Lys Pro Leu Asn Met Gly Lys Val
    610                 615                 620
Phe Glu Ala Met Asn Ser Tyr Asp Leu Gly Cys Gly Pro Gly Gly Gly
625                 630                 635                 640
Asp Ser Ala Leu Gln Val Phe Gln Ala Ala Gly Leu Ala Phe Ser Asp
                645                 650                 655
Gly Asp Gln Trp Thr Leu Ser Arg Lys Arg Leu Ser Cys Pro Lys Glu
            660                 665                 670
Lys Thr Thr Arg Lys Lys Arg Asn Val Asn Phe Gln Lys Ala Ile Asn
        675                 680                 685
Glu Lys Leu Gly Gln Tyr Ala Ser Pro Thr Ala Lys Arg Cys Cys Gln
    690                 695                 700
Asp Gly Val Thr Arg Leu Pro Met Met Arg Ser Cys Glu Gln Arg Ala
705                 710                 715                 720
Ala Arg Val Gln Gln Pro Asp Cys Arg Glu Pro Phe Leu Ser Cys Cys
                725                 730                 735
Gln Phe Ala Glu Ser Leu Arg Lys Lys Ser Arg Asp Lys Gly Gln Ala
            740                 745                 750
Gly Leu Gln Arg Ala Leu Glu Ile Leu Gln Glu Glu Asp Leu Ile Asp
        755                 760                 765
Glu Asp Asp Ile Pro Val Arg Ser Phe Phe Pro Glu Asn Trp Leu Trp
    770                 775                 780
Arg Val Glu Thr Val Asp Arg Phe Gln Ile Leu Thr Leu Trp Leu Pro
785                 790                 795                 800
Asp Ser Leu Thr Thr Trp Glu Ile His Gly Leu Ser Leu Ser Lys Thr
                805                 810                 815
Lys Gly Leu Cys Val Ala Thr Pro Val Gln Leu Arg Val Phe Arg Glu
            820                 825                 830
Phe His Leu His Leu Arg Leu Pro Met Ser Val Arg Arg Phe Glu Gln
        835                 840                 845
Leu Glu Leu Arg Pro Val Leu Tyr Asn Tyr Leu Asp Lys Asn Leu Thr
    850                 855                 860
Val Ser Val His Val Ser Pro Val Glu Gly Leu Cys Leu Ala Gly Gly
865                 870                 875                 880
Gly Gly Leu Ala Gln Gln Val Leu Val Pro Ala Gly Ser Ala Arg Pro
                885                 890                 895
Val Ala Phe Ser Val Val Pro Thr Ala Ala Ala Val Ser Leu Lys
            900                 905                 910
Val Val Ala Arg Gly Ser Phe Glu Phe Pro Val Gly Asp Ala Val Ser
        915                 920                 925
Lys Val Leu Gln Ile Glu Lys Glu Gly Ala Ile His Arg Glu Glu Leu
    930                 935                 940
Val Tyr Glu Leu Asn Pro Leu Asp His Arg Gly Arg Thr Leu Glu Ile
945                 950                 955                 960
Pro Gly Asn Ser Asp Pro Asn Met Ile Pro Asp Gly Asp Phe Asn Ser
                965                 970                 975
Tyr Val Arg Val Thr Ala Ser Asp Pro Leu Asp Thr Leu Gly Ser Glu
```

-continued

```
                980             985             990
Gly Ala Leu Ser Pro Gly Gly Val Ala Ser Leu Leu Arg Leu Pro Arg
              995             1000            1005
Gly Cys Gly Glu Gln Thr Met Ile Tyr Leu Ala Pro Thr Leu Ala
    1010            1015            1020
Ala Ser Arg Tyr Leu Asp Lys Thr Glu Gln Trp Ser Thr Leu Pro
    1025            1030            1035
Pro Glu Thr Lys Asp His Ala Val Asp Leu Ile Gln Lys Gly Tyr
    1040            1045            1050
Met Arg Ile Gln Gln Phe Arg Lys Ala Asp Gly Ser Tyr Ala Ala
    1055            1060            1065
Trp Leu Ser Arg Asp Ser Ser Thr Trp Leu Thr Ala Phe Val Leu
    1070            1075            1080
Lys Val Leu Ser Leu Ala Gln Glu Gln Val Gly Gly Ser Pro Glu
    1085            1090            1095
Lys Leu Gln Glu Thr Ser Asn Trp Leu Leu Ser Gln Gln Gln Ala
    1100            1105            1110
Asp Gly Ser Phe Gln Asp Pro Cys Pro Val Leu Asp Arg Ser Met
    1115            1120            1125
Gln Gly Gly Leu Val Gly Asn Asp Glu Thr Val Ala Leu Thr Ala
    1130            1135            1140
Phe Val Thr Ile Ala Leu His His Gly Leu Ala Val Phe Gln Asp
    1145            1150            1155
Glu Gly Ala Glu Pro Leu Lys Gln Arg Val Glu Ala Ser Ile Ser
    1160            1165            1170
Lys Ala Asn Ser Phe Leu Gly Glu Lys Ala Ser Ala Gly Leu Leu
    1175            1180            1185
Gly Ala His Ala Ala Ala Ile Thr Ala Tyr Ala Leu Thr Leu Thr
    1190            1195            1200
Lys Ala Pro Val Asp Leu Leu Gly Val Ala His Asn Asn Leu Met
    1205            1210            1215
Ala Met Ala Gln Glu Thr Gly Asp Asn Leu Tyr Trp Gly Ser Val
    1220            1225            1230
Thr Gly Ser Gln Ser Asn Ala Val Ser Pro Thr Pro Ala Pro Arg
    1235            1240            1245
Asn Pro Ser Asp Pro Met Pro Gln Ala Pro Ala Leu Trp Ile Glu
    1250            1255            1260
Thr Thr Ala Tyr Ala Leu Leu His Leu Leu Leu His Glu Gly Lys
    1265            1270            1275
Ala Glu Met Ala Asp Gln Ala Ser Ala Trp Leu Thr Arg Gln Gly
    1280            1285            1290
Ser Phe Gln Gly Gly Phe Arg Ser Thr Gln Asp Thr Val Ile Ala
    1295            1300            1305
Leu Asp Ala Leu Ser Ala Tyr Trp Ile Ala Ser His Thr Thr Glu
    1310            1315            1320
Glu Arg Gly Leu Asn Val Thr Leu Ser Ser Thr Gly Arg Asn Gly
    1325            1330            1335
Phe Lys Ser His Ala Leu Gln Leu Asn Asn Arg Gln Ile Arg Gly
    1340            1345            1350
Leu Glu Glu Glu Leu Gln Phe Ser Leu Gly Ser Lys Ile Asn Val
    1355            1360            1365
Lys Val Gly Gly Asn Ser Lys Gly Thr Leu Lys Val Leu Arg Thr
    1370            1375            1380
```

```
Tyr Asn Val Leu Asp Met Lys Asn Thr Thr Cys Gln Asp Leu Gln
        1385                1390                1395

Ile Glu Val Thr Val Lys Gly His Val Glu Tyr Thr Met Glu Ala
    1400                1405                1410

Asn Glu Asp Tyr Glu Asp Tyr Glu Tyr Asp Glu Leu Pro Ala Lys
    1415                1420                1425

Asp Asp Pro Asp Ala Pro Leu Gln Pro Val Thr Pro Leu Gln Leu
    1430                1435                1440

Phe Glu Gly Arg Arg Asn Arg Arg Arg Glu Ala Pro Lys Leu
    1445                1450                1455

Thr Ser Leu Ser Asp Arg Tyr Val Ser His Phe Glu Thr Glu Gly
    1460                1465                1470

Pro His Val Leu Leu Tyr Phe Asp Ser Val Pro Thr Ser Arg Glu
    1475                1480                1485

Cys Val Gly Phe Glu Ala Val Gln Glu Val Pro Val Gly Leu Val
    1490                1495                1500

Gln Pro Ala Ser Ala Thr Leu Tyr Asp Tyr Tyr Asn Pro Glu Arg
    1505                1510                1515

Arg Cys Ser Val Phe Tyr Gly Ala Pro Ser Lys Ser Arg Leu Leu
    1520                1525                1530

Ala Thr Leu Cys Ser Ala Glu Val Cys Gln Cys Ala Glu Gly Lys
    1535                1540                1545

Cys Pro Arg Gln Arg Arg Ala Leu Glu Arg Gly Leu Gln Asp Glu
    1550                1555                1560

Asp Gly Tyr Arg Met Lys Phe Ala Cys Tyr Tyr Pro Arg Val Glu
    1565                1570                1575

Tyr Gly Phe Gln Val Lys Val Leu Arg Glu Asp Ser Arg Ala Ala
    1580                1585                1590

Phe Arg Leu Phe Glu Thr Lys Ile Thr Gln Val Leu His Phe Thr
    1595                1600                1605

Lys Asp Val Lys Ala Ala Ala Asn Gln Met Arg Asn Phe Leu Val
    1610                1615                1620

Arg Ala Ser Cys Arg Leu Arg Leu Glu Pro Gly Lys Glu Tyr Leu
    1625                1630                1635

Ile Met Gly Leu Asp Gly Ala Thr Tyr Asp Leu Glu Gly His Pro
    1640                1645                1650

Gln Tyr Leu Leu Asp Ser Asn Ser Trp Ile Glu Glu Met Pro Ser
    1655                1660                1665

Glu Arg Leu Cys Arg Ser Thr Arg Gln Arg Ala Ala Cys Ala Gln
    1670                1675                1680

Leu Asn Asp Phe Leu Gln Glu Tyr Gly Thr Gln Gly Cys Gln Val
    1685                1690                1695

<210> SEQ ID NO 7
<211> LENGTH: 418
<212> TYPE: PRT
<213> ORGANISM: Homo sapiens

<400> SEQUENCE: 7

Met Gln Ala Leu Val Leu Leu Leu Cys Ile Gly Ala Leu Leu Gly His
1               5                   10                  15

Ser Ser Cys Gln Asn Pro Ala Ser Pro Pro Glu Glu Gly Ser Pro Asp
                20                  25                  30

Pro Asp Ser Thr Gly Ala Leu Val Glu Glu Glu Asp Pro Phe Phe Lys
```

```
            35                  40                  45
Val Pro Val Asn Lys Leu Ala Ala Val Ser Asn Phe Gly Tyr Asp
 50                  55                  60

Leu Tyr Arg Val Arg Ser Ser Thr Pro Thr Thr Asn Val Leu Leu
 65                  70                  75                  80

Ser Pro Leu Ser Val Ala Thr Ala Leu Ser Ala Leu Ser Leu Gly Ala
                 85                  90                  95

Glu Gln Arg Thr Glu Ser Ile Ile His Arg Ala Leu Tyr Tyr Asp Leu
                100                 105                 110

Ile Ser Ser Pro Asp Ile His Gly Thr Tyr Lys Glu Leu Leu Asp Thr
            115                 120                 125

Val Thr Ala Pro Gln Lys Asn Leu Lys Ser Ala Ser Arg Ile Val Phe
130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
            180                 185                 190

Ala Arg Ser Thr Lys Glu Ile Pro Asp Glu Ile Ser Ile Leu Leu Leu
            195                 200                 205

Gly Val Ala His Phe Lys Gly Gln Trp Val Thr Lys Phe Asp Ser Arg
210                 215                 220

Lys Thr Ser Leu Glu Asp Phe Tyr Leu Asp Glu Glu Arg Thr Val Arg
225                 230                 235                 240

Val Pro Met Met Ser Asp Pro Lys Ala Val Leu Arg Tyr Gly Leu Asp
                245                 250                 255

Ser Asp Leu Ser Cys Lys Ile Ala Gln Leu Pro Leu Thr Gly Ser Met
                260                 265                 270

Ser Ile Ile Phe Phe Leu Pro Leu Lys Val Thr Gln Asn Leu Thr Leu
            275                 280                 285

Ile Glu Glu Ser Leu Thr Ser Glu Phe Ile His Asp Ile Asp Arg Glu
            290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
                340                 345                 350

Leu Thr Gln Val Glu His Arg Ala Gly Phe Glu Trp Asn Glu Asp Gly
            355                 360                 365

Ala Gly Thr Thr Pro Ser Pro Gly Leu Gln Pro Ala His Leu Thr Phe
            370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro

<210> SEQ ID NO 8
<211> LENGTH: 418
<212> TYPE: PRT
<213> ORGANISM: Homo sapiens
```

-continued

<400> SEQUENCE: 8

```
Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
    290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
        355                 360                 365

Thr Glu Ala Ala Gly Ala Met Phe Leu Glu Ala Ile Pro Met Ser Ile
    370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415
```

Gln Lys

<210> SEQ ID NO 9
<211> LENGTH: 91
<212> TYPE: PRT
<213> ORGANISM: Homo sapiens

<400> SEQUENCE: 9

Met Lys Val Ser Ala Ala Ala Leu Ala Val Ile Leu Ile Ala Thr Ala
1               5                   10                  15

Leu Cys Ala Pro Ala Ser Ala Ser Pro Tyr Ser Ser Asp Thr Thr Pro
                20                  25                  30

Cys Cys Phe Ala Tyr Ile Ala Arg Pro Leu Pro Arg Ala His Ile Lys
            35                  40                  45

Glu Tyr Phe Tyr Thr Ser Gly Lys Cys Ser Asn Pro Ala Val Val Phe
50                  55                  60

Val Thr Arg Lys Asn Arg Gln Val Cys Ala Asn Pro Glu Lys Lys Trp
65                  70                  75                  80

Val Arg Glu Tyr Ile Asn Ser Leu Glu Met Ser
                85                  90

<210> SEQ ID NO 10
<211> LENGTH: 99
<212> TYPE: PRT
<213> ORGANISM: Homo sapiens

<400> SEQUENCE: 10

Met Gln Pro Arg Val Leu Leu Val Val Ala Leu Leu Ala Leu Leu Ala
1               5                   10                  15

Ser Ala Arg Ala Ser Glu Ala Glu Asp Ala Ser Leu Leu Ser Phe Met
                20                  25                  30

Gln Gly Tyr Met Lys His Ala Thr Lys Thr Ala Lys Asp Ala Leu Ser
            35                  40                  45

Ser Val Gln Glu Ser Gln Val Ala Gln Gln Ala Arg Gly Trp Val Thr
50                  55                  60

Asp Gly Phe Ser Ser Leu Lys Asp Tyr Trp Ser Thr Val Lys Asp Lys
65                  70                  75                  80

Phe Ser Glu Phe Trp Asp Leu Asp Pro Glu Val Arg Pro Thr Ser Ala
                85                  90                  95

Val Ala Ala

<210> SEQ ID NO 11
<211> LENGTH: 402
<212> TYPE: PRT
<213> ORGANISM: Homo sapiens

<400> SEQUENCE: 11

Met Gln Met Ser Pro Ala Leu Thr Cys Leu Val Leu Gly Leu Ala Leu
1               5                   10                  15

Val Phe Gly Glu Gly Ser Ala Val His His Pro Ser Tyr Val Ala
                20                  25                  30

His Leu Ala Ser Asp Phe Gly Val Arg Val Phe Gln Gln Val Ala Gln
            35                  40                  45

Ala Ser Lys Asp Arg Asn Val Val Phe Ser Pro Tyr Gly Val Ala Ser
50                  55                  60

Val Leu Ala Met Leu Gln Leu Thr Thr Gly Gly Glu Thr Gln Gln Gln
65                  70                  75                  80

```
Ile Gln Ala Ala Met Gly Phe Lys Ile Asp Asp Lys Gly Met Ala Pro
                85                  90                  95

Ala Leu Arg His Leu Tyr Lys Glu Leu Met Gly Pro Trp Asn Lys Asp
            100                 105                 110

Glu Ile Ser Thr Thr Asp Ala Ile Phe Val Gln Arg Asp Leu Lys Leu
        115                 120                 125

Val Gln Gly Phe Met Pro His Phe Arg Leu Phe Arg Ser Thr Val
    130                 135                 140

Lys Gln Val Asp Phe Ser Glu Val Glu Arg Ala Arg Phe Ile Ile Asn
145                 150                 155                 160

Asp Trp Val Lys Thr His Thr Lys Gly Met Ile Ser Asn Leu Leu Gly
                165                 170                 175

Lys Gly Ala Val Asp Gln Leu Thr Arg Leu Val Leu Val Asn Ala Leu
            180                 185                 190

Tyr Phe Asn Gly Gln Trp Lys Thr Pro Phe Pro Asp Ser Ser Thr His
        195                 200                 205

Arg Arg Leu Phe His Lys Ser Asp Gly Ser Thr Val Ser Val Pro Met
    210                 215                 220

Met Ala Gln Thr Asn Lys Phe Asn Tyr Thr Glu Phe Thr Thr Pro Asp
225                 230                 235                 240

Gly His Tyr Tyr Asp Ile Leu Glu Leu Pro Tyr His Gly Asp Thr Leu
                245                 250                 255

Ser Met Phe Ile Ala Ala Pro Tyr Glu Lys Glu Val Pro Leu Ser Ala
            260                 265                 270

Leu Thr Asn Ile Leu Ser Ala Gln Leu Ile Ser His Trp Lys Gly Asn
        275                 280                 285

Met Thr Arg Leu Pro Arg Leu Leu Val Leu Pro Lys Phe Ser Leu Glu
    290                 295                 300

Thr Glu Val Asp Leu Arg Lys Pro Leu Glu Asn Leu Gly Met Thr Asp
305                 310                 315                 320

Met Phe Arg Gln Phe Gln Ala Asp Phe Thr Ser Leu Ser Asp Gln Glu
                325                 330                 335

Pro Leu His Val Ala Gln Ala Leu Gln Lys Val Lys Ile Glu Val Asn
            340                 345                 350

Glu Ser Gly Thr Val Ala Ser Ser Thr Ala Val Ile Val Ser Ala
        355                 360                 365

Arg Met Ala Pro Glu Glu Ile Ile Met Asp Arg Pro Phe Leu Phe Val
    370                 375                 380

Val Arg His Asn Pro Thr Gly Thr Val Leu Phe Met Gly Gln Val Met
385                 390                 395                 400

Glu Pro

<210> SEQ ID NO 12
<211> LENGTH: 224
<212> TYPE: PRT
<213> ORGANISM: Homo sapiens

<400> SEQUENCE: 12

Met Glu Lys Leu Leu Cys Phe Leu Val Leu Thr Ser Leu Ser His Ala
1               5                   10                  15

Phe Gly Gln Thr Asp Met Ser Arg Lys Ala Phe Val Phe Pro Lys Glu
            20                  25                  30

Ser Asp Thr Ser Tyr Val Ser Leu Lys Ala Pro Leu Thr Lys Pro Leu
        35                  40                  45
```

```
Lys Ala Phe Thr Val Cys Leu His Phe Tyr Thr Glu Leu Ser Ser Thr
 50                  55                  60

Arg Gly Tyr Ser Ile Phe Ser Tyr Ala Thr Lys Arg Gln Asp Asn Glu
 65                      70                  75                  80

Ile Leu Ile Phe Trp Ser Lys Asp Ile Gly Tyr Ser Phe Thr Val Gly
                     85                  90                  95

Gly Ser Glu Ile Leu Phe Glu Val Pro Glu Val Thr Val Ala Pro Val
                100                 105                 110

His Ile Cys Thr Ser Trp Glu Ser Ala Ser Gly Ile Val Glu Phe Trp
                115                 120                 125

Val Asp Gly Lys Pro Arg Val Arg Lys Ser Leu Lys Lys Gly Tyr Thr
130                 135                 140

Val Gly Ala Glu Ala Ser Ile Ile Leu Gly Gln Glu Gln Asp Ser Phe
145                 150                 155                 160

Gly Gly Asn Phe Glu Gly Ser Gln Ser Leu Val Gly Asp Ile Gly Asn
                165                 170                 175

Val Asn Met Trp Asp Phe Val Leu Ser Pro Asp Glu Ile Asn Thr Ile
                180                 185                 190

Tyr Leu Gly Gly Pro Phe Ser Pro Asn Val Leu Asn Trp Arg Ala Leu
                195                 200                 205

Lys Tyr Glu Val Gln Gly Glu Val Phe Thr Lys Pro Gln Leu Trp Pro
210                 215                 220

<210> SEQ ID NO 13
<211> LENGTH: 412
<212> TYPE: PRT
<213> ORGANISM: Homo sapiens

<400> SEQUENCE: 13

Met Gln Pro Ser Ser Leu Leu Pro Leu Ala Leu Cys Leu Leu Ala Ala
 1               5                  10                  15

Pro Ala Ser Ala Leu Val Arg Ile Pro Leu His Lys Phe Thr Ser Ile
                 20                  25                  30

Arg Arg Thr Met Ser Glu Val Gly Gly Ser Val Glu Asp Leu Ile Ala
                 35                  40                  45

Lys Gly Pro Val Ser Lys Tyr Ser Gln Ala Val Pro Ala Val Thr Glu
 50                  55                  60

Gly Pro Ile Pro Glu Val Leu Lys Asn Tyr Met Asp Ala Gln Tyr Tyr
 65                  70                  75                  80

Gly Glu Ile Gly Ile Gly Thr Pro Pro Gln Cys Phe Thr Val Val Phe
                 85                  90                  95

Asp Thr Gly Ser Ser Asn Leu Trp Val Pro Ser Ile His Cys Lys Leu
                100                 105                 110

Leu Asp Ile Ala Cys Trp Ile His His Lys Tyr Asn Ser Asp Lys Ser
                115                 120                 125

Ser Thr Tyr Val Lys Asn Gly Thr Ser Phe Asp Ile His Tyr Gly Ser
130                 135                 140

Gly Ser Leu Ser Gly Tyr Leu Ser Gln Asp Thr Val Ser Val Pro Cys
145                 150                 155                 160

Gln Ser Ala Ser Ser Ala Ser Ala Leu Gly Gly Val Lys Val Glu Arg
                165                 170                 175

Gln Val Phe Gly Glu Ala Thr Lys Gln Pro Gly Ile Thr Phe Ile Ala
                180                 185                 190

Ala Lys Phe Asp Gly Ile Leu Gly Met Ala Tyr Pro Arg Ile Ser Val
```

```
                    195                 200                 205
Asn Asn Val Leu Pro Val Phe Asp Asn Leu Met Gln Gln Lys Leu Val
210                 215                 220

Asp Gln Asn Ile Phe Ser Phe Tyr Leu Ser Arg Asp Pro Asp Ala Gln
225                 230                 235                 240

Pro Gly Gly Glu Leu Met Leu Gly Gly Thr Asp Ser Lys Tyr Tyr Lys
                    245                 250                 255

Gly Ser Leu Ser Tyr Leu Asn Val Thr Arg Lys Ala Tyr Trp Gln Val
                260                 265                 270

His Leu Asp Gln Val Glu Val Ala Ser Gly Leu Thr Leu Cys Lys Glu
            275                 280                 285

Gly Cys Glu Ala Ile Val Asp Thr Gly Thr Ser Leu Met Val Gly Pro
        290                 295                 300

Val Asp Glu Val Arg Glu Leu Gln Lys Ala Ile Gly Ala Val Pro Leu
305                 310                 315                 320

Ile Gln Gly Glu Tyr Met Ile Pro Cys Glu Lys Val Ser Thr Leu Pro
                    325                 330                 335

Ala Ile Thr Leu Lys Leu Gly Gly Lys Gly Tyr Lys Leu Ser Pro Glu
                340                 345                 350

Asp Tyr Thr Leu Lys Val Ser Gln Ala Gly Lys Thr Leu Cys Leu Ser
            355                 360                 365

Gly Phe Met Gly Met Asp Ile Pro Pro Pro Ser Gly Pro Leu Trp Ile
        370                 375                 380

Leu Gly Asp Val Phe Ile Gly Arg Tyr Tyr Thr Val Phe Asp Arg Asp
385                 390                 395                 400

Asn Asn Arg Val Gly Phe Ala Glu Ala Arg Leu
                    405                 410

<210> SEQ ID NO 14
<211> LENGTH: 317
<212> TYPE: PRT
<213> ORGANISM: Homo sapiens

<400> SEQUENCE: 14

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
        115                 120                 125

Val Cys Gly Arg Leu Val Gln Tyr Arg Gly Glu Val Gln Ala Met Leu
    130                 135                 140

Gly Gln Ser Thr Glu Glu Leu Arg Val Arg Leu Ala Ser His Leu Arg
145                 150                 155                 160
```

-continued

```
Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
            195                 200                 205

Arg Ala Ala Thr Val Gly Ser Leu Ala Gly Gln Pro Leu Gln Glu Arg
        210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
            260                 265                 270

Glu Ala Phe Gln Ala Arg Leu Lys Ser Trp Phe Glu Pro Leu Val Glu
            275                 280                 285

Asp Met Gln Arg Gln Trp Ala Gly Leu Val Glu Lys Val Gln Ala Ala
        290                 295                 300

Val Gly Thr Ser Ala Ala Pro Val Pro Ser Asp Asn His
305                 310                 315
```

<210> SEQ ID NO 15
<211> LENGTH: 1474
<212> TYPE: PRT
<213> ORGANISM: Homo sapiens

<400> SEQUENCE: 15

```
Met Gly Lys Asn Lys Leu Leu His Pro Ser Leu Val Leu Leu Leu Leu
1               5                   10                  15

Val Leu Leu Pro Thr Asp Ala Ser Val Ser Gly Lys Pro Gln Tyr Met
            20                  25                  30

Val Leu Val Pro Ser Leu Leu His Thr Glu Thr Thr Glu Lys Gly Cys
        35                  40                  45

Val Leu Leu Ser Tyr Leu Asn Glu Thr Val Thr Val Ser Ala Ser Leu
    50                  55                  60

Glu Ser Val Arg Gly Asn Arg Ser Leu Phe Thr Asp Leu Glu Ala Glu
65                  70                  75                  80

Asn Asp Val Leu His Cys Val Ala Phe Ala Val Pro Lys Ser Ser Ser
                85                  90                  95

Asn Glu Glu Val Met Phe Leu Thr Val Gln Val Lys Gly Pro Thr Gln
            100                 105                 110

Glu Phe Lys Lys Arg Thr Thr Val Met Val Lys Asn Glu Asp Ser Leu
        115                 120                 125

Val Phe Val Gln Thr Asp Lys Ser Ile Tyr Lys Pro Gly Gln Thr Val
    130                 135                 140

Lys Phe Arg Val Val Ser Met Asp Glu Asn Phe His Pro Leu Asn Glu
145                 150                 155                 160

Leu Ile Pro Leu Val Tyr Ile Gln Asp Pro Lys Gly Asn Arg Ile Ala
                165                 170                 175

Gln Trp Gln Ser Phe Gln Leu Glu Gly Gly Leu Lys Gln Phe Ser Phe
            180                 185                 190

Pro Leu Ser Ser Glu Pro Phe Gln Gly Ser Tyr Lys Val Val Val Gln
        195                 200                 205

Lys Lys Ser Gly Gly Arg Thr Glu His Pro Phe Thr Val Glu Glu Phe
    210                 215                 220
```

```
Val Leu Pro Lys Phe Glu Val Gln Val Thr Val Pro Lys Ile Ile Thr
225                 230                 235                 240

Ile Leu Glu Glu Glu Met Asn Val Ser Val Cys Gly Leu Tyr Thr Tyr
                245                 250                 255

Gly Lys Pro Val Pro Gly His Val Thr Val Ser Ile Cys Arg Lys Tyr
                260                 265                 270

Ser Asp Ala Ser Asp Cys His Gly Glu Asp Ser Gln Ala Phe Cys Glu
            275                 280                 285

Lys Phe Ser Gly Gln Leu Asn Ser His Gly Cys Phe Tyr Gln Gln Val
290                 295                 300

Lys Thr Lys Val Phe Gln Leu Lys Arg Lys Glu Tyr Glu Met Lys Leu
305                 310                 315                 320

His Thr Glu Ala Gln Ile Gln Glu Gly Thr Val Val Glu Leu Thr
                325                 330                 335

Gly Arg Gln Ser Ser Glu Ile Thr Arg Thr Ile Thr Lys Leu Ser Phe
            340                 345                 350

Val Lys Val Asp Ser His Phe Arg Gln Gly Ile Pro Phe Phe Gly Gln
            355                 360                 365

Val Arg Leu Val Asp Gly Lys Gly Val Pro Ile Pro Asn Lys Val Ile
370                 375                 380

Phe Ile Arg Gly Asn Glu Ala Asn Tyr Tyr Ser Asn Ala Thr Thr Asp
385                 390                 395                 400

Glu His Gly Leu Val Gln Phe Ser Ile Asn Thr Thr Asn Val Met Gly
                405                 410                 415

Thr Ser Leu Thr Val Arg Val Asn Tyr Lys Asp Arg Ser Pro Cys Tyr
                420                 425                 430

Gly Tyr Gln Trp Val Ser Glu Glu His Glu Glu Ala His His Thr Ala
            435                 440                 445

Tyr Leu Val Phe Ser Pro Ser Lys Ser Phe Val His Leu Glu Pro Met
450                 455                 460

Ser His Glu Leu Pro Cys Gly His Thr Gln Thr Val Gln Ala His Tyr
465                 470                 475                 480

Ile Leu Asn Gly Gly Thr Leu Leu Gly Leu Lys Lys Leu Ser Phe Tyr
                485                 490                 495

Tyr Leu Ile Met Ala Lys Gly Gly Ile Val Arg Thr Gly Thr His Gly
                500                 505                 510

Leu Leu Val Lys Gln Glu Asp Met Lys Gly His Phe Ser Ile Ser Ile
            515                 520                 525

Pro Val Lys Ser Asp Ile Ala Pro Val Ala Arg Leu Leu Ile Tyr Ala
530                 535                 540

Val Leu Pro Thr Gly Asp Val Ile Gly Asp Ser Ala Lys Tyr Asp Val
545                 550                 555                 560

Glu Asn Cys Leu Ala Asn Lys Val Asp Leu Ser Phe Ser Pro Ser Gln
                565                 570                 575

Ser Leu Pro Ala Ser His Ala His Leu Arg Val Thr Ala Ala Pro Gln
                580                 585                 590

Ser Val Cys Ala Leu Arg Ala Val Asp Gln Ser Val Leu Leu Met Lys
            595                 600                 605

Pro Asp Ala Glu Leu Ser Ala Ser Ser Val Tyr Asn Leu Leu Pro Glu
610                 615                 620

Lys Asp Leu Thr Gly Phe Pro Gly Pro Leu Asn Asp Gln Asp Asp Glu
625                 630                 635                 640
```

```
Asp Cys Ile Asn Arg His Asn Val Tyr Ile Asn Gly Ile Thr Tyr Thr
                645                 650                 655

Pro Val Ser Ser Thr Asn Glu Lys Asp Met Tyr Ser Phe Leu Glu Asp
            660                 665                 670

Met Gly Leu Lys Ala Phe Thr Asn Ser Lys Ile Arg Lys Pro Lys Met
        675                 680                 685

Cys Pro Gln Leu Gln Gln Tyr Glu Met His Gly Pro Glu Gly Leu Arg
    690                 695                 700

Val Gly Phe Tyr Glu Ser Asp Val Met Gly Arg Gly His Ala Arg Leu
705                 710                 715                 720

Val His Val Glu Glu Pro His Thr Glu Thr Val Arg Lys Tyr Phe Pro
                725                 730                 735

Glu Thr Trp Ile Trp Asp Leu Val Val Asn Ser Ala Gly Val Ala
            740                 745                 750

Glu Val Gly Val Thr Val Pro Asp Thr Ile Thr Glu Trp Lys Ala Gly
        755                 760                 765

Ala Phe Cys Leu Ser Glu Asp Ala Gly Leu Gly Ile Ser Ser Thr Ala
    770                 775                 780

Ser Leu Arg Ala Phe Gln Pro Phe Val Glu Leu Thr Met Pro Tyr
785             790                 795                 800

Ser Val Ile Arg Gly Glu Ala Phe Thr Leu Lys Ala Thr Val Leu Asn
                805                 810                 815

Tyr Leu Pro Lys Cys Ile Arg Val Ser Val Gln Leu Glu Ala Ser Pro
            820                 825                 830

Ala Phe Leu Ala Val Pro Val Glu Lys Glu Gln Ala Pro His Cys Ile
        835                 840                 845

Cys Ala Asn Gly Arg Gln Thr Val Ser Trp Ala Val Thr Pro Lys Ser
    850                 855                 860

Leu Gly Asn Val Asn Phe Thr Val Ser Ala Glu Ala Leu Glu Ser Gln
865                 870                 875                 880

Glu Leu Cys Gly Thr Glu Val Pro Ser Val Pro Glu His Gly Arg Lys
                885                 890                 895

Asp Thr Val Ile Lys Pro Leu Leu Val Glu Pro Glu Gly Leu Glu Lys
            900                 905                 910

Glu Thr Thr Phe Asn Ser Leu Leu Cys Pro Ser Gly Gly Glu Val Ser
        915                 920                 925

Glu Glu Leu Ser Leu Lys Leu Pro Pro Asn Val Val Glu Glu Ser Ala
    930                 935                 940

Arg Ala Ser Val Ser Val Leu Gly Asp Ile Leu Gly Ser Ala Met Gln
945                 950                 955                 960

Asn Thr Gln Asn Leu Leu Gln Met Pro Tyr Gly Cys Gly Glu Gln Asn
                965                 970                 975

Met Val Leu Phe Ala Pro Asn Ile Tyr Val Leu Asp Tyr Leu Asn Glu
            980                 985                 990

Thr Gln Gln Leu Thr Pro Glu Ile Lys Ser Lys Ala Ile Gly Tyr Leu
        995                 1000                1005

Asn Thr Gly Tyr Gln Arg Gln Leu Asn Tyr Lys His Tyr Asp Gly
    1010                1015                1020

Ser Tyr Ser Thr Phe Gly Glu Arg Tyr Gly Arg Asn Gln Gly Asn
    1025                1030                1035

Thr Trp Leu Thr Ala Phe Val Leu Lys Thr Phe Ala Gln Ala Arg
    1040                1045                1050

Ala Tyr Ile Phe Ile Asp Glu Ala His Ile Thr Gln Ala Leu Ile
```

```
            1055                1060                1065

Trp Leu Ser Gln Arg Gln Lys Asp Asn Gly Cys Phe Arg Ser Ser
        1070                1075                1080

Gly Ser Leu Leu Asn Asn Ala Ile Lys Gly Val Glu Asp Glu
        1085                1090                1095

Val Thr Leu Ser Ala Tyr Ile Thr Ile Ala Leu Leu Glu Ile Pro
        1100                1105                1110

Leu Thr Val Thr His Pro Val Val Arg Asn Ala Leu Phe Cys Leu
        1115                1120                1125

Glu Ser Ala Trp Lys Thr Ala Gln Glu Gly Asp His Gly Ser His
        1130                1135                1140

Val Tyr Thr Lys Ala Leu Leu Ala Tyr Ala Phe Ala Leu Ala Gly
        1145                1150                1155

Asn Gln Asp Lys Arg Lys Glu Val Leu Lys Ser Leu Asn Glu Glu
        1160                1165                1170

Ala Val Lys Lys Asp Asn Ser Val His Trp Glu Arg Pro Gln Lys
        1175                1180                1185

Pro Lys Ala Pro Val Gly His Phe Tyr Glu Pro Gln Ala Pro Ser
        1190                1195                1200

Ala Glu Val Glu Met Thr Ser Tyr Val Leu Leu Ala Tyr Leu Thr
        1205                1210                1215

Ala Gln Pro Ala Pro Thr Ser Glu Asp Leu Thr Ser Ala Thr Asn
        1220                1225                1230

Ile Val Lys Trp Ile Thr Lys Gln Gln Asn Ala Gln Gly Gly Phe
        1235                1240                1245

Ser Ser Thr Gln Asp Thr Val Val Ala Leu His Ala Leu Ser Lys
        1250                1255                1260

Tyr Gly Ala Ala Thr Phe Thr Arg Thr Gly Lys Ala Ala Gln Val
        1265                1270                1275

Thr Ile Gln Ser Ser Gly Thr Phe Ser Ser Lys Phe Gln Val Asp
        1280                1285                1290

Asn Asn Asn Arg Leu Leu Leu Gln Gln Val Ser Leu Pro Glu Leu
        1295                1300                1305

Pro Gly Glu Tyr Ser Met Lys Val Thr Gly Glu Gly Cys Val Tyr
        1310                1315                1320

Leu Gln Thr Ser Leu Lys Tyr Asn Ile Leu Pro Glu Lys Glu Glu
        1325                1330                1335

Phe Pro Phe Ala Leu Gly Val Gln Thr Leu Pro Gln Thr Cys Asp
        1340                1345                1350

Glu Pro Lys Ala His Thr Ser Phe Gln Ile Ser Leu Ser Val Ser
        1355                1360                1365

Tyr Thr Gly Ser Arg Ser Ala Ser Asn Met Ala Ile Val Asp Val
        1370                1375                1380

Lys Met Val Ser Gly Phe Ile Pro Leu Lys Pro Thr Val Lys Met
        1385                1390                1395

Leu Glu Arg Ser Asn His Val Ser Arg Thr Glu Val Ser Ser Asn
        1400                1405                1410

His Val Leu Ile Tyr Leu Asp Lys Val Ser Asn Gln Thr Leu Ser
        1415                1420                1425

Leu Phe Phe Thr Val Leu Gln Asp Val Pro Val Arg Asp Leu Lys
        1430                1435                1440

Pro Ala Ile Val Lys Val Tyr Asp Tyr Tyr Glu Thr Asp Glu Phe
        1445                1450                1455
```

Ala Ile Ala Glu Tyr Asn Ala Pro Cys Ser Lys Asp Leu Gly Asn
    1460                1465                1470

Ala

<210> SEQ ID NO 16
<211> LENGTH: 223
<212> TYPE: PRT
<213> ORGANISM: Homo sapiens

<400> SEQUENCE: 16

Met Asn Lys Pro Leu Leu Trp Ile Ser Val Leu Thr Ser Leu Leu Glu
1               5                   10                  15

Ala Phe Ala His Thr Asp Leu Ser Gly Lys Val Phe Val Phe Pro Arg
                20                  25                  30

Glu Ser Val Thr Asp His Val Asn Leu Ile Thr Pro Leu Glu Lys Pro
            35                  40                  45

Leu Gln Asn Phe Thr Leu Cys Phe Arg Ala Tyr Ser Asp Leu Ser Arg
        50                  55                  60

Ala Tyr Ser Leu Phe Ser Tyr Asn Thr Gln Gly Arg Asp Asn Glu Leu
65                  70                  75                  80

Leu Val Tyr Lys Glu Arg Val Gly Glu Tyr Ser Leu Tyr Ile Gly Arg
                85                  90                  95

His Lys Val Thr Ser Lys Val Ile Glu Lys Phe Pro Ala Pro Val His
            100                 105                 110

Ile Cys Val Ser Trp Glu Ser Ser Gly Ile Ala Glu Phe Trp Ile
        115                 120                 125

Asn Gly Thr Pro Leu Val Lys Lys Gly Leu Arg Gln Gly Tyr Phe Val
130                 135                 140

Glu Ala Gln Pro Lys Ile Val Leu Gly Gln Gln Asp Ser Tyr Gly Gly
145                 150                 155                 160

Gly Lys Phe Asp Arg Ser Gln Ser Phe Val Gly Glu Ile Gly Asp Leu
                165                 170                 175

Tyr Met Trp Asp Ser Val Leu Pro Pro Glu Asn Ile Leu Ser Ala Tyr
            180                 185                 190

Gln Gly Thr Pro Leu Pro Ala Asn Ile Leu Asp Trp Gln Ala Leu Asn
        195                 200                 205

Tyr Glu Ile Arg Gly Tyr Val Ile Ile Lys Pro Leu Val Trp Val
    210                 215                 220

<210> SEQ ID NO 17
<211> LENGTH: 434
<212> TYPE: PRT
<213> ORGANISM: Homo sapiens

<400> SEQUENCE: 17

Met Ser Ile Glu Lys Ile Trp Ala Arg Glu Ile Leu Asp Ser Arg Gly
1               5                   10                  15

Asn Pro Thr Val Glu Val Asp Leu Tyr Thr Ala Lys Gly Leu Phe Arg
                20                  25                  30

Ala Ala Val Pro Ser Gly Ala Ser Thr Gly Ile Tyr Glu Ala Leu Glu
            35                  40                  45

Leu Arg Asp Gly Asp Lys Gln Arg Tyr Leu Gly Lys Gly Val Leu Lys
        50                  55                  60

Ala Val Asp His Ile Asn Ser Thr Ile Ala Pro Ala Leu Ile Ser Ser
65                  70                  75                  80

```
Gly Leu Ser Val Val Glu Gln Glu Lys Leu Asp Asn Leu Met Leu Glu
                85                  90                  95

Leu Asp Gly Thr Glu Asn Lys Ser Lys Phe Gly Ala Asn Ala Ile Leu
            100                 105                 110

Gly Val Ser Leu Ala Val Cys Lys Ala Gly Ala Ala Glu Arg Glu Leu
        115                 120                 125

Pro Leu Tyr Arg His Ile Ala Gln Leu Ala Gly Asn Ser Asp Leu Ile
    130                 135                 140

Leu Pro Val Pro Ala Phe Asn Val Ile Asn Gly Ser His Ala Gly
145                 150                 155                 160

Asn Lys Leu Ala Met Gln Glu Phe Met Ile Leu Pro Val Gly Ala Glu
                165                 170                 175

Ser Phe Arg Asp Ala Met Arg Leu Gly Ala Glu Val Tyr His Thr Leu
                180                 185                 190

Lys Gly Val Ile Lys Asp Lys Tyr Gly Lys Asp Ala Thr Asn Val Gly
            195                 200                 205

Asp Glu Gly Gly Phe Ala Pro Asn Ile Leu Glu Asn Ser Glu Ala Leu
        210                 215                 220

Glu Leu Val Lys Glu Ala Ile Asp Lys Ala Gly Tyr Thr Glu Lys Ile
225                 230                 235                 240

Val Ile Gly Met Asp Val Ala Ala Ser Glu Phe Tyr Arg Asp Gly Lys
                245                 250                 255

Tyr Asp Leu Asp Phe Lys Ser Pro Thr Asp Pro Ser Arg Tyr Ile Thr
                260                 265                 270

Gly Asp Gln Leu Gly Ala Leu Tyr Gln Asp Phe Val Arg Asp Tyr Pro
            275                 280                 285

Val Val Ser Ile Glu Asp Pro Phe Asp Gln Asp Asp Trp Ala Ala Trp
290                 295                 300

Ser Lys Phe Thr Ala Asn Val Gly Ile Gln Ile Val Gly Asp Asp Leu
305                 310                 315                 320

Thr Val Thr Asn Pro Lys Arg Ile Glu Arg Ala Val Glu Glu Lys Ala
                325                 330                 335

Cys Asn Cys Leu Leu Leu Lys Val Asn Gln Ile Gly Ser Val Thr Glu
                340                 345                 350

Ala Ile Gln Ala Cys Lys Leu Ala Gln Glu Asn Gly Trp Gly Val Met
            355                 360                 365

Val Ser His Arg Ser Gly Glu Thr Glu Asp Thr Phe Ile Ala Asp Leu
        370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Glu Glu
                405                 410                 415

Leu Gly Asp Glu Ala Arg Phe Ala Gly His Asn Phe Arg Asn Pro Ser
                420                 425                 430

Val Leu

<210> SEQ ID NO 18
<211> LENGTH: 1231
<212> TYPE: PRT
<213> ORGANISM: Homo sapiens

<400> SEQUENCE: 18

Met Arg Leu Leu Ala Lys Ile Ile Cys Leu Met Leu Trp Ala Ile Cys
1               5                   10                  15
```

-continued

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Val Ile Met
    50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205

Ser Cys Lys Ser Pro Asp Val Ile Asn Gly Ser Pro Ile Ser Gln Lys
    210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
            260                 265                 270

Pro Asn Gly Asp Tyr Ser Pro Leu Arg Ile Lys His Arg Thr Gly Asp
        275                 280                 285

Glu Ile Thr Tyr Gln Cys Arg Asn Gly Phe Tyr Pro Ala Thr Arg Gly
    290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335

His Glu Asn Met Arg Arg Pro Tyr Phe Pro Val Ala Val Gly Lys Tyr
            340                 345                 350

Tyr Ser Tyr Tyr Cys Asp Glu His Phe Glu Thr Pro Ser Gly Ser Tyr
        355                 360                 365

Trp Asp His Ile His Cys Thr Gln Asp Gly Trp Ser Pro Ala Val Pro
    370                 375                 380

Cys Leu Arg Lys Cys Tyr Phe Pro Tyr Leu Glu Asn Gly Tyr Asn Gln
385                 390                 395                 400

Asn His Gly Arg Lys Phe Val Gln Gly Lys Ser Ile Asp Val Ala Cys
                405                 410                 415

His Pro Gly Tyr Ala Leu Pro Lys Ala Gln Thr Thr Val Thr Cys Met
            420                 425                 430

Glu Asn Gly Trp Ser Pro Thr Pro Arg Cys Ile Arg Val Lys Thr Cys

-continued

```
            435                 440                 445
Ser Lys Ser Ser Ile Asp Ile Glu Asn Gly Phe Ile Ser Glu Ser Gln
450                 455                 460

Tyr Thr Tyr Ala Leu Lys Glu Lys Ala Lys Tyr Gln Cys Lys Leu Gly
465                 470                 475                 480

Tyr Val Thr Ala Asp Gly Glu Thr Ser Gly Ser Ile Thr Cys Gly Lys
                485                 490                 495

Asp Gly Trp Ser Ala Gln Pro Thr Cys Ile Lys Ser Cys Asp Ile Pro
                500                 505                 510

Val Phe Met Asn Ala Arg Thr Lys Asn Asp Phe Thr Trp Phe Lys Leu
            515                 520                 525

Asn Asp Thr Leu Asp Tyr Glu Cys His Asp Gly Tyr Glu Ser Asn Thr
530                 535                 540

Gly Ser Thr Thr Gly Ser Ile Val Cys Gly Tyr Asn Gly Trp Ser Asp
545                 550                 555                 560

Leu Pro Ile Cys Tyr Glu Arg Glu Cys Glu Leu Pro Lys Ile Asp Val
                565                 570                 575

His Leu Val Pro Asp Arg Lys Lys Asp Gln Tyr Lys Val Gly Glu Val
                580                 585                 590

Leu Lys Phe Ser Cys Lys Pro Gly Phe Thr Ile Val Gly Pro Asn Ser
            595                 600                 605

Val Gln Cys Tyr His Phe Gly Leu Ser Pro Asp Leu Pro Ile Cys Lys
610                 615                 620

Glu Gln Val Gln Ser Cys Gly Pro Pro Glu Leu Leu Asn Gly Asn
625                 630                 635                 640

Val Lys Glu Lys Thr Lys Glu Tyr Gly His Ser Glu Val Val Glu
                645                 650                 655

Tyr Tyr Cys Asn Pro Arg Phe Leu Met Lys Gly Pro Asn Lys Ile Gln
                660                 665                 670

Cys Val Asp Gly Glu Trp Thr Thr Leu Pro Val Cys Ile Val Glu Glu
            675                 680                 685

Ser Thr Cys Gly Asp Ile Pro Glu Leu Glu His Gly Trp Ala Gln Leu
690                 695                 700

Ser Ser Pro Pro Tyr Tyr Tyr Gly Asp Ser Val Glu Phe Asn Cys Ser
705                 710                 715                 720

Glu Ser Phe Thr Met Ile Gly His Arg Ser Ile Thr Cys Ile His Gly
                725                 730                 735

Val Trp Thr Gln Leu Pro Gln Cys Val Ala Ile Asp Lys Leu Lys Lys
                740                 745                 750

Cys Lys Ser Ser Asn Leu Ile Ile Leu Glu Glu His Leu Lys Asn Lys
            755                 760                 765

Lys Glu Phe Asp His Asn Ser Asn Ile Arg Tyr Arg Cys Arg Gly Lys
770                 775                 780

Glu Gly Trp Ile His Thr Val Cys Ile Asn Gly Arg Trp Asp Pro Glu
785                 790                 795                 800

Val Asn Cys Ser Met Ala Gln Ile Gln Leu Cys Pro Pro Pro Gln
                805                 810                 815

Ile Pro Asn Ser His Asn Met Thr Thr Thr Leu Asn Tyr Arg Asp Gly
                820                 825                 830

Glu Lys Val Ser Val Leu Cys Gln Glu Asn Tyr Leu Ile Gln Glu Gly
            835                 840                 845

Glu Glu Ile Thr Cys Lys Asp Gly Arg Trp Gln Ser Ile Pro Leu Cys
850                 855                 860
```

Val Glu Lys Ile Pro Cys Ser Gln Pro Pro Gln Ile Glu His Gly Thr
865                 870                 875                 880

Ile Asn Ser Ser Arg Ser Ser Gln Glu Ser Tyr Ala His Gly Thr Lys
                885                 890                 895

Leu Ser Tyr Thr Cys Glu Gly Gly Phe Arg Ile Ser Glu Glu Asn Glu
            900                 905                 910

Thr Thr Cys Tyr Met Gly Lys Trp Ser Ser Pro Pro Gln Cys Glu Gly
        915                 920                 925

Leu Pro Cys Lys Ser Pro Pro Glu Ile Ser His Gly Val Val Ala His
    930                 935                 940

Met Ser Asp Ser Tyr Gln Tyr Gly Glu Glu Val Thr Tyr Lys Cys Phe
945                 950                 955                 960

Glu Gly Phe Gly Ile Asp Gly Pro Ala Ile Ala Lys Cys Leu Gly Glu
                965                 970                 975

Lys Trp Ser His Pro Pro Ser Cys Ile Lys Thr Asp Cys Leu Ser Leu
            980                 985                 990

Pro Ser Phe Glu Asn Ala Ile Pro Met Gly Glu Lys Lys Asp Val Tyr
        995                 1000                1005

Lys Ala Gly Glu Gln Val Thr Tyr Thr Cys Ala Thr Tyr Tyr Lys
    1010                1015                1020

Met Asp Gly Ala Ser Asn Val Thr Cys Ile Asn Ser Arg Trp Thr
    1025                1030                1035

Gly Arg Pro Thr Cys Arg Asp Thr Ser Cys Val Asn Pro Pro Thr
    1040                1045                1050

Val Gln Asn Ala Tyr Ile Val Ser Arg Gln Met Ser Lys Tyr Pro
    1055                1060                1065

Ser Gly Glu Arg Val Arg Tyr Gln Cys Arg Ser Pro Tyr Glu Met
    1070                1075                1080

Phe Gly Asp Glu Glu Val Met Cys Leu Asn Gly Asn Trp Thr Glu
    1085                1090                1095

Pro Pro Gln Cys Lys Asp Ser Thr Gly Lys Cys Gly Pro Pro Pro
    1100                1105                1110

Pro Ile Asp Asn Gly Asp Ile Thr Ser Phe Pro Leu Ser Val Tyr
    1115                1120                1125

Ala Pro Ala Ser Ser Val Glu Tyr Gln Cys Gln Asn Leu Tyr Gln
    1130                1135                1140

Leu Glu Gly Asn Lys Arg Ile Thr Cys Arg Asn Gly Gln Trp Ser
    1145                1150                1155

Glu Pro Pro Lys Cys Leu His Pro Cys Val Ile Ser Arg Glu Ile
    1160                1165                1170

Met Glu Asn Tyr Asn Ile Ala Leu Arg Trp Thr Ala Lys Gln Lys
    1175                1180                1185

Leu Tyr Ser Arg Thr Gly Glu Ser Val Glu Phe Val Cys Lys Arg
    1190                1195                1200

Gly Tyr Arg Leu Ser Ser Arg Ser His Thr Leu Arg Thr Thr Cys
    1205                1210                1215

Trp Asp Gly Lys Leu Glu Tyr Pro Thr Cys Ala Lys Arg
    1220                1225                1230

<210> SEQ ID NO 19
<211> LENGTH: 770
<212> TYPE: PRT
<213> ORGANISM: Homo sapiens

<400> SEQUENCE: 19

```
Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
            245                 250                 255

Glu Ala Glu Glu Pro Tyr Glu Glu Ala Thr Glu Arg Thr Thr Ser Ile
        260                 265                 270

Ala Thr Thr Thr Thr Thr Thr Thr Glu Ser Val Glu Glu Val Val Arg
    275                 280                 285

Glu Val Cys Ser Glu Gln Ala Glu Thr Gly Pro Cys Arg Ala Met Ile
        290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
            325                 330                 335

Cys Met Ala Val Cys Gly Ser Ala Met Ser Gln Ser Leu Leu Lys Thr
        340                 345                 350

Thr Gln Glu Pro Leu Ala Arg Asp Pro Val Lys Leu Pro Thr Thr Ala
    355                 360                 365

Ala Ser Thr Pro Asp Ala Val Asp Lys Tyr Leu Glu Thr Pro Gly Asp
    370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
            405                 410                 415
```

Glu Arg Gln Ala Lys Asn Leu Pro Lys Ala Asp Lys Ala Val Ile
            420                 425                 430

Gln His Phe Gln Glu Lys Val Glu Ser Leu Glu Gln Glu Ala Ala Asn
        435                 440                 445

Glu Arg Gln Gln Leu Val Glu Thr His Met Ala Arg Val Glu Ala Met
450                 455                 460

Leu Asn Asp Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
                485                 490                 495

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
        515                 520                 525

Gln Val Met Thr His Leu Arg Val Ile Tyr Glu Arg Met Asn Gln Ser
530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Val
                565                 570                 575

Leu Ala Asn Met Ile Ser Glu Pro Arg Ile Ser Tyr Gly Asn Asp Ala
            580                 585                 590

Leu Met Pro Ser Leu Thr Glu Thr Lys Thr Thr Val Glu Leu Leu Pro
        595                 600                 605

Val Asn Gly Glu Phe Ser Leu Asp Asp Leu Gln Pro Trp His Ser Phe
610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
            660                 665                 670

Ala Glu Phe Arg His Asp Ser Gly Tyr Glu Val His His Gln Lys Leu
        675                 680                 685

Val Phe Phe Ala Glu Asp Val Gly Ser Asn Lys Gly Ala Ile Ile Gly
690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
        755                 760                 765

Gln Asn
770

<210> SEQ ID NO 20
<211> LENGTH: 1065
<212> TYPE: PRT
<213> ORGANISM: Homo sapiens

<400> SEQUENCE: 20

Met Lys Ile Leu Ile Leu Gly Ile Phe Leu Phe Leu Cys Ser Thr Pro

```
1               5                   10                  15
Ala Trp Ala Lys Glu Lys His Tyr Tyr Ile Gly Ile Glu Thr Thr
                20                  25                  30
Trp Asp Tyr Ala Ser Asp His Gly Glu Lys Lys Leu Ile Ser Val Asp
                35                  40                  45
Thr Glu His Ser Asn Ile Tyr Leu Gln Asn Gly Pro Asp Arg Ile Gly
                50                  55                  60
Arg Leu Tyr Lys Lys Ala Leu Tyr Leu Gln Tyr Thr Asp Glu Thr Phe
65                  70                  75                  80
Arg Thr Thr Ile Glu Lys Pro Val Trp Leu Gly Phe Leu Gly Pro Ile
                85                  90                  95
Ile Lys Ala Glu Thr Gly Asp Lys Val Tyr Val His Leu Lys Asn Leu
                100                 105                 110
Ala Ser Arg Pro Tyr Thr Phe His Ser His Gly Ile Thr Tyr Tyr Lys
                115                 120                 125
Glu His Glu Gly Ala Ile Tyr Pro Asp Asn Thr Thr Asp Phe Gln Arg
                130                 135                 140
Ala Asp Asp Lys Val Tyr Pro Gly Glu Gln Tyr Thr Tyr Met Leu Leu
145                 150                 155                 160
Ala Thr Glu Glu Gln Ser Pro Gly Glu Gly Asp Gly Asn Cys Val Thr
                165                 170                 175
Arg Ile Tyr His Ser His Ile Asp Ala Pro Lys Asp Ile Ala Ser Gly
                180                 185                 190
Leu Ile Gly Pro Leu Ile Ile Cys Lys Lys Asp Ser Leu Asp Lys Glu
                195                 200                 205
Lys Glu Lys His Ile Asp Arg Glu Phe Val Val Met Phe Ser Val Val
                210                 215                 220
Asp Glu Asn Phe Ser Trp Tyr Leu Glu Asp Asn Ile Lys Thr Tyr Cys
225                 230                 235                 240
Ser Glu Pro Glu Lys Val Asp Lys Asp Asn Glu Asp Phe Gln Glu Ser
                245                 250                 255
Asn Arg Met Tyr Ser Val Asn Gly Tyr Thr Phe Gly Ser Leu Pro Gly
                260                 265                 270
Leu Ser Met Cys Ala Glu Asp Arg Val Lys Trp Tyr Leu Phe Gly Met
                275                 280                 285
Gly Asn Glu Val Asp Val His Ala Ala Phe Phe His Gly Gln Ala Leu
                290                 295                 300
Thr Asn Lys Asn Tyr Arg Ile Asp Thr Ile Asn Leu Phe Pro Ala Thr
305                 310                 315                 320
Leu Phe Asp Ala Tyr Met Val Ala Gln Asn Pro Gly Glu Trp Met Leu
                325                 330                 335
Ser Cys Gln Asn Leu Asn His Leu Lys Ala Gly Leu Gln Ala Phe Phe
                340                 345                 350
Gln Val Gln Glu Cys Asn Lys Ser Ser Lys Asp Asn Ile Arg Gly
                355                 360                 365
Lys His Val Arg His Tyr Tyr Ile Ala Ala Glu Ile Ile Trp Asn
                370                 375                 380
Tyr Ala Pro Ser Gly Ile Asp Ile Phe Thr Lys Glu Asn Leu Thr Ala
385                 390                 395                 400
Pro Gly Ser Asp Ser Ala Val Phe Phe Glu Gln Gly Thr Thr Arg Ile
                405                 410                 415
Gly Gly Ser Tyr Lys Lys Leu Val Tyr Arg Glu Tyr Thr Asp Ala Ser
                420                 425                 430
```

```
Phe Thr Asn Arg Lys Glu Arg Gly Pro Glu Glu His Leu Gly Ile
        435                 440                 445

Leu Gly Pro Val Ile Trp Ala Glu Val Gly Asp Thr Ile Arg Val Thr
450                 455                 460

Phe His Asn Lys Gly Ala Tyr Pro Leu Ser Ile Glu Pro Ile Gly Val
465                 470                 475                 480

Arg Phe Asn Lys Asn Asn Glu Gly Thr Tyr Tyr Ser Pro Asn Tyr Asn
                485                 490                 495

Pro Gln Ser Arg Ser Val Pro Pro Ser Ala Ser His Val Ala Pro Thr
                500                 505                 510

Glu Thr Phe Thr Tyr Glu Trp Thr Val Pro Lys Glu Val Gly Pro Thr
            515                 520                 525

Asn Ala Asp Pro Val Cys Leu Ala Lys Met Tyr Tyr Ser Ala Val Asp
        530                 535                 540

Pro Thr Lys Asp Ile Phe Thr Gly Leu Ile Gly Pro Met Lys Ile Cys
545                 550                 555                 560

Lys Lys Gly Ser Leu His Ala Asn Gly Arg Gln Lys Asp Val Asp Lys
                565                 570                 575

Glu Phe Tyr Leu Phe Pro Thr Val Phe Asp Glu Asn Glu Ser Leu Leu
                580                 585                 590

Leu Glu Asp Asn Ile Arg Met Phe Thr Thr Ala Pro Asp Gln Val Asp
            595                 600                 605

Lys Glu Asp Glu Asp Phe Gln Glu Ser Asn Lys Met His Ser Met Asn
        610                 615                 620

Gly Phe Met Tyr Gly Asn Gln Pro Gly Leu Thr Met Cys Lys Gly Asp
625                 630                 635                 640

Ser Val Val Trp Tyr Leu Phe Ser Ala Gly Asn Glu Ala Asp Val His
                645                 650                 655

Gly Ile Tyr Phe Ser Gly Asn Thr Tyr Leu Trp Arg Gly Glu Arg Arg
                660                 665                 670

Asp Thr Ala Asn Leu Phe Pro Gln Thr Ser Leu Thr Leu His Met Trp
            675                 680                 685

Pro Asp Thr Glu Gly Thr Phe Asn Val Glu Cys Leu Thr Thr Asp His
        690                 695                 700

Tyr Thr Gly Gly Met Lys Gln Lys Tyr Thr Val Asn Gln Cys Arg Arg
705                 710                 715                 720

Gln Ser Glu Asp Ser Thr Phe Tyr Leu Gly Glu Arg Thr Tyr Tyr Ile
                725                 730                 735

Ala Ala Val Glu Val Glu Trp Asp Tyr Ser Pro Gln Arg Glu Trp Glu
                740                 745                 750

Lys Glu Leu His His Leu Gln Glu Gln Asn Val Ser Asn Ala Phe Leu
            755                 760                 765

Asp Lys Gly Glu Phe Tyr Ile Gly Ser Lys Tyr Lys Lys Val Val Tyr
        770                 775                 780

Arg Gln Tyr Thr Asp Ser Thr Phe Arg Val Pro Val Glu Arg Lys Ala
785                 790                 795                 800

Glu Glu Glu His Leu Gly Ile Leu Gly Pro Gln Leu His Ala Asp Val
                805                 810                 815

Gly Asp Lys Val Lys Ile Ile Phe Lys Asn Met Ala Thr Arg Pro Tyr
                820                 825                 830

Ser Ile His Ala His Gly Val Gln Thr Glu Ser Ser Thr Val Thr Pro
            835                 840                 845
```

Thr Leu Pro Gly Glu Thr Leu Thr Tyr Val Trp Lys Ile Pro Glu Arg
            850                 855                 860

Ser Gly Ala Gly Thr Glu Asp Ser Ala Cys Ile Pro Trp Ala Tyr Tyr
865                 870                 875                 880

Ser Thr Val Asp Gln Val Lys Asp Leu Tyr Ser Gly Leu Ile Gly Pro
            885                 890                 895

Leu Ile Val Cys Arg Arg Pro Tyr Leu Lys Val Phe Asn Pro Arg Arg
            900                 905                 910

Lys Leu Glu Phe Ala Leu Leu Phe Leu Val Phe Asp Glu Asn Glu Ser
            915                 920                 925

Trp Tyr Leu Asp Asp Asn Ile Lys Thr Tyr Ser Asp His Pro Glu Lys
            930                 935                 940

Val Asn Lys Asp Asp Glu Glu Phe Ile Glu Ser Asn Lys Met His Ala
945                 950                 955                 960

Ile Asn Gly Arg Met Phe Gly Asn Leu Gln Gly Leu Thr Met His Val
            965                 970                 975

Gly Asp Glu Val Asn Trp Tyr Leu Met Gly Met Gly Asn Glu Ile Asp
            980                 985                 990

Leu His Thr Val His Phe His Gly His Ser Phe Gln Tyr Lys His Arg
            995                 1000                1005

Gly Val Tyr Ser Ser Asp Val Phe Asp Ile Phe Pro Gly Thr Tyr
    1010                1015                1020

Gln Thr Leu Glu Met Phe Pro Arg Thr Pro Gly Ile Trp Leu Leu
    1025                1030                1035

His Cys His Val Thr Asp His Ile His Ala Gly Met Glu Thr Thr
    1040                1045                1050

Tyr Thr Val Leu Gln Asn Glu Asp Thr Lys Ser Gly
    1055                1060                1065

<210> SEQ ID NO 21
<211> LENGTH: 848
<212> TYPE: PRT
<213> ORGANISM: Homo sapiens

<400> SEQUENCE: 21

Met Leu Gln Thr Lys Asp Leu Ile Trp Thr Leu Phe Phe Leu Gly Thr
1               5                   10                  15

Ala Val Ser Leu Gln Val Asp Ile Val Pro Ser Gln Gly Glu Ile Ser
            20                  25                  30

Val Gly Glu Ser Lys Phe Phe Leu Cys Gln Val Ala Gly Asp Ala Lys
        35                  40                  45

Asp Lys Asp Ile Ser Trp Phe Ser Pro Asn Gly Glu Lys Leu Thr Pro
    50                  55                  60

Asn Gln Gln Arg Ile Ser Val Val Trp Asn Asp Ser Ser Ser Thr
65                  70                  75                  80

Leu Thr Ile Tyr Asn Ala Asn Ile Asp Asp Ala Gly Ile Tyr Lys Cys
                85                  90                  95

Val Val Thr Gly Glu Asp Gly Ser Glu Ser Glu Ala Thr Val Asn Val
            100                 105                 110

Lys Ile Phe Gln Lys Leu Met Phe Lys Asn Ala Pro Thr Pro Gln Glu
        115                 120                 125

Phe Arg Glu Gly Glu Asp Ala Val Ile Val Cys Asp Val Val Ser Ser
    130                 135                 140

Leu Pro Pro Thr Ile Ile Trp Lys His Lys Gly Arg Asp Val Ile Leu
145                 150                 155                 160

-continued

```
Lys Lys Asp Val Arg Phe Ile Val Leu Ser Asn Asn Tyr Leu Gln Ile
                165                 170                 175
Arg Gly Ile Lys Lys Thr Asp Glu Gly Thr Tyr Arg Cys Glu Gly Arg
            180                 185                 190
Ile Leu Ala Arg Gly Glu Ile Asn Phe Lys Asp Ile Gln Val Ile Val
        195                 200                 205
Asn Val Pro Pro Thr Ile Gln Ala Arg Gln Asn Ile Val Asn Ala Thr
    210                 215                 220
Ala Asn Leu Gly Gln Ser Val Thr Leu Val Cys Asp Ala Glu Gly Phe
225                 230                 235                 240
Pro Glu Pro Thr Met Ser Trp Thr Lys Asp Gly Glu Gln Ile Glu Gln
                245                 250                 255
Glu Glu Asp Asp Glu Lys Tyr Ile Phe Ser Asp Asp Ser Ser Gln Leu
            260                 265                 270
Thr Ile Lys Lys Val Asp Lys Asn Asp Glu Ala Glu Tyr Ile Cys Ile
        275                 280                 285
Ala Glu Asn Lys Ala Gly Glu Gln Asp Ala Thr Ile His Leu Lys Val
    290                 295                 300
Phe Ala Lys Pro Lys Ile Thr Tyr Val Glu Asn Gln Thr Ala Met Glu
305                 310                 315                 320
Leu Glu Glu Gln Val Thr Leu Thr Cys Glu Ala Ser Gly Asp Pro Ile
                325                 330                 335
Pro Ser Ile Thr Trp Arg Thr Ser Thr Arg Asn Ile Ser Ser Glu Glu
            340                 345                 350
Lys Thr Leu Asp Gly His Met Val Val Arg Ser His Ala Arg Val Ser
        355                 360                 365
Ser Leu Thr Leu Lys Ser Ile Gln Tyr Thr Asp Ala Gly Glu Tyr Ile
    370                 375                 380
Cys Thr Ala Ser Asn Thr Ile Gly Gln Asp Ser Gln Ser Met Tyr Leu
385                 390                 395                 400
Glu Val Gln Tyr Ala Pro Lys Leu Gln Gly Pro Val Ala Val Tyr Thr
                405                 410                 415
Trp Glu Gly Asn Gln Val Asn Ile Thr Cys Glu Val Phe Ala Tyr Pro
            420                 425                 430
Ser Ala Thr Ile Ser Trp Phe Arg Asp Gly Gln Leu Leu Pro Ser Ser
        435                 440                 445
Asn Tyr Ser Asn Ile Lys Ile Tyr Asn Thr Pro Ser Ala Ser Tyr Leu
    450                 455                 460
Glu Val Thr Pro Asp Ser Glu Asn Asp Phe Gly Asn Tyr Asn Cys Thr
465                 470                 475                 480
Ala Val Asn Arg Ile Gly Gln Glu Ser Leu Glu Phe Ile Leu Val Gln
                485                 490                 495
Ala Asp Thr Pro Ser Ser Pro Ser Ile Asp Gln Val Glu Pro Tyr Ser
            500                 505                 510
Ser Thr Ala Gln Val Gln Phe Asp Glu Pro Glu Ala Thr Gly Gly Val
        515                 520                 525
Pro Ile Leu Lys Tyr Lys Ala Glu Trp Arg Ala Val Gly Glu Glu Val
    530                 535                 540
Trp His Ser Lys Trp Tyr Asp Ala Lys Glu Ala Ser Met Glu Gly Ile
545                 550                 555                 560
Val Thr Ile Val Gly Leu Lys Pro Glu Thr Thr Tyr Ala Val Arg Leu
                565                 570                 575
```

-continued

Ala Ala Leu Asn Gly Lys Gly Leu Gly Glu Ile Ser Ala Ala Ser Glu
            580                 585                 590

Phe Lys Thr Gln Pro Val Gln Gly Glu Pro Ser Ala Pro Lys Leu Glu
        595                 600                 605

Gly Gln Met Gly Glu Asp Gly Asn Ser Ile Lys Val Asn Leu Ile Lys
            610                 615                 620

Gln Asp Asp Gly Gly Ser Pro Ile Arg His Tyr Leu Val Arg Tyr Arg
625                 630                 635                 640

Ala Leu Ser Ser Glu Trp Lys Pro Glu Ile Arg Leu Pro Ser Gly Ser
            645                 650                 655

Asp His Val Met Leu Lys Ser Leu Asp Trp Asn Ala Glu Tyr Glu Val
            660                 665                 670

Tyr Val Val Ala Glu Asn Gln Gln Gly Lys Ser Lys Ala Ala His Phe
            675                 680                 685

Val Phe Arg Thr Ser Ala Gln Pro Thr Ala Ile Pro Ala Asn Gly Ser
            690                 695                 700

Pro Thr Ser Gly Leu Ser Thr Gly Ala Ile Val Gly Ile Leu Ile Val
705                 710                 715                 720

Ile Phe Val Leu Leu Leu Val Val Val Asp Ile Thr Cys Tyr Phe Leu
            725                 730                 735

Asn Lys Cys Gly Leu Phe Met Cys Ile Ala Val Asn Leu Cys Gly Lys
            740                 745                 750

Ala Gly Pro Gly Ala Lys Gly Lys Asp Met Glu Glu Gly Lys Ala Ala
            755                 760                 765

Phe Ser Lys Asp Glu Ser Lys Glu Pro Ile Val Glu Val Arg Thr Glu
            770                 775                 780

Glu Glu Arg Thr Pro Asn His Asp Gly Gly Lys His Thr Glu Pro Asn
785                 790                 795                 800

Glu Thr Thr Pro Leu Thr Glu Pro Glu Lys Gly Pro Val Glu Ala Lys
            805                 810                 815

Pro Glu Cys Gln Glu Thr Glu Thr Lys Pro Ala Pro Ala Glu Val Lys
            820                 825                 830

Thr Val Pro Asn Asp Ala Thr Gln Thr Lys Glu Asn Glu Ser Lys Ala
            835                 840                 845

<210> SEQ ID NO 22
<211> LENGTH: 67
<212> TYPE: PRT
<213> ORGANISM: Homo sapiens

<400> SEQUENCE: 22

Leu Ser Pro Leu Gly Glu Glu Met Arg Asp Arg Ala Arg Ala His Val
1               5                   10                  15

Asp Ala Leu Arg Thr His Leu Ala Pro Tyr Ser Asp Glu Leu Arg Gln
            20                  25                  30

Pro Leu Ala Ala Arg Leu Glu Ala Leu Lys Glu Asn Gly Gly Ala Arg
        35                  40                  45

Leu Ala Glu Tyr His Ala Lys Ala Thr Glu His Leu Ser Thr Leu Ser
    50                  55                  60

Glu Lys Ala
65

<210> SEQ ID NO 23
<211> LENGTH: 247
<212> TYPE: PRT
<213> ORGANISM: Homo sapiens

<400> SEQUENCE: 23

```
Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp His Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Phe Leu Leu Glu Glu
            100                 105                 110

Tyr Lys Asn Tyr Leu Asp Ala Ala Asn Met Ser Met Met Val Leu Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Arg Gly Arg
                245
```

<210> SEQ ID NO 24
<211> LENGTH: 338
<212> TYPE: PRT
<213> ORGANISM: Homo sapiens

<400> SEQUENCE: 24

```
Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
            20                  25                  30

Ser Ala Ala Val Ser Arg Pro Gly Arg Gly Glu Pro Arg Phe Ile Ala
        35                  40                  45

Met Gly Tyr Val Asp Asp Thr Gln Phe Val Arg Phe Asp Ser Asp Ser
    50                  55                  60

Ala Cys Pro Arg Met Glu Pro Arg Ala Pro Trp Val Glu Gln Glu Gly
65                  70                  75                  80

Pro Glu Tyr Trp Glu Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
            100                 105                 110
```

```
Glu Ala Ser Ser His Thr Leu Gln Trp Met Ile Gly Cys Asp Leu Gly
            115                 120                 125

Ser Asp Gly Arg Leu Leu Arg Gly Tyr Glu Gln Tyr Ala Tyr Asp Gly
        130                 135                 140

Lys Asp Tyr Leu Ala Leu Asn Glu Asp Leu Arg Ser Trp Thr Ala Ala
145                 150                 155                 160

Asp Thr Ala Ala Gln Ile Ser Lys Arg Lys Cys Glu Ala Ala Asn Val
                165                 170                 175

Ala Glu Gln Arg Arg Ala Tyr Leu Glu Gly Thr Cys Val Glu Trp Leu
            180                 185                 190

His Arg Tyr Leu Glu Asn Gly Lys Glu Met Leu Gln Arg Ala Asp Pro
        195                 200                 205

Pro Lys Thr His Val Thr His His Pro Val Phe Asp Tyr Glu Ala Thr
    210                 215                 220

Leu Arg Cys Trp Ala Leu Gly Phe Tyr Pro Ala Glu Ile Ile Leu Thr
225                 230                 235                 240

Trp Gln Arg Asp Gly Glu Asp Gln Thr Gln Asp Val Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Glu Pro Leu Met Leu Arg Trp Lys Gln Ser Ser Leu Pro
    290                 295                 300

Thr Ile Pro Ile Met Gly Ile Val Ala Gly Leu Val Val Leu Ala Ala
305                 310                 315                 320

Val Val Thr Gly Ala Ala Val Ala Ala Val Leu Trp Arg Lys Lys Ser
                325                 330                 335

Ser Asp

<210> SEQ ID NO 25
<211> LENGTH: 739
<212> TYPE: PRT
<213> ORGANISM: Homo sapiens

<400> SEQUENCE: 25

Met Pro Gly Lys Met Val Val Ile Leu Gly Ala Ser Asn Ile Leu Trp
1               5                   10                  15

Ile Met Phe Ala Ala Ser Gln Ala Phe Lys Ile Glu Thr Thr Pro Glu
            20                  25                  30

Ser Arg Tyr Leu Ala Gln Ile Gly Asp Ser Val Ser Leu Thr Cys Ser
        35                  40                  45

Thr Thr Gly Cys Glu Ser Pro Phe Phe Ser Trp Arg Thr Gln Ile Asp
    50                  55                  60

Ser Pro Leu Asn Gly Lys Val Thr Asn Glu Gly Thr Thr Ser Thr Leu
65                  70                  75                  80

Thr Met Asn Pro Val Ser Phe Gly Asn Glu His Ser Tyr Leu Cys Thr
                85                  90                  95

Ala Thr Cys Glu Ser Arg Lys Leu Glu Lys Gly Ile Gln Val Glu Ile
            100                 105                 110

Tyr Ser Phe Pro Lys Asp Pro Glu Ile His Leu Ser Gly Pro Leu Glu
        115                 120                 125

Ala Gly Lys Pro Ile Thr Val Lys Cys Ser Val Ala Asp Val Tyr Pro
    130                 135                 140
```

```
Phe Asp Arg Leu Glu Ile Asp Leu Leu Lys Gly Asp His Leu Met Lys
145                 150                 155                 160

Ser Gln Glu Phe Leu Glu Asp Ala Asp Arg Lys Ser Leu Glu Thr Lys
                165                 170                 175

Ser Leu Glu Val Thr Phe Thr Pro Val Ile Glu Asp Ile Gly Lys Val
            180                 185                 190

Leu Val Cys Arg Ala Lys Leu His Ile Asp Glu Met Asp Ser Val Pro
        195                 200                 205

Thr Val Arg Gln Ala Val Lys Glu Leu Gln Val Tyr Ile Ser Pro Lys
    210                 215                 220

Asn Thr Val Ile Ser Val Asn Pro Ser Thr Lys Leu Gln Glu Gly Gly
225                 230                 235                 240

Ser Val Thr Met Thr Cys Ser Ser Glu Gly Leu Pro Ala Pro Glu Ile
                245                 250                 255

Phe Trp Ser Lys Lys Leu Asp Asn Gly Asn Leu Gln His Leu Ser Gly
            260                 265                 270

Asn Ala Thr Leu Thr Leu Ile Ala Met Arg Met Glu Asp Ser Gly Ile
        275                 280                 285

Tyr Val Cys Glu Gly Val Asn Leu Ile Gly Lys Asn Arg Lys Glu Val
    290                 295                 300

Glu Leu Ile Val Gln Glu Lys Pro Phe Thr Val Glu Ile Ser Pro Gly
305                 310                 315                 320

Pro Arg Ile Ala Ala Gln Ile Gly Asp Ser Val Met Leu Thr Cys Ser
                325                 330                 335

Val Met Gly Cys Glu Ser Pro Ser Phe Ser Trp Arg Thr Gln Ile Asp
            340                 345                 350

Ser Pro Leu Ser Gly Lys Val Arg Ser Glu Gly Thr Asn Ser Thr Leu
        355                 360                 365

Thr Leu Ser Pro Val Ser Phe Glu Asn Glu His Ser Tyr Leu Cys Thr
    370                 375                 380

Val Thr Cys Gly His Lys Lys Leu Glu Lys Gly Ile Gln Val Glu Leu
385                 390                 395                 400

Tyr Ser Phe Pro Arg Asp Pro Glu Ile Glu Met Ser Gly Gly Leu Val
                405                 410                 415

Asn Gly Ser Ser Val Thr Val Ser Cys Lys Val Pro Ser Val Tyr Pro
            420                 425                 430

Leu Asp Arg Leu Glu Ile Glu Leu Leu Lys Gly Glu Thr Ile Leu Glu
        435                 440                 445

Asn Ile Glu Phe Leu Glu Asp Thr Asp Met Lys Ser Leu Glu Asn Lys
    450                 455                 460

Ser Leu Glu Met Thr Phe Ile Pro Thr Ile Glu Asp Thr Gly Lys Ala
465                 470                 475                 480

Leu Val Cys Gln Ala Lys Leu His Ile Asp Asp Met Glu Phe Glu Pro
                485                 490                 495

Lys Gln Arg Gln Ser Thr Gln Thr Leu Tyr Val Asn Val Ala Pro Arg
            500                 505                 510

Asp Thr Thr Val Leu Val Ser Pro Ser Ser Ile Leu Glu Glu Gly Ser
        515                 520                 525

Ser Val Asn Met Thr Cys Leu Ser Gln Gly Phe Pro Ala Pro Lys Ile
    530                 535                 540

Leu Trp Ser Arg Gln Leu Pro Asn Gly Glu Leu Gln Pro Leu Ser Glu
545                 550                 555                 560
```

```
Asn Ala Thr Leu Thr Leu Ile Ser Thr Lys Met Glu Asp Ser Gly Val
            565                 570                 575
Tyr Leu Cys Glu Gly Ile Asn Gln Ala Gly Arg Ser Arg Lys Glu Val
            580                 585                 590
Glu Leu Ile Ile Gln Val Thr Pro Lys Asp Ile Lys Leu Thr Ala Phe
            595                 600                 605
Pro Ser Glu Ser Val Lys Glu Gly Asp Thr Val Ile Ile Ser Cys Thr
            610                 615                 620
Cys Gly Asn Val Pro Glu Thr Trp Ile Ile Leu Lys Lys Lys Ala Glu
625                 630                 635                 640
Thr Gly Asp Thr Val Leu Lys Ser Ile Asp Gly Ala Tyr Thr Ile Arg
            645                 650                 655
Lys Ala Gln Leu Lys Asp Ala Gly Val Tyr Glu Cys Glu Ser Lys Asn
            660                 665                 670
Lys Val Gly Ser Gln Leu Arg Ser Leu Thr Leu Asp Val Gln Gly Arg
            675                 680                 685
Glu Asn Asn Lys Asp Tyr Phe Ser Pro Glu Leu Leu Val Leu Tyr Phe
            690                 695                 700
Ala Ser Ser Leu Ile Ile Pro Ala Ile Gly Met Ile Ile Tyr Phe Ala
705                 710                 715                 720
Arg Lys Ala Asn Met Lys Gly Ser Tyr Ser Leu Val Glu Ala Gln Lys
            725                 730                 735
Ser Lys Val

<210> SEQ ID NO 26
<211> LENGTH: 404
<212> TYPE: PRT
<213> ORGANISM: Homo sapiens

<400> SEQUENCE: 26

Met Ala Ala Gly Thr Ala Val Gly Ala Trp Val Leu Val Leu Ser Leu
1               5                   10                  15
Trp Gly Ala Val Val Gly Ala Gln Asn Ile Thr Ala Arg Ile Gly Glu
            20                  25                  30
Pro Leu Val Leu Lys Cys Lys Gly Ala Pro Lys Lys Pro Pro Gln Arg
            35                  40                  45
Leu Glu Trp Lys Leu Asn Thr Gly Arg Thr Glu Ala Trp Lys Val Leu
            50                  55                  60
Ser Pro Gln Gly Gly Gly Pro Trp Asp Ser Val Ala Arg Val Leu Pro
65                  70                  75                  80
Asn Gly Ser Leu Phe Leu Pro Ala Val Gly Ile Gln Asp Glu Gly Ile
            85                  90                  95
Phe Arg Cys Gln Ala Met Asn Arg Asn Gly Lys Glu Thr Lys Ser Asn
            100                 105                 110
Tyr Arg Val Arg Val Tyr Gln Ile Pro Gly Lys Pro Glu Ile Val Asp
            115                 120                 125
Ser Ala Ser Glu Leu Thr Ala Gly Val Pro Asn Lys Val Gly Thr Cys
            130                 135                 140
Val Ser Glu Gly Ser Tyr Pro Ala Gly Thr Leu Ser Trp His Leu Asp
145                 150                 155                 160
Gly Lys Pro Leu Val Pro Asn Glu Lys Gly Val Ser Val Lys Glu Gln
            165                 170                 175
Thr Arg Arg His Pro Glu Thr Gly Leu Phe Thr Leu Gln Ser Glu Leu
            180                 185                 190
```

-continued

```
Met Val Thr Pro Ala Arg Gly Asp Pro Arg Pro Thr Phe Ser Cys
            195                 200                 205
Ser Phe Ser Pro Gly Leu Pro Arg His Arg Ala Leu Arg Thr Ala Pro
210                 215                 220
Ile Gln Pro Arg Val Trp Glu Pro Val Pro Leu Glu Glu Val Gln Leu
225                 230                 235                 240
Val Val Glu Pro Glu Gly Gly Ala Val Ala Pro Gly Gly Thr Val Thr
                245                 250                 255
Leu Thr Cys Glu Val Pro Ala Gln Pro Ser Pro Gln Ile His Trp Met
            260                 265                 270
Lys Asp Gly Val Pro Leu Pro Leu Pro Pro Ser Pro Val Leu Ile Leu
275                 280                 285
Pro Glu Ile Gly Pro Gln Asp Gln Gly Thr Tyr Ser Cys Val Ala Thr
        290                 295                 300
His Ser Ser His Gly Pro Gln Glu Ser Arg Ala Val Ser Ile Ser Ile
305                 310                 315                 320
Ile Glu Pro Gly Glu Gly Pro Thr Ala Gly Ser Val Gly Gly Ser
                325                 330                 335
Gly Leu Gly Thr Leu Ala Leu Ala Leu Gly Ile Leu Gly Gly Leu Gly
                340                 345                 350
Thr Ala Ala Leu Leu Ile Gly Val Ile Leu Trp Gln Arg Arg Gln Arg
            355                 360                 365
Arg Gly Glu Glu Arg Lys Ala Pro Glu Asn Gln Glu Glu Glu Glu Glu
370                 375                 380
Arg Ala Glu Leu Asn Gln Ser Glu Glu Pro Glu Ala Gly Glu Ser Ser
385                 390                 395                 400
Thr Gly Gly Pro
```

<210> SEQ ID NO 27
<211> LENGTH: 770
<212> TYPE: PRT
<213> ORGANISM: Homo sapiens

<400> SEQUENCE: 27

```
Met Leu Pro Gly Leu Ala Leu Leu Leu Leu Ala Ala Trp Thr Ala Arg
1               5                   10                  15
Ala Leu Glu Val Pro Thr Asp Gly Asn Ala Gly Leu Leu Ala Glu Pro
                20                  25                  30
Gln Ile Ala Met Phe Cys Gly Arg Leu Asn Met His Met Asn Val Gln
            35                  40                  45
Asn Gly Lys Trp Asp Ser Asp Pro Ser Gly Thr Lys Thr Cys Ile Asp
        50                  55                  60
Thr Lys Glu Gly Ile Leu Gln Tyr Cys Gln Glu Val Tyr Pro Glu Leu
65                  70                  75                  80
Gln Ile Thr Asn Val Val Glu Ala Asn Gln Pro Val Thr Ile Gln Asn
                85                  90                  95
Trp Cys Lys Arg Gly Arg Lys Gln Cys Lys Thr His Pro His Phe Val
            100                 105                 110
Ile Pro Tyr Arg Cys Leu Val Gly Glu Phe Val Ser Asp Ala Leu Leu
        115                 120                 125
Val Pro Asp Lys Cys Lys Phe Leu His Gln Glu Arg Met Asp Val Cys
130                 135                 140
Glu Thr His Leu His Trp His Thr Val Ala Lys Glu Thr Cys Ser Glu
145                 150                 155                 160
```

-continued

```
Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
    290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
            340                 345                 350

Thr Gln Glu Pro Leu Ala Arg Asp Pro Val Lys Leu Pro Thr Thr Ala
        355                 360                 365

Ala Ser Thr Pro Asp Ala Val Asp Lys Tyr Leu Glu Thr Pro Gly Asp
    370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
                405                 410                 415

Glu Arg Gln Ala Lys Asn Leu Pro Lys Ala Asp Lys Lys Ala Val Ile
            420                 425                 430

Gln His Phe Gln Glu Lys Val Glu Ser Leu Glu Gln Glu Ala Ala Asn
        435                 440                 445

Glu Arg Gln Gln Leu Val Glu Thr His Met Ala Arg Val Glu Ala Met
    450                 455                 460

Leu Asn Asp Arg Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
                485                 490                 495

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
        515                 520                 525

Gln Val Met Thr His Leu Arg Val Ile Tyr Glu Arg Met Asn Gln Ser
    530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
```

-continued

```
                    580                 585                 590
Leu Met Pro Ser Leu Thr Glu Thr Lys Thr Thr Val Glu Leu Leu Pro
            595                 600                 605

Val Asn Gly Glu Phe Ser Leu Asp Asp Leu Gln Pro Trp His Ser Phe
        610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
            660                 665                 670

Ala Glu Phe Arg His Asp Ser Gly Tyr Glu Val His His Gln Lys Leu
            675                 680                 685

Val Phe Phe Ala Glu Asp Val Gly Ser Asn Lys Gly Ala Ile Ile Gly
        690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
                740                 745                 750

Gln Gln Asn Gly Tyr Glu Asn Pro Thr Tyr Lys Phe Phe Glu Gln Met
            755                 760                 765

Gln Asn
    770
```

BIOMARKERS AND METHODS RELATING TO ALZHEIMER'S DISEASE

CROSS-REFERENCE TO RELATED APPLICATIONS

This application is the U.S. National Stage Application of International Patent Application No. PCT/GB2014/053692, filed on Dec. 12, 2014, which claims priority to GB Application No. 1322094.2, filed on Dec. 13, 2013, the contents of each of which is incorporated herein by reference in its entirety.

FIELD OF THE INVENTION

The present invention relates to panels of markers that are differentially expressed in neurocognitive disorders, such as Alzheimer's disease, relative to the normal state. Further, the present invention provides methods of progression, prognosis and diagnosis of neurocognitive disorders using the panels of markers. Still further, the present invention provides methods for the identification of agents for the prevention and treatment of neurocognitive disorders using the panels of markers.

BACKGROUND OF THE INVENTION

Dementia is one of the major public health problems of the elderly, and in our ageing populations the increasing numbers of patients with dementia is imposing a major financial burden on health systems around the world. More than half of the patients with dementia have Alzheimer's disease (AD). The prevalence and incidence of AD have been shown to increase exponentially. The prevalence for AD in Europe is 0.3% for ages 60-69 years, 3.2% for ages 70-79 years, and 10.8% for ages 80-89 years. The survival time after the onset of AD is approximately from 5 to 12 years.

AD is the most common neurodegenerative disorder of the aging population; usually affecting people over the age of 65 years and resulting in a relentlessly progressive decline in cognition and function. Currently there is no cure. It destroys neurons in parts of the brain, chiefly the hippocampus, which is a region involved in coding memories. Alzheimer's disease gives rise to an irreversible progressive loss of cognitive functions and of functional autonomy. The earliest signs of AD may be mistaken for simple forgetfulness, but in those who are eventually diagnosed with the disease, these initial signs inexorably progress to more severe symptoms of mental deterioration. While the time it takes for AD to develop will vary from person to person, advanced signs include severe memory impairment, confusion, language disturbances, personality and behaviour changes, and impaired judgement. Patients with AD may become non-communicative and hostile. As the disease ends its course in profound dementia, patients are unable to care for themselves and often require institutionalisation or professional care in the home setting. While some patients may live for many years after being diagnosed with AD, the average life expectancy after diagnosis is eight years.

In the past, AD could only be definitively diagnosed by brain biopsy or upon autopsy after a patient died. These methods, which demonstrate the presence of the characteristic plaque and tangle lesions in the brain, are still considered the gold standard for the pathological diagnoses of AD. However, in the clinical setting brain biopsy is rarely performed and diagnosis depends on a battery of neurological, psychometric and biochemical tests, including the measurement of biochemical markers such as the ApoE and tau proteins or the beta-amyloid peptide in cerebrospinal fluid and blood.

Biomarkers may possibly possess the key in the next step for diagnosing AD and other dementias. A marker that fulfils the requirements for the diagnostic test for AD would have several advantages. An ideal marker would be one that identifies AD cases at a very early stage of the disease, before there is degeneration observed in the brain imaging and neuropathological tests. A biomarker could be the first indicator for starting treatment as early as possible, and also very valuable in screening the effectiveness of new therapies, particularly those that are focused on preventing the development of neuropathological changes. A marker would also be useful in the follow-up of the development of the disease.

Markers related to pathological characteristics of AD such as plaques and tangles (A$\beta$ and tau respectively) have been the most extensively studied. The most promising has been from studies of cerebrospinal fluid (CSF) concentration of the polypeptide fragments A$\beta$ (1-40), A$\beta$ (1-42) and tau or the combination of both proteins in AD. Many studies have reported a decrease in A$\beta$ (1-42) in CSF, while the total A$\beta$ protein or A$\beta$ (1-40) concentration remain unchanged.

Recognising that CSF samples are less desirable, there have been several efforts to identify protein markers in blood and blood products, such as serum and plasma. A group of such blood proteins that are differentially expressed in the AD state relative to their expression in the normal state are described in WO2006/035237. Whilst these proteins are proving useful in the development of new diagnostic and prognostic tests there remains a need for the discovery and validation of further panels of markers that may perform with superior sensitivity and/or specificity in the diagnosis and prognostic monitoring of patients with Alzheimer's disease and related dementias.

SUMMARY OF THE INVENTION

Accordingly, in a first aspect, the present invention provides for a biomarker panel consisting essentially of markers transthyretin (TTR), Clusterin, Cystatin C (CST3), Alpha-1-Acid glycoprotein (A1AcidG) Intercellular adhesion molecule 1 (ICAM1), Complement C4 (CC4), pigment epithelium derived factor (PEDF) and Alpha1 antitrypsin (A1AT).

In one embodiment, the panel further comprises markers regulated on activation, normal T cell expressed and secreted (RANTES) and Apolipoprotein C-III (ApoC3).

The panel may further comprise markers plasminogen activator inhibitor type 1 (PAI-1), C-reactive protein (CRP), Cathepsin D (CTSD) and apolipoprotein E (ApoE) and optionally, the panel may further comprise one or more of markers selected from the group consisting of alpha-2-macroglobulin (A2M), serum amyloid P component (SAP), advanced glycosylation end product-specific receptor (sRAGE), Neuron specific enolase (NSE), complement factor H (CFH), amyloid beta (A4) precursor protein (AB40 or A$\beta$40), Ceruloplasmin, neural cell adhesion molecule (NCAM), ApoA1, Abeta 42, BDNF, Beta-2-microglobulin (B2M), and VCAM-1.

In a further embodiment, the biomarker panel may further comprises ApoE ε4 allele presence (ApoE genotype).

In a second aspect, the present invention provides for a method for determining the progression and/or the prognosis of a neurocognitive disorder in a subject, the method comprising detecting markers of a biomarker panel as defined herein in a tissue sample and/or body fluid sample obtained from said subject.

In one embodiment of this second aspect the method comprises:
a) providing a tissue sample or body fluid sample obtained from said subject having a neurocognitive disorder or symptoms thereof at a test time point;
b) determining the amount or concentration of said markers of the biomarker panel as defined herein;
c) comparing the amount or concentration of said markers of the biomarker panel in the sample at the test time point with reference values;
wherein the test time point corresponds to time when the progression and/or prognostic method is carried out; and wherein the amount or concentration of said proteins in said sample is indicative of the progression and/or prognosis of the neurocognitive disorder in said subject.

Preferably, the amount or concentration of said markers in said sample is indicative of the progression and/or prognosis of the neurocognitive disease and/or the nature or degree of the neurocognitive disorder is determined.

The neurocognitive disorder may be mild cognitive impairment (MCI), Alzheimer's disease (AD), vascular dementia, dementia with lewy bodies, fronto-temporal dementia or any combinations thereof.

Preferably, the neurocognitive disorder is MCI or AD and the progression and/prognosis of the neurocognitive disease is the progression and/or prognosis of MCI or AD or the progression of the neurocognitive disorder is the conversion from MCI to AD.

More preferably, the conversion is determined over 12 months or less.

In a third aspect according to the invention there is provided method of diagnosing or assessing a neurocognitive disorder in a subject comprising detecting markers of a biomarker panel as defined herein in a tissue sample and/or body fluid sample obtained from said subject.

In one embodiment of this third aspect the method comprises:
a) providing a tissue sample or body fluid sample obtained from said subject having a neurocognitive disorder or symptoms thereof at a test time point;
b) determining the amount or concentration of said markers of the biomarker panel as defined herein;
c) comparing the amount or concentration of said markers of the biomarker panel in the sample with reference values;
wherein the test time point corresponds to time when the method of diagnosing is carried out; and wherein the amount or concentration of said markers in said sample is indicative of the presence or absence of the neurocognitive disorder in said subject.

Preferably, the amount or concentration of said markers in said sample is indicative of the neurocognitive disorder and/or the nature or degree of the neurocognitive disorder is determined.

The neurocognitive disorder may be mild cognitive impairment (MCI), Alzheimer's disease (AD), vascular dementia, dementia with lewy bodies, fronto-temporal dementia or any combinations thereof.

Preferably, the neurocognitive disorder is MCI or AD.

In one embodiment of this method, a change in the amount or concentration of said proteins in said sample is indicative of the progression to AD in a subject having MCI, wherein the progression from MCI to AD occurs over a period of 12 months or less.

In another embodiment, a change in the amount or concentration of said markers in said sample is indicative of the presence or extent of brain atrophy in said subject.

In yet another embodiment, the amount or concentration of said markers of the biomarker panel in the sample taken from a subject with a neurocognitive disorder are used to predict the most appropriate and effective therapy to alleviate the neurocognitive disorder and to monitor the success of that therapy.

In another embodiment, the markers of said biomarker panel are detected by a) using one or more binding agents to each said markers, or b) by detecting in the sample autoantibodies specific to each of said markers, or c) by mass spectrometry, or any combinations of a), b) and c). Preferably, the sample is immobilised on a solid support.

In yet another embodiment, the markers of the biomarker panel are detected using 2D gel electrophoresis.

In a fourth aspect, the present invention provides for a method of screening an agent for treating a neurocognitive disorder, the method comprising:
(a) providing a tissue sample or body fluid sample obtained from, or representative of, a subject having a neurocognitive disorder or symptoms thereof, wherein the subject and/or the sample has been treated with the agent being screened;
(b) determining the amount or concentration in the sample from, or representative of, the treated subject and/or sample of markers of a biomarker panel as defined herein; and
(c) determining whether the agent affects the amount or concentration of the markers of the biomarker panel in the treated subject and/or sample.

In one embodiment of this fourth aspect the amount or concentration of the markers of the biomarker panel in a subject treated with the agent compared to a subject not treated with the agent is indicative that the agent may be useful in treating a neurocognitive disorder.

In another embodiment, the method further comprises, prior to step (a), the step of determining the concentration or amount of the markers of the biomarker panel in one or more control samples from healthy individuals, patients having a neurocognitive disorder of differing severity or progression and patients having a neurocognitive disorder not treated with the agent.

In yet another embodiment, the agent is selected if prevents or slows the change over time of the amount or concentration of the markers of the biomarker panel relative to controls.

In a further embodiment the amount or concentration of said markers of the biomarker panel is determined in samples obtained from, or representative of:
(a) normal subjects and subjects having neurocognitive disorder symptoms; and/or,
(b) subjects with neurocognitive disorder symptoms which have not been treated with the agent and subjects with neurocognitive disorder symptoms which have been treated with the agent.

Preferably the subjects having neurocognitive disorder or symptoms thereof are human subjects with the neurocognitive disorder or a non-human animal model of the neurocognitive disorder. More preferably the neurocognitive disorder is AD.

In some embodiments the subjects are mutant amyloid precursor protein (APP) transgenic mice, presenilin-1 (PS-1) transgenic mice, double transgenic APP/PS-1 transgenic mice and/or glycogen synthase kinase transgenic mice, and the normal subjects are wild-type mice.

In the embodiments of the methods according to the invention the tissue or body fluid samples are preferably urine, blood, plasma, serum, saliva or cerebro-spinal fluid samples.

In a fifth aspect, the present invention provides for a kit comprising reagents for the detection of markers of a biomarker panel in a tissue sample or body fluid sample, wherein said biomarker panel is as defined herein.

In one embodiment the kit further comprises one or more binding agents which specifically bind to the markers of the biomarker panels.

Preferably, the one or more binding agent are primary antibodies, wherein each primary antibody specifically binds to a different markers of the biomarker panel and more preferably, the kit further comprises one or more secondary antibodies which specifically bind to the primary antibodies.

Optionally, the secondary antibodies are labeled.

In another embodiment the kit further comprises control samples of the markers on the biomarker panel.

DETAILED DESCRIPTION

Definitions

The term "neurocognitive disorders" is used herein as a synonym of "neurocognitive diseases" and includes, but is not limited to, Alzheimer's Disease (AD) which is the main representative example of all related dementias and neurocognitive disorders. References to AD may therefore be equally taken as references to Mild Cognitive Impairment (MCI) (a recognised precursor to AD) and other late onset dementias including vascular dementia, dementia with lewy bodies and fronto-temporal dementia, alone and as a mixed dementia with Alzheimer's disease, unless it is explicitly specified the progression between MCI and AD. It may also refer to a specific diagnosis given to a subject or it may also include symptoms of that neurocognitive disorders where a specific diagnosis has not been yet formalised by a medical practitioner according to the present clinical assessment measures. Currently, the disease status is assessed by duration of disease from inception to present (longer duration equals more severe disease) and clinical assessment measures. These assessment measures include clinical tests for memory and other cognitions, clinical tests for function (abilities of daily living) and clinical assessments of global severity. Trials of potential therapies in AD and other dementias and neurocognitive disorders are currently evaluated against these measures. The FDA and other regulatory authorities require as part of these assessments measures of both cognition and global function. The Global Dementia Scale is one such measure of global function. It is assessed by assessment of severity including cognition and function against a standardised set of severity criteria.

The term "biomarkers panel" is used herein interchangeably with the term "marker panel" and includes all biologically relevant forms of the protein identified, including post-translational modifications. For example, the protein in the biomarkers panel can be present in a glycosylated, phosphorylated, multimeric, fragmented or precursor form. It further includes deoxyribonucleic acid (DNA) and ribonucleic acid (RNA) products resulting from the gene codifying such proteins, such as cDNA, mRNA and fragments thereof.

The term "relevant tissue" means any tissue involved in brain function, in particular tissue which is affected in AD.

The terms "tissue or body fluid sample" or "representative of a tissue or body fluid sample" mean any tissue or body fluid in which the detection of the markers can be carried out and includes, for example, blood, serum, plasma, CSF, a primary cell culture or a biopsy from the relevant tissue.

The term "subjects" includes human and non-human animal subjects.

The term "differential expression", as used herein, refers to both qualitative and quantitative differences in markers' transcription and/or expression and indicates that a marker may be present at different levels in samples from normal and diseased subjects. The term further refers to at least one recognisable difference of marker expression in a tissue or body fluid sample. It may be a quantitatively measurable, semi-quantitatively estimable or a qualitatively detectable difference of marker expression in tissue or body fluid sample.

The term "differentially expressed marker"(or DEM) refers to a marker which may be strongly expressed in tissues or body fluids in the normal state and less strongly expressed or not expressed at all in tissues in AD. Conversely, it may be strongly expressed in tissues in AD and less strongly expressed or not expressed at all in normal samples. Further, expression may be regarded as differential if the marker undergoes any recognisable change between the samples under comparison.

The term differentially expressed markers (DEMs) includes "fingerprint proteins", "target proteins" or "pathway proteins".

"Fingerprint protein", as used herein, means a DEM, the expression of which can be used, alone or together with other DEMs, to monitor or assess the condition of a patient suspected of suffering from AD. Since these proteins will normally be used in combination, especially a combination of four or more, they are conveniently termed "fingerprint proteins", without prejudice to the possibility that on occasions they may be used singly or along with only one or two other proteins for this purpose. Such a fingerprint protein or proteins can be used, for example, to diagnose a particular type of AD and hence to indicate a specific treatment for it.

"Target protein", as used herein, means a DEP, the level or activity of which can be modulated by treatment to alleviate AD or other dementias and neurocognitive disorders. Modulation of the level or activity of the target protein in a patient may be achieved, for example, by administering the target protein, another protein or gene which interacts with it or an agent which counteracts or reduces it, for example an antibody to the protein, competitive inhibitor of the protein or an agent which acts in the process of transcription or translation of the corresponding gene.

"Pathway protein", as used herein, means proteins that can interact with at least one other protein or with a gene involved in the regulation of brain function. The term is for the protein with which the DEP interacts, not to the DEP itself, although a pathway protein can be another DEP.

It is further contemplated herein that a "fingerprint protein" may also be a "target protein" or a "pathway protein" and vice versa.

The term "detectable", as used herein, refers to a marker transcription and/or expression pattern, which are detectable using techniques described herein.

The term "control" refers to a tissue sample or a bodily fluid sample taken from a human or non-human subject not diagnosed or not presenting any symptoms of a neurocognitive disorder or disease.

The term "isolated" means throughout this specification, that the marker, antibody or polynucleotide, as the case may be, exists in a physical milieu distinct from that in which it may occur in nature.

The term "treat", "treating", "treatment", "prevent", "preventing" "prevention" or "alleviation" includes therapeutic treatments, prophylactic treatments and applications in which one reduces the risk that a subject will develop a disorder or other risk factors. Treatment does not require the complete curing of a disorder and encompasses the reduction of one or more symptoms or underlying risk factors. Treatment may also include slowing down the progression of the disease and may comprise the administration of one or more drugs or foodstuffs, and/or other factors such as diet or exercise.

The term "diagnosis", as used herein, includes the provision of any information concerning the existence or presence, non-existence or absence or probability of the disorder in a patient. It further includes the provision of information concerning the type or classification of the disorder or of symptoms which are or may be experienced in connection with it. This may include, for example, diagnosis of the severity of the disorder. It encompasses prognosis of the medical course of the disorder, for example its duration, severity and the course of progression from MCI to AD or other dementias.

The term "efficacy" indicates the capacity for beneficial change of a given intervention (e.g. a drug, medical device, surgical procedure, etc.). If efficacy is established, that intervention is likely to be at least as good as other available interventions, to which it will have been compared. The term "efficacy" and "effectiveness" are used herein interchangeably.

The term "comprising" indicates that the subject includes all the elements listed, but may, optionally, also include additional, unnamed elements (i.e. open).

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless the context dictates otherwise, the definitions of the features/terms set out above are not limited to any particular aspect or embodiment of the invention and apply equally to all aspects and embodiments which are described herein.

Biomarker Panels and Methods of Using Thereof

The present invention relates to biomarkers panels of markers that are differentially expressed in neurocognitive disorders, such as MCI and AD, relative to each other and/or their expression in the normal state. These panels allow for the improved detection and assessment of neurocognitive disorders.

The biomarker panel according to the invention consists essentially of markers transthyretin (TTR), Clusterin, Cystatin C (CST3), Alpha-1-Acid glycoprotein (A1AcidG), Intercellular adhesion molecule 1 (ICAM1), Complement C4 (CC4), pigment epithelium derived factor (PEDF) and Alpha1 antitrypsin (A1AT).

The biomarker panel may further comprise markers regulated on activation, normal T cell expressed and secreted (RANTES) and Apolipoprotein C-III (ApoC3).

The biomarker panel may also further comprises markers plasminogen activator inhibitor type 1 (PAI-1), C-reactive protein (CRP), Cathepsin D (CTSD) and apolipoprotein E (ApoE).

In addition, the biomarker panel may further comprise one or more of markers selected from the group consisting of alpha-2-macroglobulin (A2M), serum amyloid P component (SAP), advanced glycosylation end product-specific receptor (sRAGE), Neuron specific enolase (NSE), complement factor H (CFH), amyloid beta (A4) precursor protein (AB40 or Aβ40), Ceruloplasmin, neural cell adhesion molecule (NCAM), ApoA1, Abeta 42, BDNF, Beta-2-microglobulin (B2M), and VCAM-1.

In one embodiment the biomarker panel consists essentially of markers transthyretin (TTR), Clusterin, Cystatin C (CST3), Alpha-1-Acid glycoprotein (A1AcidG), Intercellular adhesion molecule 1 (ICAM1), Complement C4 (CC4), pigment epithelium derived factor (PEDF) and Alpha1 antitrypsin (A1AT), optionally in combination with ApoE ε4 allele presence (ApoE genotype). The ApoE ε4 allele presence includes both the genetic presence of the ε4 allele, detectable as a genetic marker, as well as the protein presence of the specific ApoE E4 (S112R and H158R).

In another embodiment the biomarker panel consists essentially of markers transthyretin (TTR), Clusterin, Cystatin C (CST3), Alpha-1-Acid glycoprotein (A1AcidG), Intercellular adhesion molecule 1 (ICAM1), Complement C4 (CC4), pigment epithelium derived factor (PEDF) and Alpha1 antitrypsin (A1AT), wherein the biomarker panel further comprises regulated on activation, normal T cell expressed and/or secreted (RANTES) and Apolipoprotein C-III (ApoC3), optionally in combination with ApoE ε4 allele presence (ApoE genotype).

In yet another embodiment the biomarker panel consists essentially of markers transthyretin (TTR), Clusterin, Cystatin C (CST3), Alpha-1-Acid glycoprotein (A1AcidG), Intercellular adhesion molecule 1 (ICAM1), Complement C4 (CC4), pigment epithelium derived factor (PEDF) and Alpha1 antitrypsin (A1AT), regulated on activation, normal T cell expressed and secreted (RANTES) and Apolipoprotein C-III (ApoC3), wherein the biomarker panel further comprises one or more of markers selected from the group of plasminogen activator inhibitor type 1 (PAI-1), C-reactive protein (CRP), Cathepsin D (CTSD) and apolipoprotein E (ApoE), optionally in combination with ApoE ε4 allele presence (ApoE genotype).

In a further embodiment the biomarker panel consists essentially of markers transthyretin (TTR), Clusterin, Cystatin C (CST3), Alpha-1-Acid glycoprotein (A1AcidG), Intercellular adhesion molecule 1 (ICAM1), Complement C4 (CC4), pigment epithelium derived factor (PEDF) and Alpha1 antitrypsin (A1AT), regulated on activation, normal T cell expressed secreted (RANTES), Apolipoprotein C-III (ApoC3), plasminogen activator inhibitor type 1 (PAI-1), C-reactive protein (CRP), Cathepsin D (CTSD) and apolipoprotein E (ApoE), wherein the biomarker panel further comprises one or more of markers selected from the group of alpha-2-macroglobulin (A2M), serum amyloid P component (SAP), advanced glycosylation end product-specific receptor (sRAGE), Neuron specific enolase (NSE), complement factor H (CFH), amyloid beta (A4) precursor protein (AB40 or Aβ40), Ceruloplasmin, neural cell adhesion molecule (NCAM), ApoA1, Abeta 42, BDNF, Beta-2-microglobulin (B2M), and VCAM-1, optionally in combination with ApoE ε4 allele presence (ApoE genotype).

The proteins in the biomarker panel according to the invention are indicated in Table 1A below.

TABLE 1A

| Protein Name | Method | Study design | Reported findings | References |
|---|---|---|---|---|
| Alpha-2-macroglobulin (A2M) | 2-DGE; LC-MS/MS | AD v Control | ↑ AD | Hye et al. 2006 |
| Serum amyloid P component (SAP) | 2-DGE; LC-MS/MS | AD v Control | ↑ AD | Hye et al. 2006 |
| Complement factor H (CFH) | 2-DGE; LC-MS/MS | AD v Control | ↑ AD | Hye et al. 2006; Cutler et al. 2008 |
| Complement C4 (CC4) | 2-DGE; LC-MS/MS | AD v Control | ↓ AD | Hye et al. 2006 |
| Apolipoprotein E (ApoE) | 2-DGE; LC-MS/MS and ELISA | PiB PET association | ↑ Aβ brain region | Thambisetty et al. 2010 |
| Clusterin | 2-DGE; LC-MS/MS and ELISA | Low v high brain atrophy | ↑ High atrophy | Thambisetty et al. 2011 |
| Apolipoprotein (ApoA1) | 2-DGE; LC-MS/MS | SCD v FCD | ↑ FCD | Thambisetty et al. 2011 |
| Transthyretin (TTR) | 2-DGE; LC-MS/MS and ELISA | SCD v FCD | ↓ FCD | Velayudhan et al. 2012 |
| Ceruloplasmin | 2-DGE; LC-MS/MS | AD v Control | ↓ AD | Hye et al. 2006 |
| Amyloid beta (A4) precursor protein (AB 40) (Aβ40) | ELISA | AD v Control | ↑ AD | Mehta et al. 2001, Mayeux et al. 2003 |
| Amyloid beta protein 1-42 fragment (Abeta 42) | ELISA | AD v Control | ↓ AD | Hampel et al. 2010, Blennow et al. 2001 |
| Alpha-1-Acid Glycoprotein (A1AcidG) | ELISA | AD v Control | ↓ AD | Roher et al. 2010 |
| Alpha1 antitrypsin (A1AT) | ELISA | AD v Control | ↑ AD | Nielsen et al. 2007; Sun et al. 2003 |
| Apolipoprotein C-III (Apo C3) | Luminex | ε4 carrier v non-carrier | ↓ AD | Song et al. 2012 |
| Brain Derived neurotrophic factor (BDNF) | ELISA | MRI association | ↑ Age related white atrophy | Driscoll et al. 2011 |
| | ELISA | AD v Control | ↓ AD | Aisa et al. 2010 |
| | ELISA | AD v Control | ↓ AD | Laske et. 2006 |
| Beta-2-microglobulin | Luminex | | ↑ AD | Wilson et al. 2012 |
| Cathepsin D | Western blot | AD v Control | ↓ AD | Urbanelli et al. 2008 |
| C-reactive protein (CRP) | Nephalometric detection | SCD v FCD | ↑ FCD | Locascio et al. 2008 |
| Cystatin C | Immunoturbidimetric assay | AD v Control | ↓ AD | Zhong et al. 2013; |
| | ELISA | AD v Control | No change | Sundelöf et al. 2010 |
| Intracellular adhesion molecule 1 (ICAM-1) | IHC | AD v Control | ↑ AD | Frohman et al. 1991 |
| Neural cell adhesion molecule (NCAM) | ELISA | AD v Control | ↓ AD | Aisa et al. 2010 |
| Neuron specific enolase (NSE) | Electrochemiluminescence assay | AD v Control | No change | Chaves et al. 2010; |
| | Immunoradiometric assay | AD v Control | ↑ AD | Blennow et al. 1994 |
| Plasminogen activator inhibitor 1 (PAI-1) | ELISA | AD v Control | ↑ AD | Sutton et al. 1994; Akenami et al. 1997 |
| Pigment epithelium derived factor (PEDF) | 2-DGE; LC-MS/MS | AD v Control | ↑ AD | Castano et al. 2006 |
| Regulated on activation, normal T cell expressed and secreted (RANTES) | Q-RT-PCR | AD v Control | ↓ AD<br>↑ AD | Kester et a., 2011<br>Tripathy et al. 2011; Reynolds et al. 2007 |

TABLE 1A-continued

Overview of proteins investigated in the current study

| Protein Name | Method | Study design | Reported findings | References |
|---|---|---|---|---|
| Vascular cell adhesion molecule 1 (VCAM-1) | ELISA | AD v Control | ↑ AD | Zuliani et al. 2008 |
| Advanced glycosylation end product-specific receptorsRAGE | ELISA ELISA | AD v Control AD vs. MCI | ↓AD ↓MCI | Emanuele et al. 2005 Chidoni et al. 2008 |

Abbreviations:
PiB PET association, Philadelphia Compound B Positron Emission Tomography;
2-DGE, two-dimensional gel electrophoresis;
LC-MS/MS, liquid chromatography tandem mass spectrometry;
ELISA, Enzyme-linked immunosorbent assay;
Q-RT-PCR, quantitative Reverse transcription polymerase chain reaction;
IHC, Immunohistochemistry;
SCD, slow cognitive decline;
FCD, fast cognitive decline.

Reference sequences for these proteins are provided in SEQ ID NOS: 1 to 27 according to Table 1B.

TABLE 1B

Sequence correlation table

| Protein | SEQ ID NO: |
|---|---|
| Transthyretin (TTR) | 1 |
| Clusterin | 2 |
| Cystatin C (CST3) | 3 |
| Alpha-1-Acid glycoprotein (A1AcidG) | 4 |
| Intercellular adhesion molecule 1 (ICAM 1) | 5 |
| Complement C4 (CC4) | 6 |
| Pigment epithelium derived factor (PEDF) | 7 |
| Alpha1 antitrypsin (A1AT) | 8 |
| RANTES | 9 |
| Apolipoprotein C-III (ApoC3) | 10 |
| Plasminogen activator inhibitor type 1 (PAI-1) | 11 |
| C-reactive protein (CRP) | 12 |
| Cathepsin D (CTSD) | 13 |
| Apolipoprotein E (ApoE) | 14 |
| Alpha-2-macroglobulin (A2M) | 15 |
| Serum amyloid P component (SAP) | 16 |
| Neuron specific enolase (NSE) | 17 |
| Complement factor H (CFH) | 18 |
| Amyloid beta (A4) precursor protein (AB40 or Aβ40) | 19 |
| Ceruloplasmin | 20 |
| Neural cell adhesion molecule (NCAM) | 21 |
| ApoA1 | 22 |
| BDNF | 23 |
| Beta-2-microglobulin (B2M) | 24 |
| VCAM-1 | 25 |
| Advanced glycosylation end product-specific receptor (sRAGE) | 26 |
| Abeta42 | 27 |

In any individual subject, the sequence of a protein in the biomarker panel may be the reference sequence or an allele or natural variation of the reference sequence.

An allele or natural variation may have 80% or more, 90% or more, 95% or more or 98% or more sequence identity with a reference sequence over its full length. Sequence identity may be commonly defined with reference to the algorithm GAP (Genetics Computer Group, Madison, WI). GAP uses the Needleman and Wunsch algorithm to align two complete sequences that maximizes the number of matches and minimizes the number of gaps. Generally, default parameters are used, with a gap creation penalty=12 and gap extension penalty=4. Use of GAP may be preferred but other algorithms may be used, e.g. BLAST[63], FASTA[64], or the Smith-Waterman algorithm, or the TBLASTN program[63], generally employing default parameters.

An allele or natural variation may differ from the reference sequence by the addition, deletion, substitution and/or insertion of one or more amino acids. For example, an allele or natural variation may differ from the reference sequence described herein (e.g SEQ ID Nos: 1 to 27) by addition, deletion or substitution of 1 or more amino acids, for example, up to 2, up to 5 amino acids, up to 10 amino acids, or up to 20 amino acids. A natural variation as defined herein also include post-translational modifications such as phosphorylation and glycosylation.

The expression of some markers in the panels described herein may be increased in subjects with a neurocognitive disorder as compared to control subjects or may be uniquely present in subjects with a neurocognitive disorder as compared to control subjects. The expression of other markers in the panels described herein may be decreased in subjects with neurocognitive disorder as compared to control subjects or may be uniquely absent in subjects with a neurocognitive disorder as compared to control subjects. Table 1 indicates whether the expression of the proteins disclosed therein is increased or decreased in disease versus control subjects.

Biomarker panels as described herein may be employed for monitoring progression of neurocognitive disorders such as mild cognitive impairment and AD, the predisposition to neurocognitive disorders such as AD, for the diagnosis of neurocognitive disorders such as AD, and for monitoring the efficacy of an agent during, for example, clinical trials and for monitoring patients undergoing clinical evaluation for the treatment of neurocognitive disorders such as AD. Biomarker panels as described herein can be used to precisely define the nature or degree of the neurocognitive disorder to aid in the identification and/or selection of treatments for the disorder.

AD, for example, is characterised by a progressive, insidious onset, two or more deficits in cognitive function, and the absence of any other illnesses that could account for the dementia.

In addition to memory loss, there may be disorientation, poor attention span, and language impairment. There is likely to be a decline in the activity of daily living, and possibly also impaired perception and personality changes.

Behavioural symptoms include delusions, aggression, agitation, anger, wandering, hallucinations, and sleep disturbance.

A simple test assessing orientation, registration, calculations and attention, recall, language, and visual-spatial function may be used for an initial diagnosis.

Structural imaging by standard CT or MRI may also be used. Typically a non-contrast head CT scan suffices, but MRI is preferred for those who have hypertension or diabetes, who are at risk for cerebral vascular disease.

AD may be confirmed histologically by autopsy or brain biopsy showing neurofibrillary tangles and senile plaques.

Identifying individuals at risk from AD or other neurocognitive disorder may involve diagnosis of mild cognitive impairment (MCI). (MCI) may be a transitional state between normal aging and dementia. There are different types of MCI. There may be cognitive impairment in multiple areas of cognitive function, in addition to memory. In some cases, memory is normal but some other domain of cognitive function is abnormal.

Amnestic MCI appears to be a risk state for the development of AD. Amnestic impairment is defined by subjective memory complaints. These patients have poor memory performance for their age and education on formal testing when compared to age-matched peers. General cognitive functions and the ability to perform the activities of daily living should be entirely normal. The amnestic type of MCI is associated with hippocampal atrophy, neurofibrillary tangles in the medial temporal lobes, and elevated levels of Tau in the cerebrospinal fluid (CSF).

In particular, the present invention provides for a method for determining the progression and/or the prognosis of a neurocognitive disorder in a subject comprising detecting markers of a biomarker panel as defined herein in a tissue sample and/or body fluid sample obtained from said subject.

Preferably the method is an in vitro method.

In details, the method may comprises:
a) providing a tissue sample or body fluid sample obtained from said subject having a neurocognitive disorder or symptoms thereof at a test time point;
b) determining the amount or concentration of said markers of the biomarker panel;
c) comparing the amount or concentration of said markers of the biomarker panel in the sample at the test time point with reference values;

wherein the test time point corresponds to time when the progression and/or prognostic method is carried out; and wherein the amount or concentration of said proteins in said sample is indicative of the progression and/or prognosis of the neurocognitive disorder in said subject and wherein the biomarker panel consists essentially of markers transthyretin (TTR), Clusterin, Cystatin C (CST3), Alpha-1-Acid glycoprotein (A1AcidG), Intercellular adhesion molecule 1 (ICAM1), Complement C4 (CC4), pigment epithelium derived factor (PEDF) and Alpha1 antitrypsin (A1AT), optionally in combination with ApoE ε4 allele presence (ApoE genotype).

The reference values may have been obtained from a large screening of patients, like the one carried out for the present study, by reference to a known or previously determined correlation between such a determination and clinical information in control patients. For example, the reference values may be determined by comparison to the concentration, amount or level of expression of the said markers in a control subject, for example a healthy person (i.e. without dementia) of similar age and gender as the subject. Alternatively, the reference values are value which can be found in literature such as the ApoE ε4 allele presence whereby the presence or absence of the mutations at position 112 and 158 represent the reference to be compared to. In addition, the reference values may have been obtained from the same subject at one or more time points which precede in time the test time point. Such earlier sample may be taken one week or more, one month or more, three months or more, most preferably six months or more before the date of the test time point. In some embodiments, multiple earlier samples may be compared in a longitudinal manner and the slope of change in marker expression may be calculated as a correlate of cognitive decline.

The neurocognitive disorder may be selected from the group consisting of mild cognitive impairment (MCI), Alzheimer's disease (AD), vascular dementia, dementia with lewy bodies, fronto-temporal dementia or combinations thereof.

Preferably the neurocognitive disorder is MCI or AD and the progression and/prognosis of the neurocognitive disease is the progression and/or prognosis of MCI or AD.

In a preferred embodiment, the method comprises:
a) providing a tissue sample or body fluid sample obtained from said subject having a neurocognitive disorder or symptoms thereof at a test time point;
b) determining the amount or concentration of said markers of the biomarker panel;
c) comparing the amount or concentration of said markers of the biomarker panel in the sample at the test time point with reference values;

wherein the test time point corresponds to time when the progression and/or prognostic method is carried out; and wherein the amount or concentration of said proteins in said sample is indicative of conversion of MCI to AD in said subject and wherein the biomarker panel consists essentially of markers transthyretin (TTR), Clusterin, Cystatin C (CST3), Alpha-1-Acid glycoprotein (A1AcidG), Intercellular adhesion molecule 1 (ICAM1), Complement C4 (CC4), pigment epithelium derived factor (PEDF) and Alpha1 antitrypsin (A1AT), optionally in combination with ApoE ε4 allele presence (ApoE genotype).

Preferably, the conversion is determined over 12 months or less.

More preferably, the biomarker panel also comprises regulated on activation, normal T cell expressed and secreted (RANTES) and Apolipoprotein C-III (ApoC3).

The reference values derived in the present studies for the conversion of MCI to AD are the following: transthyretin 222 μg/ml; Clusterin 402 μg/ml; Cystatin C 3.21 μg/ml; Alpha-1-Acid glycoprotein 768.3 μg/ml; Intercellular adhesion molecule 1 99.72 ng/ml; Complement C4 78.5 μg/ml; pigment epithelium derived factor 10.7 μg/ml; Alpha1 antitrypsin 9.5 μg/ml; RANTES 33.8 ng/ml; and Apolipoprotein C-III 105.5 μg/ml.

In particular, MCI to AD conversion may be expected when the concentration of at least some of these markers is as following: transthyretin less (<) than 222 μg/ml; Clusterin more (>) than 402 μg/ml; Cystatin C less (<) than 3.21 μg/ml; Alpha-1-Acid glycoprotein more (>) than 768.3 μg/ml; Intercellular adhesion molecule 1 less (<) than 99.72 ng/ml; Complement C4 more (>) than 78.5 μg/ml; pigment epithelium derived factor more (>) than 10.7 μg/ml; Alpha1 antitrypsin less (<) than 9.5 μg/ml; RANTES less (<) than 33.8 ng/ml; and Apolipoprotein C-III less (<) than 105.5 μg/ml.

In addition, it may be that not all of the markers in the biomarker panels are differentially expressed within an individual subject. The number and identity of the differentially expressed markers seen in any individual test will vary between different subjects and between samples taken from an individual subject over time. Within each subset panel, a minimum number of differentially expressed proteins may be required to provide a secure determination. For example, three or more proteins in the panel, preferably four or more, and more preferably five or more, six or more, seven or more or eight or more proteins in the panel may be differentially expressed in an individual subject.

In one preferred embodiment, the method for determining the progression and/or the prognosis of a neurocognitive disorder in a subject comprises detecting markers of a biomarker panel in a tissue sample and/or body fluid sample obtained from said subject, wherein the method comprises:
  a) providing a tissue sample or body fluid sample obtained from said subject having a neurocognitive disorder or symptoms thereof at a test time point;
  b) determining the amount or concentration of said markers of the biomarker panel;
  c) comparing the amount or concentration of said markers of the biomarker panel in the sample at the test time point with reference values;
wherein the test time point corresponds to time when the progression and/or prognostic method is carried out; and wherein the amount or concentration of said proteins in said sample is indicative of the progression and/or prognosis of the neurocognitive disorder in said subject and wherein the biomarker panel consists essentially of markers transthyretin (TTR), Clusterin, Cystatin C (CST3), Alpha-1-Acid glycoprotein (A1AcidG), Intercellular adhesion molecule 1 (ICAM1), Complement C4 (CC4), pigment epithelium derived factor (PEDF), Alpha1 antitrypsin (A1AT), regulated on activation, normal T cell expressed and secreted (RANTES) and Apolipoprotein C-III (ApoC3) in combination with ApoE ε4 allele presence (ApoE genotype); wherein the progression and/or prognosis of the neurocognitive disorder is the conversion from MCI to AD; and wherein the method is an in vitro method.

More preferably the subject is human; even more preferably the sample is blood, plasma or serum.

The most preferred embodiment is an vitro method for determining the progression and/or the prognosis of MCI to AD in a human subject which comprises determining at testing point in a blood sample obtained from said human subject, the concentration of markers transthyretin (TTR), Clusterin, Cystatin C (CST3), Alpha-1-Acid glycoprotein (A1AcidG), Intercellular adhesion molecule 1 (ICAM1), Complement C4 (CC4), pigment epithelium derived factor (PEDF), Alpha1 antitrypsin (A1AT), regulated on activation, normal T cell expressed and secreted (RANTES) and Apolipoprotein C-III (ApoC3) in combination with ApoE ε4 allele presence (ApoE genotype); and wherein when at least three or more of the markers have their concentrations as following: transthyretin less (<) than 222 μg/ml; Clusterin more (>) than 402 μg/ml; Cystatin C less (<) than 3.21 μg/ml; Alpha-1-Acid glycoprotein more (>) than 768.3 μg/ml; Intercellular adhesion molecule 1 less (<) than 99.72 ng/ml; Complement C4 more (>) than 78.5 μg/ml; pigment epithelium derived factor more (>) than 10.7 μg/ml; Alpha1 antitrypsin less (<) than 9.5 μg/ml; RANTES less (<) than 33.8 ng/ml; and Apolipoprotein C-III less (<) than 105.5 μg/ml, then the human subject will convert from MCI to AD within 12 months from testing point.

The markers of the biomarker panel as described herein may also be present as fragments. Preferred fragments are less than 50, less than 100, less than 150 less than 200, less than 250, less than 300, less than 350, less than 400, less than 500, less than 600, less than 700, less than 800, less than 900, less than 1000, less than 1100, less than 1200, less than 1300, less than 1400, less than 1500, less than 1600, less than 1700, less than 1800, less than 1900 or less than 2000 amino acids in length.

The amount or concentration of the markers in the sample is indicative of the progression and/or prognosis of the neurocognitive disease.

Alternatively, the nature or degree of the neurocognitive disorder may be determined.

The present invention further comprises a method of diagnosing or assessing a neurocognitive disorder in a subject comprising detecting markers of a biomarker panel as defined herein in a tissue sample and/or body fluid sample obtained from said subject.

In particular the method comprises:
  a) providing a tissue sample or body fluid sample obtained from said subject having a neurocognitive disorder or symptoms thereof at a test time point;
  b) determining the amount or concentration of said markers of the biomarker panel;
  c) comparing the amount or concentration of said markers of the biomarker panel in the sample with reference values;
wherein the test time point corresponds to time when the method of diagnosing is carried out; and wherein the amount or concentration of said markers in said sample is indicative of the presence or absence of the neurocognitive disorder in said subject; wherein the biomarker panel consists essentially of markers transthyretin (TTR), Clusterin, Cystatin C (CST3), Alpha-1-Acid glycoprotein (A1AcidG), Intercellular adhesion molecule 1 (ICAM1), Complement C4 (CC4), pigment epithelium derived factor (PEDF) and Alpha1 antitrypsin (A1AT), optionally in combination with ApoE ε4 allele presence (ApoE genotype).

Preferably, the biomarker panel further comprises regulated on activation, normal T cell expressed and/or secreted (RANTES) and Apolipoprotein C-III (ApoC3), optionally in combination with ApoE ε4 allele presence (ApoE genotype).

Alternatively, the biomarker panel consists essentially of markers transthyretin (TTR), Clusterin, Cystatin C (CST3), Alpha-1-Acid glycoprotein (A1AcidG), Intercellular adhesion molecule 1 (ICAM1), Complement C4 (CC4), pigment epithelium derived factor (PEDF) and Alpha1 antitrypsin (A1AT), regulated on activation, normal T cell expressed and secreted (RANTES) and Apolipoprotein C-III (ApoC3), and further comprises one or more of markers selected from the group of plasminogen activator inhibitor type 1 (PAI-1), C-reactive protein (CRP), Cathepsin D (CTSD) and apolipoprotein E (ApoE), optionally in combination with ApoE ε4 allele presence (ApoE genotype).

In a further embodiment the biomarker panel consists essentially of markers transthyretin (TTR), Clusterin, Cystatin C (CST3), Alpha-1-Acid glycoprotein (A1AcidG), Intercellular adhesion molecule 1 (ICAM1), Complement C4 (CC4), pigment epithelium derived factor (PEDF) and Alpha1 antitrypsin (A1AT), regulated on activation, normal T cell expressed secreted (RANTES), Apolipoprotein C-III (ApoC3), plasminogen activator inhibitor type 1 (PAI-1), C-reactive protein (CRP), Cathepsin D (CTSD) and apolipoprotein E (ApoE), and further comprises one or more of markers selected from the group of alpha-2-macroglobulin (A2M), serum amyloid P component (SAP), advanced glycosylation end product-specific receptor (sRAGE), Neuron specific enolase (NSE), complement factor H (CFH), amyloid beta (A4) precursor protein (AB40 or Aβ40), Ceruloplasmin, neural cell adhesion molecule (NCAM), ApoA1, Abeta 42, BDNF, Beta-2-microglobulin (B2M), and VCAM-1, optionally in combination with ApoE ε4 allele presence (ApoE genotype).

In one embodiment of this method, the amount or concentration of said markers in said sample is indicative of the neurocognitive disorder and/or the nature or degree of the neurocognitive disorder is determined.

The neurocognitive disorder may be selected from the group consisting of mild cognitive impairment (MCI), Alzheimer's disease (AD), vascular dementia, dementia with lewy bodies, fronto-temporal dementia or combinations thereof.

Preferably the neurocognitive disorder is MCI or AD. More preferably a change in the amount or concentration of said proteins in said sample is indicative of the progression to AD in a subject having MCI, wherein the progression from MCI to AD occurs over a period of 12 months or less.

The methods described herein allows the type or sub-type of neurocognitive disorder in a subject to be correlated to different types to prophylactic or therapeutic treatment available in the art, thereby enhancing the likely response of the subject to the therapy.

In particular, the amount or concentration of said markers of the biomarker panel in the sample taken from a subject with a neurocognitive disorder are used to predict the most appropriate and effective therapy to alleviate the neurocognitive disorder and to monitor the success of that therapy.

The sample used in the methods of the invention can be a tissue sample or body fluid sample such as urine, blood, plasma, serum, saliva or cerebro-spinal fluid sample. Preferably the sample is a blood, serum or plasma sample. Use of body fluids such as those listed is preferred because they can be more readily obtained from a subject. This has clear advantages in terms of cost, ease, speed and subject well-being. Blood, blood products such as serum and plasma, and urine are particularly preferred.

Following assessment or diagnosis by the methods described herein, a subject may undergo further tests, for example cognitive tests and/or brain imaging, such as positron emission tomography (PET) scans.

The progression of the disorder over time may be tracked using methods of the invention to determine the severity of the disorder (e.g. global dementia severity).

The biomarker panel according to the invention may be used in combination with or as a replacement for other clinical assessments of cognitive decline in patients undergoing treatment as part of a clinical trial or in standard clinical management.

In one embodiment, the biomarkers panels may be useful as a surrogate for a clinical assessment, such as Mini Mental State Examination (MMSE) and AD Assessment Scale—Cognitive subscale (ADAS-cog).

In some embodiments, the biomarker panel may comprise one or more of the prognostic biomarkers Clusterin, RANTES, NSE, TTR, VCAM-1 and SAP; or NCAM, sRAGE and ICAM and the amount of said prognostic biomarkers in the sample may be indicative of MMSE performance of the subject and/or the severity, progression or prognosis of AD in the subject. The biomarkers panel may for example be used in combination with or as a replacement for MMSE in patients undergoing treatment as part of a clinical trial or in standard clinical management.

In some other embodiments, the biomarker panel may comprise one or more of the prognostic biomarkers APOA1, A1AT, ApoC3, BDNF, AB40, PAI-1 and NSE and the amount of said prognostic biomarkers in the sample is indicative of the ADAS-Cog performance of the subject and/or the severity, progression or prognosis of AD in the subject. The biomarker panel may, for example, be used in combination with or as a replacement for ADAS-Cog in patients undergoing treatment as part of a clinical trial or in standard clinical management.

Alternatively, a change in the amount or concentration of said markers in said sample is indicative of the presence or extent of brain atrophy in said subject.

The amount or concentration in sample of the atrophy biomarkers may be indicative of the presence or extent of brain atrophy in the subject. Such biomarkers panel may be used, for example, in combination with or as a replacement for brain imaging in patients undergoing treatment as part of a clinical trial or in standard clinical management.

Individual markers of the biomarkers panels may be useful in determining the presence or extent of atrophy in specific brain regions in the subject.

For example (see Table 4 below) in a subject having MCI:
Individual markers Clusterin and/or RANTES may be useful in assessing ventricular volume. The amount or concentration in the sample of these markers is indicative of the ventricular volume of the subject;
Individual markers Clusterin and/or NSE may be useful in assessing mean hippocampal volume (LHV). The amount or concentration in sample of these markers is indicative of the left hippocampal volume (LHV) of the subject;
Individual marker Clusterin may be useful in assessing right entorhinal cortex volume (REC). The amount or concentration in the sample of this marker is indicative of the right entorhinal cortex volume (REC) in the subject.
Individual marker transthyretin may be useful in assessing left entorhinal cortical volume (LEC). The amount or concentration in sample of these markers is indicative of the left entorhinal cortical volume (LEC) of the subject.
Individual markers Clusterin and/or transthyretin may be useful in assessing entorhinal cortical thicknesses (ECT). The amount or concentration in sample of these markers is indicative of the entorhinal cortical thicknesses (ECT) in both right and left hemispheres of the subject. Individual marker Clusterin and/or NSE and/or RANTES may be useful in assessing whole brain volume. The amount or concentration in sample of said atrophy biomarkers being indicative of whole brain volume in both right and left hemispheres of the subject.

For example (see Table 4 below) in a subject having AD:
Individual markers A1AT and/or NSE may be useful in assessing ventricular volume. The amount or concentration in the sample of these markers is indicative of the ventricular volume of the subject;
Individual markers BDNF and/or ApoC3 and/or ApoA1 and/or ApoE may be useful in assessing mean hippocampal volume. The amount or concentration in sample of these markers is indicative of the mean hippocampal volume of the subject;
Individual marker ApoC3 and/or ApoE may be useful in assessing mean entorhinal volume. The amount or concentration in sample of these markers is indicative of the mean entorhinal volume of the subject.
Individual markers ApoC3 and/or ApoA1 and/or ApoE and/or transthyretin may be useful in assessing mean entorhinal cortical thicknesses (ECT). The amount or concentration in sample of these markers is indicative of the entorhinal cortical thicknesses (ECT) of the subject.

Individual marker ApoE and/or ApoA1 and/or Aβ40 may be useful in assessing whole brain volume. The amount or concentration in sample of said atrophy biomarkers being indicative of whole brain volume in both right and left hemispheres of the subject.

The biomarker panels described herein comprise markers which expression is modulated, i.e. quantitatively increased or decreased, in normal versus disease states. The degree to which expression differs in normal versus disease states need only be large enough to be visualised via standard characterisation techniques. Methods for the detection and quantification of the differentially expressed markers of a biomarker panel are well known in the art and any suitable method may be employed.

In one embodiment, the marker of a biomarker panel may be detected using a binding agent, such as an antibody, specific to that marker, for example in an ELISA assay or Western blotting.

Methods relating to the production of antibodies capable of specifically recognising one or more epitopes of the individual markers in the biomarker panels described herein are known in the art. Such antibodies may include, but are not limited to, polyclonal antibodies, monoclonal antibodies (mAbs), humanised or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Such antibodies may be utilised as part of AD treatment methods, and/or may be used as part of diagnostic techniques whereby patients may be tested for the amount, concentration or expression of the individual markers in the biomarker panels.

For the production of antibodies, various host animals may be immunised by injection with a differentially expressed or pathway protein, or a portion thereof. Such host animals may include, but are not limited to, rabbits, mice and rats, to name but a few. Various adjuvants may be used to increase the immunological response, depending on the host species, including active substances such as lysolecithin, Pluronic polyols, polyanions, peptides, oil emulsions, keyhole limpet hemocyamin, dinitrophenol, and potentially useful human adjuvant such as BCG bacille Calmette-Fuerin) and *Corynebacterium parvum*.

Polyclonal antibodies are heterogeneous populations of antibody molecules derived from the sera of animals immunised with an antigen, such as target proteins, or an antigenic functional derivative thereof. For the production of polyclonal antibodies, host animals such as those described above, may be immunised by injection with differentially expressed or pathway protein supplemented with adjuvants as also described above.

Monoclonal antibodies, which are homogeneous populations of antibodies to a particular antigen, may be obtained by any technique, which provides for the production of antibody molecules by continuous cell lines in culture. These include, but are not limited to, the hybridoma technique of Kohler and Milstein (1975, Nature 256; 495-497; and U.S. Pat. No. 4,376,110), the human β-cell hybridoma technique (Kosbor, et al., 1983, Immunology Today 4: 72; Cole, et al., 1983, Proc. Natl. Acad. Sci. USA 80; 2026-2030), and the EBV-hybridoma technique (Cole, et al., 1985, Monoclonal Antibodies and Cancer Therapy, Alan R. Liss Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of 'chimeric antibodies' (Morrison, et al., 1984, Proc. Natl. Acad. Sci. 81: 6851-6855; Neuberger, et al., 1984, Nature 312: 604-608; Takeda, et al., 1985, Nature 314: 452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242: 423-426; Huston, et al., 1988, Proc. Natl. Acad. Sci. USA 85: 5879-5883; and Ward, et al., 1989, Nature 334: 544-546) can be adapted to produce differentially expressed or pathway protein-single chain antibodies. Single chain antibodies are formed by linking the heavy and light chain fragments of the Fv region via an amino acid bridge, resulting in a single chain polypeptide.

Antibody fragments, which recognise specific epitopes, may be generated by known techniques. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternative, Fab expression libraries may be constructed (Huse, et al., 1989, Science 246: 1275-1281) to allow rapid and easy identification of monoclonal Fab fragments with the desired specificity.

In some embodiments of the methods described herein, the sample may be immobilised on a solid support for analysis. An antibody sandwich technique may be employed in which binding agents, such as antibodies, specific for the individual markers in the biomarkers panel are immobilized on a solid support such as a planar surface or a microparticle bead and markers in the panel are captured by the immobilised binding agents, such as immobilized antibodies. The captured markers are then detected using a second binding agent, such as a secondary antibody, that may be directly labeled with a signal generating agent (enzyme, fluorescent tag, radiolabel etc.) or may be detected using further amplification (labeled secondary antibody, streptavidin/biotin systems with enzyme, fluorophore, radiolabel etc.). Other methods may include, but are not limited to, one-dimensional or two-dimensional (2D) gel electrophoresis of samples. Such methods are followed by transfer to a solid surface using techniques such as Western blotting and subsequent detection using antibodies specific for the AD biomarkers.

In other embodiments, autoantibodies to the biomarkers may be detected using the Western blotting approach described above using samples from a healthy subject, a patient or representative of AD, and then detecting the presence of auto-antibodies specific for the marker that are present in the sample, but not in healthy subjects.

An example of a non-antibody binding agent is an aptamer. Examples of aptamers include nucleic acid aptamers and peptide aptamers.

Alternatively, the markers may be detected by, amongst others, silver staining of 2D gel electrophoresis or mass spectrometry techniques including LS/MS/MS, MALDI-TOF, SELDI-TOF and TMT-SRM.

Other such standard characterisation techniques by which expression differences may be visualised are well known to those skilled in the art. These include successive chromatographic separations of fractions and comparisons of the peaks, capillary electrophoresis, separations using micro-channel networks, including on a micro-chip, SELDI analysis and qPST analysis.

Chromatographic separations can be carried out by high performance liquid chromatography as described in literature, the chromatogram being obtained in the form of a plot of absorbance of light at 280 nm against time of separation. The material giving incompletely resolved peaks is then re-chromatographed and so on.

Capillary electrophoresis is a technique described in many publications, for example in the literature "Total CE Solutions" supplied by Beckman with their P/ACE 5000 system. The technique depends on applying an electric potential across the sample contained in a small capillary tube. The tube has a charged surface, such as negatively charged silicate glass. Oppositely charged ions (in this instance, positive ions) are attracted to the surface and then migrate to the appropriate electrode of the same polarity as the surface (in this instance, the cathode). In this electro-osmotic flow (EOF) of the sample, the positive ions move fastest, followed by uncharged material and negatively charged ions. Thus, proteins are separated essentially according to charge on them.

Micro-channel networks function similarly to capillaries and can be formed by photoablation of a polymeric material. In this technique, a UV laser is used to generate high energy light pulses that are fired in bursts onto polymers having suitable UV absorption characteristics, for example polyethylene terephthalate or polycarbonate. The incident photons break chemical bonds with a confined space, leading to a rise in internal pressure, mini-explosions and ejection of the ablated material, leaving behind voids which form micro-channels. The micro-channel material achieves a separation based on EOF, as for capillary electrophoresis. It is adaptable to micro-chip form, each chip having its own sample injector, separation column and electrochemical detector: see J. S. Rossier et al., 1999, Electrophoresis 20: pages 727-731.

Surface enhanced laser desorption ionisation time of flight mass spectrometry (SELDI-TOF-MS) combined with ProteinChip technology can also provide a rapid and sensitive means of profiling markers and is used as an alternative to 2D gel electrophoresis in a complementary fashion. The ProteinChip system consists of aluminium chips to which protein samples can be selectively bound on the surface chemistry of the chip (eg. anionic, cationic, hydrophobic, hydrophilic etc). Bound markers are then co-crystallised with a molar excess of small energy-absorbing molecules. The chip is then analysed by short intense pulses of N2 320 nm UV laser with protein separation and detection being by time of flight mass spectrometry. Spectral profiles of each group within an experiment are compared and any peaks of interest can be further analysed using techniques as described below to establish the identity of the markers.

Isotopic or isobaric Tandem Mass Tags® (TMT® Thermo Scientific, Rockford, USA) technology may also be used to detect markers such as proteins of a biomarker panel described herein. Briefly, the proteins in the samples for comparison are optionally digested, labeled with a stable isotope tag and quantified by mass spectrometry. In this way, expression of equivalent proteins in the different samples can be compared directly by comparing the intensities of their respective isotopic peaks or of reporter ions released from the TMT® reagents during fragmentation in a tandem mass spectrometry experiment.

Detection of markers of biomarker panels described herein may be preceded by a depletion step to remove the most abundant proteins from the sample. The large majority of the protein composition of serum/plasma consists of just a few proteins. For example, albumin, which is present at a concentration of 35-50 mg/ml, represents approximately 54% of the total protein content with IgG adding other 16%. In contrast, proteins changing in response to disease, for example as a result of tissue leakage, may circulate at 10 ng/ml. This vast dynamic range of protein concentrations represents a major analytical challenge and to overcome the problem, a multiple affinity depletion column may be used to remove the most highly abundant proteins (e.g. the 5, 6, 7, 8, 9 or 10 most highly abundant proteins). This enables the detection of changes in lower abundance ranges because more starting material can be used and there is less interference from the highly abundant molecules. Such a depletion strategy can be applied before any detection method.

The method may further comprise determining an effective therapy for treating neurocognitive disorder. For example, the amount or concentration of the markers in the biomarker panels may be indicative of the subject being responsive or non-responsive to a particular therapy or treatment.

In one embodiment of the invention, the biomarker panel may be useful in a method whereby the amounts or concentrations of the individual markers in the biomarker panel in a tissue sample or body fluid sample of a subject with a neurocognitive disorder are used to predict the most appropriate and effective therapy to alleviate the neurocognitive disorder.

In another embodiment, such method may be further include the use of an agent to treat the neurocognitive disorder wherein the agent will reduce, delay or arrest the disease-associated change in marker levels of the biomarker panel in the neurocognitive disorder towards that found in the normal state in order to prevent the development or progression of the neurocognitive disorder. Preferably, the expression of the marker is restored to that of the normal state. Monitoring the expression of the markers of the biomarker panels described herein may be indicative of the progress and/or efficacy of the treatment.

The biomarker panel may also be used in method of screening an agent to determine its usefulness in treating a neurocognitive disorder, such as AD, the method comprising:
  (a) providing a tissue sample or body fluid sample obtained from, or representative of, a subject having a neurocognitive disorder or symptoms thereof, wherein the subject and/or the sample has been treated with the agent being screened,
  (b) determining the amount or concentration in the sample from, or representative of, the treated subject and/or sample of markers of a biomarker panel as defined herein; and
  (c) determining whether the agent affects the amount or concentration of the markers of the biomarker panel in the treated subject and/or sample.

Preferably, the biomarker panel consists essentially of markers transthyretin (TTR), Clusterin, Cystatin C (CST3), Alpha-1-Acid glycoprotein (A1AcidG), Intercellular adhesion molecule 1 (ICAM1), Complement C4 (CC4), pigment epithelium derived factor (PEDF) and Alpha1 antitrypsin (A1AT), optionally further comprising one or more markers selected from the group of normal T cell expressed and secreted (RANTES), Apolipoprotein C-III (ApoC3), activator inhibitor type 1 (PAI-1), C-reactive protein (CRP), Cathepsin D (CTSD), apolipoprotein E (ApoE), alpha-2-macroglobulin (A2M), serum amyloid P component (SAP), advanced glycosylation end product-specific receptor (sRAGE), Neuron specific enolase (NSE), complement factor H (CFH), amyloid beta (A4) precursor protein (AB40 or Aβ40), Ceruloplasmin, neural cell adhesion molecule (NCAM), ApoA1, Abeta 42, BDNF, Beta-2-microglobulin (B2M), and VCAM-1.

More preferably, the panel further comprises ApoE ε4 allele presence (ApoE genotype).

The biomarker panels described herein may be used to test agents for the ability to prevent or ameliorate neurocognitive disorders, such as AD, or one or more symptoms thereof.

Such agents may be tested in human subjects in clinical trials. Any agent which restores the expression of the proteins in a biomarker panel described herein towards levels found in healthy individuals may be of potential use in treating a neurocognitive disorder, such as AD, i.e. reducing AD symptoms or slowing the progression of AD During clinical trials, for example, the amount or concentration of a marker of a biomarker panel as described herein can be determined in the presence or absence of the agent being tested. The efficacy of the agent can be followed by comparing the expression data obtained to the corresponding known expression patterns in a normal state. Agents exhibiting efficacy are those which alter the amount or concentration of the markers in the biomarker panel to more closely resemble that of the normal state, or which stabilise expression of the biomarker panel i.e. prevent progression of the disease.

The detection of the markers in the biomarker panel in the neurocognitive disorder relative to their expression in a normal state can also be used for monitoring the efficacy of potential agents for the treatment of a neurocognitive disorder, such as AD, during clinical trials. During clinical trials, for example, the level and/or activity of the markers in the biomarker panel can be determined in relevant cells and/or tissues and/or body fluids in the presence or absence of the agent being tested. The efficacy of the agent can be followed by comparing the markers levels and/or activities data obtained to the corresponding known levels/activities for the cells and/or tissues and/or body fluids in a normal state. Agents exhibiting efficacy are those which alter the amount or concentration of the biomarker panel of the cell and/or tissue sample and/or body fluid from a subject to more closely resemble that of the normal state or which stabilise the pattern i.e. prevent progression of the disease.

With regard to intervention, any treatments that restore or partially restore the expression of markers in a biomarker panel described herein to healthy levels should be considered as candidates for therapeutic intervention in neurocognitive disorders such as AD. Dosages of test agents may be determined by deriving dose-response curves.

Similarly, any treatments that can prevent the development of neurocognitive disorders such as AD or prevent progression to levels of more advanced AD should be considered as candidates for the AD therapeutic intervention.

In addition, animal models of neurocognitive disorders such as AD, and those described herein, may be used to identify agents capable of treating AD symptoms. Such animal models may be used in the identification of drugs, pharmaceuticals, therapies and interventions which may be effective in treating such disorders. The response of the animals to the exposure may be monitored by assessing the expression of the markers and comparing it to that of wild-type mice.

The amount or concentration of the markers of the biomarker panel described herein may be utilised in conjunction with animal model systems to assess the ability of an agent to ameliorate symptoms of neurocognitive disorder, or prevent the progression of neurocognitive disorder. For example, the amount or concentration of the markers of the biomarker panel described herein may form part of a fingerprint profile, which may then be used in such an assessment. Fingerprint profiles may be characterised for disease states within the animal model systems. Subsequently, these known fingerprint profiles may be compared to ascertain the effect a test agent has to modify such fingerprint profiles, and to cause the profile to more closely resemble that of a more desirable fingerprint. For example, administration of an agent may cause the fingerprint profile of an AD model system to more closely resemble the control system, or may prevent further changes in fingerprint profile. Administration of an agent may, alternatively, cause the fingerprint profile of a control system to begin to mimic an AD state, which may, for example, be used in further characterising the agent of interest, or may be used in the generation of additional animal models.

The amount or concentration of the markers of the biomarker panels described herein, in a subject treated with the agent compared to a subject not treated with the agent, is indicative that the agent may be useful in treating a neurocognitive disorder.

The divergence of the concentration or amount of the markers in the biomarker panel over time in subjects having symptoms of a neurocognitive disorder and normal subjects may be determined.

The screening method described herein may further comprise prior to step (a), the step of determining the concentration or amount of the markers of the biomarker panels in one or more control samples from healthy individuals, patients having a neurocognitive disorder of differing severity or progression, or symptoms thereof, and patients having a neurocognitive disorder or symptoms thereof not treated with agent.

The step of selecting or rejecting the agent according to the extent to which it changes the concentration or amount of the markers of the biomarker panel in the treated subject having symptoms of a neurocognitive disorder relative to controls. Suitable controls include similarly aged people without the neurocognitive disorder.

An agent may be selected if it prevents or slows the change over time in the concentration or amount of the markers of the biomarker panels relative to controls.

Preferably, the agent is selected if it converts the amount or concentration of a marker of the biomarker panels towards that of a normal subject. More preferably, the agent is selected if it converts amount or concentration of a marker of the biomarker panels to that of the normal subject.

Samples taken over time may be taken at intervals of weeks, months or years. For example, samples may be taken at monthly, two-monthly, three-monthly, four-monthly, six-monthly, eight-monthly or twelve-monthly intervals.

A change in concentration or amount over time may be an increase or decrease in concentration or amount, compared to the initial level of concentration or amount in samples from the subject and/or compared to the level of concentration or amount in samples from normal subjects. The agent may be selected if it slows or stops the change of concentration or amount over time.

In the screening methods described above, subjects comprise:
(a) normal subjects and subjects having symptoms of a neurocognitive disorder, such as AD; and/or,
(b) subjects having symptoms of a neurocognitive disorder which have not been treated with the agent and subjects having a neurocognitive disorder which have been treated with the agent.

In another embodiment, subjects may include:
(a) normal subjects who have and have not been treated with the agent; and one or both of
(b) subjects having mild cognitive impairment (MCI) who have and have not been treated with the agent; and
(c) subjects having symptoms of a neurocognitive disorder, such as AD, who have and have not been treated with the agent.

The subjects having symptoms of a neurocognitive disorder, such as AD, may be human subjects with a neurocognitive disorder.

As described above, the neurocognitive disorders may include Mild Cognitive Impairment (MCI), a recognised precursor to AD, and dementias, such as AD and other late onset dementias including vascular dementia, dementia with lewy bodies and frontotemporal dementia, alone and as a mixed dementia with Alzheimer's disease.

Alzheimer's disease may be AD at any stage or severity, including pre-Alzheimer's stages, such as mild cognitive impairment (MCI) as well as advanced AD.

In one embodiment, the subjects having symptoms of a neurocognitive disorder, such as AD, may be non-human animal models of the neurocognitive disorder. Suitable non-human animal models of AD are well known in the art and include mutant amyloid precursor protein (APP) transgenic mice, presenilin-1 (PS-1) transgenic mice, double transgenic APP/PS-1 transgenic mice and mice overexpressing glycogen synthase kinase (GSK) (see Lucas et al (2001) EMBO J. 20, p 27-39). In this embodiment, the normal subjects are wild-type mice.

The tissue or body fluid samples which may be used in the screening methods described herein are, for example, brain tissue, blood, plasma, serum, saliva or cerebro-spinal fluid samples.

Within the present invention are also encompassed methods of making a pharmaceutical composition which comprises having identified an agent using the screening method described herein, the further step of manufacturing, isolating or obtaining the agent and formulating it with an acceptable carrier to provide the pharmaceutical composition.

It is possible that AD symptoms may be brought about, at least in part, by an abnormal level of target protein, or by the presence of a target protein exhibiting an abnormal activity. As such, the reduction in the level and/or activity of such target protein would bring about the amelioration AD symptoms. Techniques for the reduction of target protein gene expression levels or target protein activity levels are discussed herein.

Alternatively, it is possible that symptoms of neurocognitive disorders such as AD, may be brought about, at least in part, by the absence or reduction of the level of target protein expression, or a reduction in the level of a target protein's activity. As such, an increase in the level of target protein gene expression and/or the activity of such proteins would bring about the amelioration of AD symptoms.

The effects of an increase or reduction in target protein gene expression levels or target protein activity levels may be determined or monitored using a panel of biomarkers as described herein.

A variety of techniques may be utilised to inhibit the expression, synthesis, or activity of such target genes and/or proteins.

For example, agents which exhibit inhibitory activity, may be used in accordance with the invention to prevent mild cognitive impairment or AD symptoms. Such molecules may include, but are not limited to, peptides (such as, for example, peptides representing soluble extracellular portions of target protein transmembrane receptors), phosphopeptides, small organic or inorganic molecules, or antibodies (including, for example, polyclonal, monoclonal, humanised, anti-idiotypic, chimeric or single chain antibodies, and Fab, $F(ab')_2$ and Fab expression library fragments, and epitope-binding fragments thereof).

Antibodies that are both specific for target protein and interfere with its activity may be used to inhibit target protein function. Where desirable, antibodies specific for mutant target protein, which interferes with the activity of such mutant target product, may also be used.

In instances where the target gene protein is intracellular and whole antibodies are used, internalising antibodies may be preferred. However, lipofectin or liposomes may be used to deliver the antibody or a fragment of the Fab region, which binds to the target protein epitope into cells. Where fragments of the antibody are used, the smallest inhibitory fragment, which binds to the target protein's binding domain, is preferred. For example, peptides having an amino acid sequence corresponding to the domain of the variable region of the antibody that binds to the target protein may be used. Such peptides may be synthesised chemically or produced via recombinant DNA technology using methods well known in the art (e.g. see Creighton, 1983, supra; and Sambrook et al, 1989, supra).

Alternatively, single chain neutralising antibodies, which bind to intracellular target protein epitopes, may also be administered. Such single chain antibodies may be administered, for example, by expressing nucleotide sequences encoding single-chain antibodies within the target cell populating by utilising, for example, techniques such as those described in Marasco et al (Marasco, W. et al, 1993, Proc. Natl. Acad. Sci. USA, 90: 7889-7893).

In instances where the target protein is extracellular, or is a transmembrane protein, any of the administration techniques described herein, which are appropriate for peptide administration may be utilised to effectively administer inhibitory target protein antibodies to their site of action.

Furthermore, antisense, siRNA and ribozyme molecules, which inhibit expression of the target protein gene, may also be used in accordance with the invention to inhibit the aberrant target protein gene activity; triple helix molecules may be utilised in inhibiting the aberrant target protein gene activity. Antisense, ribozyme and triple helix molecules may be designed to reduce or inhibit either wild type, or if appropriate, mutant target protein gene activity. Techniques for the production and use of such molecules are well known to those of skill in the art.

Antisense RNA and DNA molecules act to directly block the translation of mRNA by hybridising to targeted mRNA and preventing protein translation. With respect to antisense DNA, oligodeoxy-ribonucleotides derived from the translation initiation site, e.g. between the −10 and +10 regions of the target gene nucleotide sequence of interest, are preferred.

Ribozymes are enzymatic RNA molecules capable of catalysing the specific cleavage of RNA. (For a review, see Rossi, J., 1994, Current Biology 4: 469-471). The mechanism of ribozyme action involves sequence specific hybridisation of the ribozyme molecule to complementary target RNA, followed by an endonucleolytic cleavage. The composition of ribozyme molecules must include one or more sequences complementary to the target protein mRNA, and must include the well-known catalytic sequence responsible for mRNA cleavage. For this sequence, see U.S. Pat. No. 5,093,246. As such, within the scope of the invention are engineered hammerhead motif ribozyme molecules that specifically and efficiently catalyse endonucleolytic cleavage of RNA sequences encoding target proteins.

Specific ribozyme cleavage sites within any potential RNA target are initially identified by scanning the molecule of interest for ribozyme cleavage sites which include the following sequences, GUA, GUU and GUC. Once identified, short TNA sequences of between 15 and 20 ribonucleotides corresponding to the region of the target protein gene, containing the cleavage site may be evaluated for predicted structural features, such as secondary structure, that may render the oligonucleotide sequence unsuitable. The suitability of candidate sequences may also be evaluated by testing their accessibility to hybridise with complementary oligonucleotides, using ribonuclease protection assays.

RNA interference (RNAi) is a process of sequence-specific, post-transcriptional gene silencing in animals and plants, initiated by double-stranded RNA (dsRNA) that is homologous in sequence to the silenced gene. RNAi is mediated by short double-stranded RNA molecules (small interfering RNAs or siRNAs). siRNAs may be introduced into a cell as short RNA oligonucleotides of 10-15 bp, or as longer dsRNAs which are subsequently cleaved to produce siRNAs. The RNA may be introduced into the cell as RNA, or may be transcribed from a DNA or RNA vector.

siRNA molecules may be synthesized using standard solid or solution phase synthesis techniques which are known in the art. Alternatively, siRNA molecules or longer dsRNA molecules may be made recombinantly by transcription of a nucleic acid sequence, preferably contained within a vector as described below.

Another alternative is the expression of a short hairpin RNA molecule (shRNA) in the cell. shRNAs are more stable than synthetic siRNAs. A shRNA consists of short inverted repeats separated by a small loop sequence. One inverted repeat is complimentary to the gene target. The shRNA is then processed into a siRNA which degrades the target gene mRNA and suppresses expression. shRNAs can produced within a cell by transfecting the cell with a DNA construct encoding the shRNA sequence under control of a RNA polymerase III promoter, such as the human H1 or 7SK promoter. Alternatively, the shRNA may be synthesised exogenously and introduced directly into the cell. Preferably, the shRNA sequence is between 40 and 100 bases in length, more preferably between 40 and 70 bases in length. The stem of the hairpin is preferably between 19 and 30 base pairs in length. The stem may contain G-U pairings to stabilise the hairpin structure.

Nucleic acid molecules to be used in triplex helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC$^+$ triplets across the three associated strands of the resulting triple helix. The pyrimidine-rich molecules provide base complementary to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so-called "switchback" nucleic acid molecule. Switchback molecules are synthesised in an alternating 5'-3', 3'-5' manner, such that they base pair with first one strand of a duplex and then the other, eliminating the necessity for a sizeable stretch of either purines or pyrimidines to be present on one strand of a duplex.

Anti-sense RNA and DNA, siRNAs, ribozyme and triple helix molecules of the invention may be prepared by any method known in the art for the synthesis of DNA and RNA molecules. They include techniques for chemically synthesising oligodeoxyribonucleotides and oligo-ribonucleotides well known in the art such as, for example, solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors, which incorporate suitable RNA polymerase promoters such as the T7 or SP6 polymerase promoters. Alternatively, antisense cDNA constructs that synthesise antisense RNA constitutively inducible, depending on the promoter used, can be introduced stably into cell lines.

Target proteins that cause neurocognitive disorders such as AD, may be underexpressed in disorder situations. Alternatively, the activity of target protein may be diminished, leading to the development of symptoms. Described herein are methods whereby the level of target protein may be increased to levels wherein AD symptoms are prevented or ameliorated. The level of target protein activity may be increased, for example, by either increasing the level of target protein present or by increasing the level of active target protein which is present.

For example, a target protein, at a level sufficient to ameliorate AD symptoms may be administered to a patient exhibiting such symptoms. One of skill in the art will readily know how to determine the concentration of effective, non-toxic doses of the normal target protein, utilising techniques such as those described herein.

Further, patients may be treated by gene replacement therapy. One or more copies of a normal target protein gene or a portion of the gene that directs the production of a normal target protein with target protein gene function, may be inserted into cells, using vectors which include, but are not limited to, adenovirus, adeno-associated virus, and retrovirus vectors, in addition to other particles that introduce DNA into cells, such as liposomes. Additionally, techniques such as those described above may be utilised for the introduction of normal target protein gene sequences into human cells.

Cells, preferably autologous cells, containing normal target protein gene sequences may then be introduced or reintroduced into the patient at positions which allow for the prevention or amelioration of AD symptoms. Such cell replacement techniques may be preferred, for example, when the target protein is a secreted, extracellular protein.

The effects of administering an antibody or nucleic acid suppressor may be determined or monitored using a panel of biomarkers as described herein.

Pharmaceutical Preparations and Methods of Administration

Agents that affect target protein expression, synthesis and/or activity can be administered to a patient at therapeutically effective doses to prevent or to treat or to ameliorate neurocognitive disorders such as AD. A therapeutically effective dose refers to that amount of the compound sufficient to result in amelioration of symptoms, or alternatively, to that amount of a nucleic acid molecule sufficient to express a concentration of protein which results in the amelioration of such symptoms.

The effects of an agent, whether it is a nucleic acid molecule, an antibody, a small molecule compound or a cell may be determined or monitored using a panel of biomarkers as described herein.

Toxicity and therapeutic efficacy of such agents can be determined by standard pharmaceutical procedures in cell cultures or experimental animals, e.g. for determining by $ED_{50}$ (the dose therapeutically effective in 50% of the population) and by determining the $ED_{50}$ of any side-effects (toxicity—TD50). The dose ratio between toxic and therapeutic effects is the therapeutic index and it can be expressed as the ratio $TD_{50}/ED_{50}$. Agents, which exhibit large therapeutic indices, are preferred, whilst for those that exhibit toxic side effects, care should be taken to design a delivery system that targets such agents to the site of affected tissue in order to minimise potential damage to uninfected cells and, thereby, reduce side effects.

The data obtained from the animal studies can be used in formulating a range of dosage for use in humans. The dosage of such agents lies preferably within a range of circulating concentrations that include the $ED_{50}$ with little or no toxicity. The dosage may vary within this range depending upon the dosage form employed and the route of administration utilised.

Pharmaceutical compositions for use in accordance with the present invention may be formulated in conventional manner using one or more physiologically acceptable carriers or excipients.

Thus, the agents may be formulated for administration by inhalation or insufflation (either through the mouth or the nose) or oral, buccal, parenteral and rectal administration.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methyl-cellulose); fillers (e.g. lactose, microcrystalline cellulose or calcium hydrogen phosphate); lubricants (e.g. magnesium, stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); and preservatives (e.g. methyl or propyl-p-hydroxybenzoates or sorbic acid). The preparations may also contain buffer salts, flavours, colours and sweeteners as appropriate.

Preparations for oral administration may be suitably formulated to give controlled release of the active agent. For buccal administration the compositions may take the form of tablets or lozenges formulated in conventional manner.

For administration by inhalation, the agents for use according to the present invention are conveniently delivered in the form of an aerosol spray presentation from pressurised packs or a nebuliser, with the use of a suitable propellant, e.g. dichlorodifluoromethane, trichlorofluoromethane, dichloro-tetrafluoroethane, carbon dioxide or other suitable gas. In the case of a pressurised aerosol the dosage unit may be determined by providing a valve to deliver a metered amount. Capsules and cartridges of, e.g. gelatin, for use in an inhaler or insufflator may be formulated containing a powder mix of the compound and a suitable powder base such as lactose or starch.

The agents may be formulated for parenteral administration by injection, e.g. by bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stablising and/or dispersing agents. Alternatively, the active ingredient may be in powder form for constitution with a suitable vehicle, e.g. sterile pyrogen-free water, before use.

The agents may also be formulated in rectal compositions such as suppositories or retention enemas, e.g. containing conventional suppository bases such as cocoa butter or other glycerides.

In addition to the formulations described previously, the agents may also be formulated as a depot preparation. Such long acting formulations may be administered by implantation, for example, subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

The compositions may, if desired, be presented in a pack or dispenser device, which may contain one or more unit dosage forms containing the active ingredient. The pack may, for example, comprise metal or plastic foil, such as blister pack. The pack or dispenser device may be accompanied by instructions for administration.

Kits for the Detection of the Biomarkers Panel

The present invention also provides for a kit comprising reagents for the detection of markers of a biomarker panel as described herein in a tissue sample or body fluid sample. The biomarker panel consists essentially of markers transthyretin (TTR), Clusterin, Cystatin C (CST3), Alpha-1-Acid glycoprotein (A1AcidG), Intercellular adhesion molecule 1 (ICAM1), Complement C4 (CC4), pigment epithelium derived factor (PEDF) and Alpha1 antitrypsin (A1AT) and optionally one or more markers selected from the group of regulated on activation, normal T cell expressed and secreted (RANTES), Apolipoprotein C-III (ApoC3), plasminogen activator inhibitor type 1 (PAI-1), C-reactive protein (CRP), Cathepsin D (CTSD), apolipoprotein E (ApoE), alpha-2-macroglobulin (A2M), serum amyloid P component (SAP), advanced glycosylation end product-specific receptor (sRAGE), Neuron specific enolase (NSE), complement factor H (CFH), amyloid beta (A4) precursor protein (AB40 or Aβ40), Ceruloplasmin, neural cell adhesion molecule (NCAM), ApoA1, Abeta 42, BDNF, Beta-2-microglobulin (B2M) and VCAM-1.

Preferably, the panel further comprises ApoE ε4 allele presence (ApoE genotype).

In one embodiment, the kit further comprises one or more binding agents which specifically bind to the markers of the biomarker panels.

In one particular embodiment, the one or more binding agents are primary antibodies, each antibody binding specifically to a different individual marker in the biomarker panel. Preferably, the kit may further comprise one or more secondary antibodies which specifically bind to the primary antibodies. The secondary antibodies may optionally be labeled, for example fluorescent labeled or tagged.

The binding agent may be an aptamer, an oligonucleotide or a chemical compound.

Alternatively, a kit may comprise one or more peptides representing the selected markers and a suitable grade of a proteolytic enzyme for use in a mass spectrometry method. The peptides may be synthetic peptides and may comprise one or more heavy isotopes of carbon, nitrogen, oxygen and/or hydrogen. The binding agents, e.g. the antibodies, may be immobilised on an assay plate, beads, microspheres or particles. Optionally, beads, microspheres or particles may be dyed, tagged or labeled.

The kit may further comprise a control sample of the markers of the biomarker panel.

A kit may further comprise one or more detection reagents for detecting the presence of the tagged secondary antibodies.

The reagents in the kit may be sealed in a suitable container which protects its contents from the external environment. Such a kit may include instructions for use.

The methods described herein may be performed, for example, by utilising pre-packaged diagnostic kits comprising a biomarker panel as described herein and/or reagents which specifically bind to the individual markers of the biomarker panel, such as binding agents, e.g. antibodies, which may be conveniently used, e.g. in clinical settings, to diagnose patients exhibiting AD symptoms.

All documents, publications and sequence database entries mentioned in this specification are incorporated herein by reference in their entirety for all purposes.

Certain aspects and embodiments of the invention will now be illustrated by way of example and with reference to the figures and tables described above.

EXAMPLES

Alzheimer's disease (AD) is exemplified herein as a representative example of all related dementias and neurocognitive disorders.

Detecting AD at the earliest possible stage is vital to enable trials of disease modification agents and considerable efforts are being invested in the identification and replication of biomarkers for this purpose.

Such biomarkers currently include measures of tau and amyloid beta (Aβ) in cerebrospinal fluid (CSF), measures of atrophy using magnetic resonance imaging (MRI) and measures of Aβ pathological load using positron emission tomography (PET). All these approaches are promising although molecular imaging is currently a costly procedure available in relatively few centres and lumbar puncture is moderately invasive. Furthermore repeated measures are problematical in both cases.

Blood (plasma) on the other hand is a more accessible bio-fluid suitable for repeated sampling. Using a case-control study design with a gel based approach (2-DGE & LC-MS/MS) two proteins (complement factor H (CFH) and alpha-2-macroglobulin) were observed as potential markers of AD[1], both of which were subsequently replicated by independent groups[2-3]. In the present study changes in three other proteins, namely serum amyloid P (SAP), complement C4 (CC4), and ceruloplasmin were observed, all of which have been implicated in AD pathogenesis[4-6]. However, case-control studies are problematical when there is a long prodromal disease phase as there is in AD. In such instances a large proportion of apparently normal controls already harbour the disease processes and hence may already have a peripheral biomarker disease signature. In order to overcome the limitations of case-control design, proteins associated with surrogates of disease severity (hippocampal atrophy and clinical progression) were sought and Clusterin was identified as a marker associated with both these surrogate measures'. Building on this 'endophenotype' discovery approach transthyretin (TTR) and Apolipoprotein A1 (ApoA1) were found to be associated with faster declining AD subjects and increased plasma Apolipoprotein E (ApoE) levels related to increased Aβ burden in the brain[8-9].

These observations led to a set of that might act as biomarkers relevant to AD. However such findings require replication, in large studies, ideally using samples drawn from more than one cohort source and using a platform that enables multiplexing.

Hence, firstly multiplex panels of biomarkers implicated in the disease needed to be identified; secondly validation of a set of blood-based biomarkers in a large multicentre cohort with specified a priori outcome variables of the disease endophenotype measure of atrophy on MRI and of clinical severity needed to be established and thirdly determination of the accuracy of a multiplexed panel of disease relevant biomarkers in predicting conversion of mild cognitive impairment to dementia in a defined time period needed to be found.

Furthermore, as disease case compared to normal control designs are limited because of occult disease in controls, such replication studies should have as outcomes, endophenotypes of disease or clinically meaningful outcomes such as prediction of disease progression.

Methods

Subjects and Clinical Classification

Plasma samples from AD, MCI and elderly non-demented controls were selected from three independent studies. Add-NeuroMed (ANM), a multi-center European study[10]; Kings Health Partners-Dementia Case Register (KHP-DCR), a UK clinic and population based study and Genetics AD Association (GenADA) a multisite case-control longitudinal study based in Canada. The diagnosis of probable AD was made according to Diagnostic and Statistical Manual for Mental Diagnosis (DSM-IV) and National Institute of Neurological, Communicative Disorders and Stroke-Alzheimer's disease and Related Disorders Association (NINCDS-ADRDA) criteria. Mild cognitive impairment (MCI) was defined according to Petersen criteria[11]. Standardized clinical assessment included the Mini-Mental State Examination (MMSE) and Alzheimer's disease Assessment Scale-cognitive subscale (ADAS-cog) (ANM and KHP-DCR studies only) for cognition and for global levels of severity the Clinical Dementia Rating (CDR) (ANM and KHP-DCR studies only). Institutional review boards approved the study procedures and subjects provided written informed consent or proxy consent was obtained.

Plasma samples from 1153 subjects were examined—476 with AD, 225 with MCI and 452 elderly controls with no dementia (Table 2). APOE genotype was determined from venous blood using standard methods[12].

TABLE 2

Subject demographics

| | Control | MCI | | AD | Significance |
| | | $MCI_{nc}$ | $MCI_c$ | | |
|---|---|---|---|---|---|
| N | 452 | 173 | 52 | 476 | |
| Age (yrs) | 75.6 (±6.3, 53-93) | 76.3 (±5.7, 65-90) | 76.2 (±6.9, 56-89) | 77.0 (±6.4, 58-96) | P = 0.012# |
| Sex (%, Female) | 55.6% | 50.1% | 49.1% | 49.4% | P = 0.277 |
| APOE genotype (%, ε4+) | 28% | 35% | 55% | 59% | P < 0.001# |
| MMSE | 29.0 (±1.2, 22-30) | 26.9 (±2.9, 0-30) | 26.3 (±2.1, 18-30) | 20.8 (±5.4, 0-30) | P < 0.001* |
| CDR (Sum of Boxes) | 0.18 (±0.4, 0-3) | 1.82 (±0.9, 0-4.5) | 2.41 (±0.9, 0.5-5) | 4.04 (±3.2, 0-20) | P < 0.001* |

Abbreviations:
AD, Alzheimer's disease;
APOE, Apolipoprotein E;
CDR, Clinical dementia rating;
GDS, Global Deterioration Scale;
$MCI_{nc}$, mild cognitive impairment non-converter;
$MCI_c$, mild cognitive impairment converter;
MMSE, mini mental state examination.
Mean (±S.D, Range), ANOVA was performed and if significant a Tukey's post-hoc comparison was carried out.
*Significance across all 3 groups,
Control compared to AD.

Cognitive Decline

Cognitive decline, as determined by the slope of change in cognition, was calculated for a subset of AD subjects (n=342) who had a minimum of three separate MMSE assessments. Linear mixed effect models were generated using the package 'nlme' in R. Covariates including age at baseline, gender, apolipoprotein E(APOE) ε4 allele presence (ApoE genotype), and years of education were investigated for their effect on the rate of decline. Age at baseline and years of education had a significant effect on the rate (p-value<0.05) and thus were included as fixed effects in the final model. The slope coefficient obtained from the final model for each sample was then used as a rate of cognitive change, defined as the change in MMSE score per year.

Magnetic Resonance Imaging (MRI)

High resolution sagittal 3D T1-weighted MPRAGE volume (voxel size 1.1×1.1×1.2 mm$^3$) and axial proton density/T2-weighted fast spin echo images were acquired on 1.5 T MRI scanners for 476 of the subjects (179 CTL, 123 MCI and 174 AD) as previously reported[13]. The MPRAGE volume was acquired using a custom pulse sequence specifically designed for the ADNI study to ensure compatibility across scanners[14]. Full brain and skull coverage was required for all MR images according to previously published quality control criteria[13, 15]. Image analysis was carried out using the Freesurfer image analysis pipeline (version 5.1.0) to produce regional cortical thickness and subcortical volumetric measures as previously described[16-17]. This segmentation approach has been previously used for analysis in imaging-proteomic studies[18] and AD biomarker discovery[19]. All volumetric measures from each subject were normalized by the subject's intracranial volume while cortical thickness measures were used in their raw form[19]. Measures of hippocampal volume, entorhinal cortex volume and ventricular volume were chosen as key MRI endophenotypes of Alzheimer's disease. For evaluation of hippocampal atrophy the MRI data was stratified into high and low atrophy for the MCI group based on their median volumetric measures.

Immunoassay—Luminex Measurement

Multi-analyte profile (xMAP) technology was used to quantify the candidate proteins (Table 6) and the Luminex 200 (Austin, TX) instrument using 7 Milliplex panels. In more detail:

Milliplex Assays

Seven MILLIPLEX® MAP multiplex panels (96 well plate format; Millipore EMD) were utilised: Human Neurodegenerative Panel 1 (7-plex) Cat. # HNDG1-36K, Panel 2 (6 plex) Cat.# HNDG2-36K, Panel 3-(10-plex) HNDG3-36K, Panel 4 (5-plex) HNDG4-36K, Human Kidney Toxicity Panel 2 (3-plex) Cat. # HKTX2-38K, Human Neurological disorders Mag Panel 1 (12plex) and Panel 2 (4-plex).

Immunoassay Protocol

The Luminex xMAP technology (Austin, TX) uses a solid phase approach to analyze multiple proteins. In brief, the xMAP technology is a flow cytometric-based platform that uses microspheres inserted with a ratio of two different fluorescent dyes. In theory, up to 100 differently coloured beads can be generated with a theoretical multiplex capacity of up to 100 assays per well of a 96-well plate. The capture antibody is covalently coupled to the bead, and immunoassays are run under standard sandwich immunoassay formats.

The plasma samples were first diluted as recommended in the protocol for each Milliplex assay. Each assay well was first rinsed with 100 μL wash buffer (1× L-WB) prior to samples loading. 25 μL of Assay Buffer was added to either 25 μL controls, or samples followed by 25 μL beads to bring the total volume in each well to 75 μL. The assay plates were incubated for 2 hours at room temperature or overnight with agitation on an orbital shaker. The beads in the plate were washed 3 times with 100 μL wash buffer and incubated for 1 hour with 25 μL biotinylated detection antibody. 25 μL fluorescently labeled reporter (streptavidin-PE) molecule was added to the detection antibody for a further 30 minutes. Finally the assay plate was washed 3 times with 100 μL wash buffer and the beads suspended in 100 μL sheath fluid. All plasma samples were assayed in duplicate and a pooled plasma (Mastermix) sample was included as a positive control in addition to high and low QC per plate.

Data Quality Check and Pre-Processing

Fluorescence in each well was measured using Luminex 200 (Austin, TX) instrument and the results were analysed with the Xponent 3.1 (Luminex) software. Median fluorescent intensity (MFI) values were exported and the characteristics of the individual samples were confirmed by calculating the mean, standard deviation (SD) and coefficient of variation (CV %) from the MFI readouts. All processed data points were then imported into Sigma Plot (Systat, ver. 12).

Using a 5-parameter logistic curve fitting method the concentrations of the unknown plasma samples and the master mix were calculated. Any individuals samples that recorded a CV>15% for either duplicate was eliminated; if both duplicates were out of range then both data points were excluded.

Individual analytes were then assessed for quality by applying ranked according to their performance in the assay (31 plates; 1148 plasma samples) and defined using a scoring system based on 4 criteria as follows:

Criteria 1. Standard curve rank: 1=Good quality-within linear section on standard curve and within quality checks (QC) range. 2=Moderate quality, spread across the linear section on standard curve, clustered either higher or lower than QC and 3=poor quality, not on linear section at all, below low QC or higher than top QC.

Criteria 2. Intra-assay CV (%) for QC1 and QC2, CV<30% accepted (point for each QC value).

Criteria 3. Inter-assay CV (%) for our in-house pooled sample (master mix), CV<30% accepted.

Criteria 4. Missing data defined as samples that could not be reliably intrapolated from the standard curve. 1) MFI values outside the quantifiable range, 2) Technical failure resulting in no MFI value being generated.

Data Pre-Processing

Prior to statistical analysis, we examined the performance of each assay using a number of quality checks (QC). Median fluorescent intensity (MFI) was measured using Xponent 3.1 (Luminex Corporation) and exported into Sigma plot (Systat Software; version 12) for estimation of protein concentrations using a 5-parameter logistic fit. Briefly, all analytes that passed QC checks based on the 4 criteria (Standard curve linearity, intra-assay coefficient of variation, inter-assay CV for reference sample and percentage of missing data) were taken forward for further analysis.

Statistical Analysis

Univariate statistical analysis was performed in SPSS 20 (IBM). All raw MFI measures were log transformed to achieve normal distribution. Covariates including age, gender, plasma storage duration (days) and centre were investigated. The inventors found that the majority of proteins were significantly affected by covariates and therefore values were adjusted using a generalized linear regression model (GLM). Partial correlation (adjusting for APOE genotype) analysis was performed to observe any association with either structural MRI brain imaging or cognition assessments. Correlations were performed separately within groups due to the discrete nature of the clinical scores across all groups. The proteins were also analysed individually for their association with disease phenotypes and disease status (AD vs. CTL) via ANCOVA (adjusting for APOE genotype). Multiple linear regressions were used to test for combinations of proteins required for prediction of hippocampal volume.

Classification Analysis

For class prediction and attribute selection, WEKA (University of Waikato) was employed. Naïve Bayes Simple algorithm was used with default settings unless stated otherwise. Datasets were randomly split into 75% train and 25% test. Attribute selection was performed using the Classifier Subset Evaluator with best first search method on the training data. Five iterations of attribute selection were performed and attributes ranked by times observed in each of the iterations. Proteins seen >3 or more times were taken forward as predictor variables (Table 3). Any class imbalance was overcome by applying the Synthetic Minority Oversampling Technique (SMOTE) in WEKA.

TABLE 3

Proteins observed in the feature selection

| Protein | No. Times observed in feature selection | Protein | No. Times observed in feature selection |
| --- | --- | --- | --- |
| Transthyretin | 5 | CathepsinD | 1 |
| Clusterin | 4 | ApoE | 1 |
| Cystatin C | 4 | SAP | 0 |
| A1AcidG | 4 | Ceruloplasmin | 0 |
| ICAM1 | 4 | NCAM | 0 |
| CC4 | 4 | NSE | 0 |
| PEDF | 4 | VCAM1 | 0 |
| A1AT | 4 | A2M | 0 |
| APOE genotype | 3 | B2M | 0 |
| RANTES | 3 | BDNF | 0 |
| ApoC3 | 3 | CFH | 0 |
| PAI-1 | 2 | ApoA1 | 0 |
| CRP | 2 | Ab40 | 0 |

Proteins are ranked according to the number of times a protein was observed in the feature selection;
proteins highlighted in bold were taken forward as the predictors for MCI conversion.

Cut-Off Point Analysis

Untransformed protein concentrations on the full dataset (n=169 MCI-converter $MCI_c$ and MCI-nonconverter ($MCI_{nc}$)) were binarised at different cut-off points using the upper and lower quartile ranges and the percentile rank. A minimum of three cut-off concentrations were tested per protein. Logistic regression analysis was performed on individual cut-off concentrations and selected based on their accuracy of predicting conversion.

Results

Study Participants

The demographic and clinical characteristics of participants from the three cohorts are presented in Table 2. The AD group were marginally, but significantly older than controls (AD: mean 77 yrs, Controls: 75 yrs, p=0.012). The frequency of the APOEε4 allele was higher in MCI and AD groups than controls.

Plasma Proteins and Disease Pathology

Preliminary analysis showed that only two proteins were found to be significantly different between AD and controls (ApoE: F=6.5, p<0.001; CFH: F=6.1, p<0.001). However, using partial correlation, and after adjusting for APOE, the inventors identified a number of plasma proteins that were significantly associated with atrophy using MRI measures of one or more of the brain regions hippocampus, entorhinal cortex, ventricles and whole brain volume in the disease groups (Table 4; sections a and b). Controlling for multiple testing, only Clusterin (MCI group: p<0.001) and ApoE (AD group: p=0.0014) remained significant.

TABLE 4

Proteins identified as significantly associated with
structural brain MRI measures in the (a) MCI group and (b) AD group

|  | Protein | Correlation coefficient* | Significance (2-tailed) | df |
|---|---|---|---|---|
| (a) MCI Brain Regions | | | | |
| Ventricular volume | Clusterin | 0.23 | 0.01 | 115 |
|  | RANTES | −0.19 | 0.03 | 116 |
| Mean hippocampal volume | Clusterin | −0.38 | 0.00 | 115 |
|  | NSE | 0.22 | 0.02 | 116 |
| Right Entorhinal thickness | Clusterin | −0.22 | 0.02 | 115 |
| Left Entorhinal thickness | Transthyretin | −0.20 | 0.04 | 109 |
| Whole Brain Volume | Clusterin | −0.25 | 0.01 | 118 |
|  | NSE | 0.21 | 0.02 | 119 |
|  | RANTES | 0.19 | 0.04 | 119 |
| (b) AD Brain Regions | | | | |
| Ventricular volume | A1AT | 0.24 | 0.01 | 119 |
|  | NSE | 0.16 | 0.03 | 169 |
| Mean hippocampal volume | BDNF | −0.21 | 0.02 | 123 |
|  | ApoC3 | −0.18 | 0.02 | 168 |
|  | ApoA1 | −0.15 | 0.04 | 169 |
|  | ApoE | −0.15 | 0.05 | 169 |
| Mean Entorhinal volume | ApoC3 | −0.204 | 0.01 | 168 |
|  | ApoE | −0.177 | 0.02 | 169 |
| Mean Entorhinal Thickness | ApoC3 | −0.217 | 0.00 | 168 |
|  | ApoA1 | −0.209 | 0.01 | 169 |
|  | ApoE | −0.198 | 0.01 | 169 |
|  | Transthyretin | −0.154 | 0.05 | 158 |
| Whole Brain Volume | ApoE | −0.19 | 0.02 | 145 |
|  | ApoA1 | −0.19 | 0.02 | 145 |
|  | Aβ40 | 0.17 | 0.04 | 141 |

MRI: magnetic resonance imaging;
*Pearson's correlation coefficient.

The inventors then set out to identify a set of proteins that together would predict disease pathology in a pre-disease group of MCI as represented by the surrogate of hippocampal atrophy. Using multiple linear regression analysis, six proteins (Clusterin, RANTES, NSE, TTR, VCAM-1 and SAP) were identified as able to predict 19.5% (p=0.006) of hippocampal volume in the MCI group. A different combination of proteins associated with atrophy in the AD group was observed. Using linear regression analysis, 7 proteins (APOA1, A1AT, ApoC3, BDNF, Aβ40, PAI-1 and NSE) in the AD group were identified as able to predict 11.9% (p=0.039) of hippocampal volume.

Surprisingly, an association of clusterin with greater atrophy, and a trend to a decrease in RANTES, NSE and TTR levels in the MCI group was found. Unexpectedly, in the AD group A1AT, NSE, ApoC3, ApoA1, ApoE, BDNF plasma levels were increased alongside greater atrophy.

Plasma Proteins Clinical Cognition and Cognitive Decline

The relationship between these proteins and disease severity as measured by cognition at the time of sampling and by rate of change in cognition was examined. In the MCI group at the time of sampling, both ApoE and CRP negatively correlated with MMSE (ApoE: r=−0.150, p=0.001; CRP: r=−0.186, p=0.007).

In the AD group at the time of sampling ApoE, CFH, NCAM, AB40, A1AcidG and clusterin were all negatively correlated with MMSE (ApoE: r=−0.150, p=0.001; CFH: r=−0.104, p=0.026; NCAM: r=−0.114, p=0.014; AB40: r=−0.161, p=0.001; A1AcidG: r=−0.135, p=0.004; clusterin: r=−0.135, p=0.004).

Furthermore, the association of the proteins with longitudinal prospective MMSE changed in the AD group. Three novel proteins, NCAM, sRAGE and ICAM were significantly associated with the MMSE cognitive slope. NCAM and sRAGE were both negatively correlated with the rate of decline in cognition as measured by change in MMSE (NCAM: r=−0.129, p=0.0018; sRAGE: r=−0.125, p=0.029) whereas ICAM was positively correlated (ICAM: r=0.108, p=0.047).

Protein Biomarkers to Predict Disease Conversion of MCI to AD

A number of proteins, previously identified as putative markers of AD, correlated with disease pathology, whether measured by MRI or by severity of cognitive impairment not only in disease but in the pre-disease state of MCI. These proteins were believed reflecting pathological load and hence thought to be markers predictive of conversion from pre-disease states such as MCI to clinical dementia. To confirm this, a machine learning approach was used (Naïve Bayes Simple) with feature selection on a training dataset and subsequently on the relevant test set. A total of 220 samples were analysed (N=220; MCI$_{nc}$=169 and MCI$_c$=51). The average time of conversion of MCI to AD was 375 days (SD=23 days). Ten proteins (TTR, Clusterin, Cystatin C, A1AcidG, ICAM1, CC4, PEDF, A1AT, RANTES, ApoC3) plus APOE genotype were observed to have the greatest predictive power (Table 3). The Receiving Operating Characteristics Area Under the Curve, also known as ROC AUCs, from the test set were 0.78 (protein only) and 0.84 (protein+APOE genotype) (Table 5). In order to test the accuracy, three different sensitivity cut-off points at 30%, 50% and 85% were investigated. The optimal accuracy was observed at the 85% sensitivity with the test achieving an accuracy of 87% with a specificity of 88% (in bold in Table 5).

TABLE 5

Characteristics of the ROC curve for the full dataset

| Classification model | Sensitivity cut-off % | SN % | SP % | PPV % | NPV % | ACC % | ROC |
|---|---|---|---|---|---|---|---|
| Protein + APOE | 30 | 30.8 | 92.9 | 57.1 | 81.3 | 87.2 | 0.84 |
| Protein only | 30 | 30.8 | 92.9 | 57.1 | 81.3 | 87.2 | 0.78 |
| Protein + APOE | 50 | 53.9 | 88.1 | 58.3 | 86.1 | 80.0 | 0.84 |
| Protein only | 50 | 43.8 | 84.6% | 53.9 | 78.6 | 72.7 | 0.78 |
| Protein + APOE | 85 | 84.6 | 88.1 | 68.8 | 94.9 | 87.2 | 0.84 |
| Protein only | 85 | 84.6 | 71.4 | 47.8 | 93.8 | 74.5 | 0.78 |

Sensitivity (SN), specificity (SP), positive predictive value (PPV), negative predictive value (NPV), Accuracy (ACC) and ROC for the protein and APOE classifier.

It was then investigated whether combining structural MRI data with the 10 markers observed in the MCI conversion data would improve classification accuracy. MRI brain measures for a subset of subjects were combined with the protein data and the Naïve Bayes algorithm was applied. In this smaller dataset the proteins alone performed very well when tested at the 3 different sensitivity cut-off (Cut-off: accuracy; 30%: 83.33%, 50%: 80.56%, 85%: 69.44%). The addition of MRI data only marginally improved the accuracy at the 2 cut-off points (Cut-off: accuracy 30%: 86%; 50%: 83%). However at the 85% sensitivity cut-off the accuracy reduced to 64%. The ROC curve, sensitivity, specificity, positive and negative predictive values of each classifier is shown in Table 6.

TABLE 6

Characteristics of the ROC curve for the subset with protein plus MRI imaging data

| Classification model | Sensitivity cut-off % | SN % | SP % | PPV % | NPV % | ACC % | ROC |
|---|---|---|---|---|---|---|---|
| Protein + APOE + MRI | 30 | 33.3 | 96.7 | 66.7 | 87.9 | 86.1 | 0.75 |
| Protein only | 30 | 33.3 | 93.3 | 50.0 | 87.5 | 83.3 | 0.82 |
| MRI only | 30 | 33.3 | 80.0 | 25.0 | 85.7 | 72.2 | 0.54 |
| Protein + APOE + MRI | 50 | 50.0 | 90.0 | 50.0 | 90.0 | 83.3 | 0.75 |
| Protein only | 50 | 50.0 | 86.7 | 42.9 | 89.7 | 80.6 | 0.82 |
| MRI only | 50 | 50.0 | 63.3 | 21.3 | 86.4 | 61.1 | 0.54 |
| Protein + APOE + MRI | 85 | 83.3 | 60.0 | 29.4 | 94.7 | 63.9 | 0.75 |
| Protein only | 85 | 83.3 | 66.7 | 33.3 | 95.2 | 69.4 | 0.82 |
| MRI only | 85 | 83.3 | 13.3 | 16.1 | 80.0 | 25.0 | 0.54 |

Sensitivity (SN), specificity (SP), positive predictive value (PPV), negative predictive value (NPV) Accuracy (ACC) and ROC for the protein and APOE classifier.

Concentration Cut-Offs Points for Proteins Predicting MCI to AD

Individual protein cut-off values were derived for the 10 markers identified by feature selection in the MCI conversion model. These are as follows; ApoC3 105.5 ug/ml, TTR 222 ug/ml, A1AT 9.5 ug/ml, PEDF 10.7 ug/ml, CC4 78.5 ug/ml, ICAM-1 99.72 ng/ml, RANTES 33.8 ng/ml, A1AcidG 768.3 ug/ml, cystatin C 3.21 ug/ml, clusterin 402ug/ml. Logistic regression analysis was used to test the 10 markers cut-off concentrations and APOE genotype, the overall model accuracy was 94.9%, with a sensitivity 73.6%, and specificity of 94.9% when using the full dataset.

Discussion

Previous studies using data-driven pan-proteomic approaches have identified a number of proteins as diagnostic[1], progression[7,20] and pathology markers[18]. The advent of high throughput multiplex platforms facilitates the replication of such findings and raises the potential of high throughput multiplexed markers for use in clinical practice and in clinical trials[21-22]. Here the inventors have determined if any of those putative biomarkers are associated with early disease stages and might have value as prognostic markers. Using MRI as a surrogate of disease pathology, a number of markers associated with atrophy either early in the disease process (MCI) or in established dementia were found.

This approach of using MRI as a proxy for in vivo pathology has previously been shown to be useful in biomarker discovery, such as identifying clusterin as a putative marker of disease[7].

In the present study, however, it was surprisingly found that RANTES, NSE and transthyretin, in addition to clusterin, are associated with cortical atrophy in the MCI group, with clusterin showing the strongest correlation with all brain regions assessed.

RANTES, also known as chemokine ligand 5 (CCL5), is a protein known to have an active role in recruiting leukocytes into inflammatory sites. A negative association was unexpectedly found between RANTES and ventricular volume, suggesting a decreased level with increased pathology; this is the opposite to previous reports in neurodegeneration[24-26]. Without wishing to be bound by theory, it is believed that the association of the protein RANTES with atrophy only in MCI and not in AD may be due to a decrease early in disease process followed by a later increase. Similar findings have been previously reported for other proteins[27].

This atypical behaviour was surprisingly found in association with pathology for the neuron-specific enolase (NSE) protein. This protein is thought to be a good indicator of acute neuronal damage[28-29] and has been associated with AD in some but not all previous studies[30,31]. In contrast, an unanticipated positive association between NSE and volume of hippocampus and whole brain was found in MCI subjects. However, in the AD group the positive association was instead found with ventricular volume. This inverse relationship with atrophy in pre-disease and then positive correlation with atrophy in disease suggests that, like RANTES, NSE might be decreased in early disease stages (i.e. MCI) with a rebound elevation in established AD. In established AD, a different set of proteins associated with pathology as measured by atrophy on MRI are found. A number of these belong to the group of apolipoproteins (ApoE, ApoC3 and ApoA1). All of these proteins are found to be negatively associated with hippocampal, entorhinal cortical and whole brain volumes. The roles of apolipoproteins in neurodegenerative disorders have been studied extensively since the discovery that APOE was a major susceptibility gene for AD[32-33]. In the peripheral system, ApoE serves the transport of triglycerides, phospholipids and cholesterol into cells[34]. The literature on ApoE is conflicting with some groups reporting lower ApoE in AD[35-36], with others showing increased levels[37-38]. ApoE plasma measurements derived from this study have been recently published and are in agreement with the findings from the North American Alzheimer's Disease Neuroimaging Initiative which shows an APOE genotype effect[39].

Accordingly, this represents the first time that a panel of markers in plasma, associated with neuroimaging measures of the disease, has been identified as a biomarker panel of early disease severity. Moreover, a set of ten markers that can prospectively predict disease conversion from MCI to AD within a year (12 months) of test sampling is disclosed herein. This time-frame is crucial as it is important to identify early the subset of MCI subjects that will progress to clinical AD, as eventually all converters will progress to AD given time. These results are supported by further evidence from other studies that plasma proteins can have a role in early disease detection with inflammatory proteins in particular identified as possible predictors of conversion from MCI[23,40]. Combining MRI with protein measures did not improve predictive power in contrast to previous studies where CSF (not plasma) marker performance was improved in combination with MRI[41].

In summary, three large multicentre cohorts coupled with multiplex protein assays lead to validate a plasma biomarker panel reflecting disease pathology and for predicting disease progression. Such a biomarker panel might have considerable value in triaging patients with early memory disorders to yet more specific but more invasive and costly approaches such as molecular markers in CSF and on PET imaging in clinical trials and possibly in clinical practice.

REFERENCES

1. Hye A, Lynham S, Thambisetty M, Causevic M, Campbell J, Byers H L, et al. Proteome-based plasma biomarkers for Alzheimer's disease. Brain. 2006 November; 129 (Pt 11):3042-50.
2. Cutler P, Akuffo E L, Bodnar W M, Briggs D M, Davis J B, Debouck C M, et al. Proteomic identification and early validation of complement 1 inhibitor and pigment epithelium-derived factor: Two novel biomarkers of Alzheimer's disease in human plasma. Proteomics Clinical applications. 2008 April; 2(4):467-77.
3. Akuffo E L, Davis J B, Fox S M, Gloger I S, Hosford D, Kinsey E E, et al. The discovery and early validation of novel plasma biomarkers in mild-to-moderate Alzheimer's disease patients responding to treatment with rosiglitazone. Biomarkers. 2008; 13(6):618-36.
4. Kimura M, Asada T, Uno M, Machida N, Kasuya K, Taniguchi Y, et al. Assessment of cerebrospinal fluid levels of serum amyloid P component in patients with Alzheimer's disease. Neuroscience letters. 1999 Oct. 1; 273(2):137-9.
5. Kessler H, Pajonk F G, Meisser P, Schneider-Axmann T, Hoffmann K H, Supprian T, et al. Cerebrospinal fluid diagnostic markers correlate with lower plasma copper and ceruloplasmin in patients with Alzheimer's disease. J Neural Transm. 2006 November; 113(11):1763-9.
6. Mulder S D, Hack C E, van der Flier W M, Scheltens P, Blankenstein M A, Veerhuis R. Evaluation of intrathecal serum amyloid P (SAP) and C-reactive protein (CRP) synthesis in Alzheimer's disease with the use of index values. Journal of Alzheimer's disease: JAD. 2010; 22(4):1073-9.
7. Thambisetty M, Simmons A, Velayudhan L, Hye A, Campbell J, Zhang Y, et al. Association of plasma clusterin concentration with severity, pathology, and progression in Alzheimer disease. Archives of general psychiatry. 2010 July; 67(7):739-48.
8. Velayudhan L, Killick R, Hye A, Kinsey A, Guntert A, Lynham S, et al. Plasma transthyretin as a candidate marker for Alzheimer's disease. J Alzheimers Dis. 2012; 28(2):369-75.
9. Thambisetty M, Tripaldi R, Riddoch-Contreras J, Hye A, An Y, Campbell J, et al. Proteome-based plasma markers of brain amyloid-beta deposition in non-demented older individuals. J Alzheimers Dis. 2010; 22(4):1099-109.
10. Lovestone S, Francis P, Kloszewska I, Mecocci P, Simmons A, Soininen H, et al. AddNeuroMed—the European collaboration for the discovery of novel biomarkers for Alzheimer's disease. Annals of the New York Academy of Sciences. 2009 October; 1180:36-46.
11. Petersen R C, Smith G E, Waring S C, Ivnik R J, Tangalos E G, Kokmen E. Mild cognitive impairment: clinical characterization and outcome. Archives of neurology. 1999 March; 56(3):303-8.
12. Wenham P R, Price W H, Blandell G. Apolipoprotein E genotyping by one-stage PCR. Lancet. 1991 May 11; 337(8750):1158-9.
13. Simmons A, Westman E, Muehlboeck S, Mecocci P, Vellas B, Tsolaki M, et al. MRI measures of Alzheimer's disease and the AddNeuroMed study. Annals of the New York Academy of Sciences. 2009 October; 1180:47-55.
14. Jack C R, Jr., Bernstein M A, Fox N C, Thompson P, Alexander G, Harvey D, et al. The Alzheimer's Disease Neuroimaging Initiative (ADNI): MRI methods. Journal of magnetic resonance imaging: JMRI. 2008 April; 27(4):685-91.
15. Simmons A, Westman E, Muehlboeck S, Mecocci P, Vellas B, Tsolaki M, et al. The AddNeuroMed framework for multi-centre MRI assessment of Alzheimer's disease: experience from the first 24 months. Int J Geriatr Psychiatry. 2011 January; 26(1):75-82.
16. Westman E, Simmons A, Muehlboeck J S, Mecocci P, Vellas B, Tsolaki M, et al. AddNeuroMed and ADNI: similar patterns of Alzheimer's atrophy and automated MRI classification accuracy in Europe and North America. NeuroImage. 2011 Oct. 1; 58(3):818-28.
17. Westman E, Simmons A, Zhang Y, Muehlboeck J S, Tunnard C, Liu Y, et al. Multivariate analysis of MRI data for Alzheimer's disease, mild cognitive impairment and healthy controls. NeuroImage. 2011 Jan. 15; 54(2):1178-87.
18. Thambisetty M, Simmons A, Hye A, Campbell J, Westman E, Zhang Y, et al. Plasma biomarkers of brain atrophy in Alzheimer's disease. PLoS One. 2011; 6(12):e28527.
19. Westman E, Aguilar C, Muehlboeck J S, Simmons A. Regional magnetic resonance imaging measures for multivariate analysis in Alzheimer's disease and mild cognitive impairment. Brain Topogr. 2013 January; 26(1):9-23.
20. Guntert A, Campbell J, Saleem M, O'Brien D P, Thompson A J, Byers H L, et al. Plasma gelsolin is decreased and correlates with rate of decline in Alzheimer's disease. Journal of Alzheimer's disease: JAD. 2010; 21(2):585-96.
21. Hu W T, Holtzman D M, Fagan A M, Shaw L M, Perrin R, Arnold S E, et al. Plasma multianalyte profiling in mild cognitive impairment and Alzheimer disease. Neurology. 2012 Aug. 28; 79(9):897-905.
22. O'Bryant S E, Xiao G, Barber R, Huebinger R, Wilhelmsen K, Edwards M, et al. A blood-based screening tool for Alzheimer's disease that spans serum and plasma: findings from TARC and ADNI. PloS one. 2011; 6(12):e28092.
23. Ray S, Britschgi M, Herbert C, Takeda-Uchimura Y, Boxer A, Blennow K, et al. Classification and prediction of clinical Alzheimer's diagnosis based on plasma signaling proteins. Nat Med. 2007 November; 13(11):1359-62.
24. Gangemi S, Basile G, Merendino R A, Epifanio A, Di Pasquale G, Ferlazzo B, et al. Effect of levodopa on interleukin-15 and RANTES circulating levels in patients affected by Parkinson's disease. Mediators Inflamm. 2003 August; 12(4):251-3.
25. Grzybicki D, Moore S A, Schelper R, Glabinski A R, Ransohoff R M, Murphy S. Expression of monocyte chemoattractant protein (MCP-1) and nitric oxide synthase-2 following cerebral trauma. Acta Neuropathol. 1998 January; 95(1):98-103.
26. Tripathy D, Thirumangalakudi L, Grammas P. RANTES upregulation in the Alzheimer's disease brain: a possible neuroprotective role. Neurobiology of aging. 2010 January; 31(1):8-16.
27. Perrin R J, Craig-Schapiro R, Malone J P, Shah A R, Gilmore P, Davis A E, et al. Identification and validation of novel cerebrospinal fluid biomarkers for staging early Alzheimer's disease. PloS one. 2011; 6(1):e16032.
28. DeGiorgio C M, Gott P S, Rabinowicz A L, Heck C N, Smith T D, Correale J D. Neuron-specific enolase, a marker of acute neuronal injury, is increased in complex partial status epilepticus. Epilepsia. 1996 July; 37(7):606-9.
29. Hatfield R H, McKernan R M. CSF neuron-specific enolase as a quantitative marker of neuronal damage in a rat stroke model. Brain Res. 1992 Apr. 17; 577(2):249-52.
30. Chaves M L, Camozzato A L, Ferreira E D, Piazenski I, Kochhann R, Dall'Igna O, et al. Serum levels of S100B and NSE proteins in Alzheimer's disease patients. J Neuroinflammation. 2010; 7:6.
31. Blennow K, Wallin A, Ekman R. Neuron specific enolase in cerebrospinal fluid: a biochemical marker for neuronal degeneration in dementia disorders? J Neural Transm Park Dis Dement Sect. 1994; 8(3):183-91.
32. Lewis T L, Cao D, Lu H, Mans R A, Su Y R, Jungbauer L, et al. Overexpression of human apolipoprotein A-I preserves cognitive function and attenuates neuroinflammation and cerebral amyloid angiopathy in a mouse model of Alzheimer disease. J Biol Chem. 2010 Nov. 19; 285(47):36958-68.
33. Takechi R, Galloway S, Pallebage-Gamarallage M M, Wellington C L, Johnsen R D, Dhaliwal S S, et al. Differential effects of dietary fatty acids on the cerebral distribution of plasma-derived apo B lipoproteins with amyloid-beta. Br J Nutr. 2010 March; 103(5):652-62.
34. Eichner J E, Dunn S T, Perveen G, Thompson D M, Stewart K E, Stroehla B C. Apolipoprotein E polymorphism and cardiovascular disease: a HuGE review. American journal of epidemiology. 2002 Mar. 15; 155(6): 487-95.
35. Gupta V B, Laws S M, Villemagne V L, Ames D, Bush A I, Ellis K A, et al. Plasma apolipoprotein E and Alzheimer disease risk: the AIBL study of aging. Neurology. 2011 Mar. 22; 76(12):1091-8.
36. Siest G, Bertrand P, Qin B, Herbeth B, Serot J M, Masana L, et al. Apolipoprotein E polymorphism and serum concentration in Alzheimer's disease in nine European centres: the ApoEurope study. ApoEurope group. Clin Chem Lab Med. 2000 August; 38(8):721-30.
37. Darreh-Shori T, Forsberg A, Modiri N, Andreasen N, Blennow K, Kamil C, et al. Differential levels of apolipoprotein E and butyrylcholinesterase show strong association with pathological signs of Alzheimer's disease in the brain in vivo. Neurobiology of aging. 2011 December; 32(12):2320 e15-32.
38. Darreh-Shori T, Modiri N, Blennow K, Baza S, Kamil C, Ahmed H, et al. The apolipoprotein E epsilon4 allele plays pathological roles in AD through high protein expression and interaction with butyrylcholinesterase. Neurobiology of aging. 2011 July; 32(7):1236-48.
39. Kiddle S J, Thambisetty M, Simmons A, Riddoch-Contreras J, Hye A, Westman E, et al. Plasma based markers of [11C] PiB-PET brain amyloid burden. PLoS One. 2012; 7(9):e44260.
40. Furney S J, Kronenberg D, Simmons A, Guntert A, Dobson R J, Proitsi P, et al. Combinatorial markers of mild cognitive impairment conversion to Alzheimer's disease—cytokines and MRI measures together predict disease progression. J Alzheimers Dis. 2011; 26 Suppl 3:395-405.
41. Brys M, Glodzik L, Mosconi L, Switalski R, De Santi S, Pirraglia E, et al. Magnetic resonance imaging improves cerebrospinal fluid biomarkers in the early detection of Alzheimer's disease. Journal of Alzheimer's disease: JAD. 2009; 16(2):351-62.

The invention claimed is:

1. A diagnostic kit for Mild Cognitive Impairment (MCI) or Alzheimer's disease (AD) comprising reagents for the detection of a set of biomarkers in a tissue or body fluid sample, said reagents comprising:
   a plurality of primary antibodies, wherein each primary antibody specifically binds to a different biomarker in the set of biomarkers and the kit is configured to allow a user to determine a presence or level of expression of each biomarker in the set of biomarkers using an ELISA assay or Western blotting;
   wherein the set of biomarkers comprises transthyretin (TTR), Clusterin, Cystatin C (CST3), Alpha-1-Acid glycoprotein (A1AG1), Intercellular adhesion molecule 1 (ICAM1), Complement C4 (CC4), pigment epithelium derived factor (PEDF), Alpha1 antitrypsin (A1AT), regulated on activation, normal T cell expressed and secreted (RANTES), and Apolipoprotein C-III (ApoC3).

2. The kit according to claim 1, wherein the kit further comprises one or more secondary antibodies which specifically bind to one or more of the primary antibodies.

3. The kit according to claim 2, wherein the secondary antibodies are labelled.

4. The kit according to claim 1, wherein the kit further comprises a control sample for one or more of the biomarkers in the set of biomarkers, said control sample comprising an amount or concentration of the respective one or more biomarkers found in a tissue or body fluid sample obtained from: (a) a healthy individual; (b) a patient having MCI, AD, or symptoms thereof, and/or (c) a patient having MCI or AD, or symptoms thereof, not treated with a therapeutic agent for treating MCI or AD.

5. The kit according to claim 1, wherein the kit further comprises primary antibodies that specifically bind to at least one additional biomarker selected from the group consisting of: plasminogen activator inhibitor type 1 (PAI-1), C-reactive protein (CRP), Cathepsin D (CTSD) and apolipoprotein E (ApoE).

6. The kit according to claim 5, wherein the kit further comprises primary antibodies that specifically bind to at least one additional biomarker selected from the group consisting of: alpha-2-macroglobulin (A2M), serum amyloid P component (SAP), advanced glycosylation end product-specific receptor (sRAGE), Neuron specific enolase (NSE), complement factor H (CFH), amyloid beta (A4) precursor protein (AB40 or Aß40), Ceruloplasmin, neural cell adhesion molecule (NCAM), ApoA1, Abeta 42, BDNF, Beta-2-microglobulin (B2M), and VCAM-1.

7. The kit according to claim 1, wherein the set of biomarkers further comprises ApoE &4 allele presence (ApoE genotype).

8. The kit according to claim 1, further comprising at least one proteolytic enzyme.

9. The kit according to claim 1, further comprising a control sample for each of the biomarkers in the set of biomarkers.

10. The kit according to claim 1, wherein the set of biomarkers further comprises apolipoprotein E (ApoE).

11. The kit according to claim 1, wherein the set of biomarkers consists of: transthyretin (TTR), Clusterin, Cystatin C (CST3), Alpha-1-Acid glycoprotein (A1AG1), Intercellular adhesion molecule 1 (ICAM1), Complement C4 (CC4), pigment epithelium derived factor (PEDF), Alpha1 antitrypsin (A1AT), regulated on activation, normal T cell expressed and secreted (RANTES), and Apolipoprotein C-III (ApoC3).

12. The kit according to claim 1, wherein the set of biomarkers consists of: transthyretin (TTR), Clusterin, Cystatin C (CST3), Alpha-1-Acid glycoprotein (A1AG1), Intercellular adhesion molecule 1 (ICAM1), Complement C4 (CC4), pigment epithelium derived factor (PEDF), Alphal antitrypsin (A1AT), regulated on activation, normal T cell expressed and secreted (RANTES), and Apolipoprotein C-III (ApoC3), and apolipoprotein E (ApoE).

13. The kit according to claim 1, wherein the kit further comprises a control sample for each of the biomarkers in the set of biomarkers, said control sample comprising an amount or concentration of the biomarker found in a tissue or body fluid sample obtained from: (a) a healthy individual; (b) a patient having MCI, AD, or symptoms thereof; and/or (c) a patient having MCI or AD, or symptoms thereof, not treated with a therapeutic agent for treating MCI or AD.

14. The kit according to claim 1, wherein the kit further comprises a control sample for one or more of the biomarkers in the set of biomarkers, said control sample comprising an amount or concentration of the respective one or more biomarkers found in a tissue or body fluid sample obtained from a patient having MCI, AD, or symptoms thereof.

15. The kit according to claim 1, wherein the kit further comprises a control sample for each of the biomarkers in the set of biomarkers, said control sample comprising an amount or concentration of the biomarker found in a tissue or body fluid sample obtained from a patient having MCI, AD, or symptoms thereof.

16. A diagnostic kit for Mild Cognitive Impairment (MCI) or Alzheimer's disease (AD) comprising reagents for the detection of a set of biomarkers in a tissue or body fluid sample, said reagents comprising:
 a plurality of primary antibodies, wherein each primary antibody specifically binds to a different biomarker in the set of biomarkers;
 wherein the set of biomarkers comprises transthyretin (TTR), Clusterin, Cystatin C (CST3), Alpha-1-Acid glycoprotein (A1AG1), Intercellular adhesion molecule 1 (ICAM1), Complement C4 (CC4), pigment epithelium derived factor (PEDF), Alphal antitrypsin (A1AT), regulated on activation, normal T cell expressed and secreted (RANTES), and Apolipoprotein C-III (ApoC3).

* * * * *